US011623928B2

(12) United States Patent
Haddach

(10) Patent No.: US 11,623,928 B2
(45) Date of Patent: *Apr. 11, 2023

(54) COMPOSITIONS, USES AND METHODS FOR MAKING THEM

(71) Applicant: Pimera, Inc., San Diego, CA (US)

(72) Inventor: Mustapha Haddach, San Diego, CA (US)

(73) Assignee: PIMERA, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/925,220

(22) Filed: Jul. 9, 2020

(65) Prior Publication Data

US 2021/0094952 A1    Apr. 1, 2021

Related U.S. Application Data

(63) Continuation of application No. 16/430,129, filed on Jun. 3, 2019, now Pat. No. 10,745,403, which is a continuation of application No. 15/864,965, filed on Jan. 8, 2018, now Pat. No. 10,442,801, which is a continuation of application No. 15/485,106, filed on Apr. 11, 2017, now Pat. No. 9,951,066, which is a continuation of application No. 14/935,155, filed on Nov. 6, 2015, now Pat. No. 9,758,518, which is a continuation of application No. 14/708,230, filed on May 9, 2015, now Pat. No. 9,512,123.

(60) Provisional application No. 61/991,282, filed on May 9, 2014, provisional application No. 62/050,020, filed on Sep. 12, 2014, provisional application No. 62/054,054, filed on Sep. 23, 2014, provisional application No. 62/128,208, filed on Mar. 4, 2015.

(51) Int. Cl.
C07D 471/14 (2006.01)
C07D 487/14 (2006.01)
C07D 471/04 (2006.01)
A61P 35/00 (2006.01)
C07D 471/22 (2006.01)

(52) U.S. Cl.
CPC ............ *C07D 471/14* (2013.01); *A61P 35/00* (2018.01); *C07D 471/04* (2013.01); *C07D 471/22* (2013.01); *C07D 487/14* (2013.01)

(58) Field of Classification Search
CPC .. C07D 471/14; C07D 487/14; C07D 471/04; C07D 471/22; A61P 35/00
See application file for complete search history.

(56) References Cited

U.S. PATENT DOCUMENTS

| | | | |
|---|---|---|---|
| 1,042,801 A | 10/1912 | Kitsee | |
| 4,650,737 A | 3/1987 | Wiedemann et al. | |
| 5,624,677 A | 4/1997 | El-Rashidy et al. | |
| 7,141,565 B1 | 11/2006 | Whitten et al. | |
| 7,326,702 B2 | 2/2008 | Whitten et al. | |
| 7,354,916 B2 | 4/2008 | Whitten et al. | |
| 7,381,720 B2 | 6/2008 | Whitten et al. | |
| 7,402,579 B2 | 7/2008 | Whitten et al. | |
| 7,507,727 B2 | 3/2009 | Whitten et al. | |
| 7,612,063 B2 | 11/2009 | Whitten et al. | |
| 7,652,134 B2 | 1/2010 | Whitten et al. | |
| 7,816,406 B2 | 10/2010 | Whitten et al. | |
| 7,816,524 B2 | 10/2010 | Chua et al. | |
| 7,928,100 B2 | 4/2011 | Nagasawa et al. | |
| 7,998,978 B2 | 8/2011 | Huang et al. | |
| 8,142,909 B2 | 3/2012 | Beers et al. | |
| 8,518,952 B2 | 8/2013 | Braganza et al. | |
| 8,637,529 B2 | 1/2014 | Woller et al. | |
| 9,512,123 B2 | 12/2016 | Haddach | |
| 9,688,697 B2 | 6/2017 | Achiron et al. | |
| 9,758,518 B2 | 9/2017 | Haddach | |
| 9,951,066 B2 | 4/2018 | Haddach | |
| 10,590,134 B2 | 3/2020 | Haddach | |
| 10,745,403 B2 | 8/2020 | Haddach | |
| 2011/0218184 A1 | 9/2011 | Nagasawa et al. | |
| 2012/0007069 A1 | 1/2012 | Lee et al. | |
| 2015/0284410 A1 | 10/2015 | Achiron et al. | |
| 2016/0257678 A1 | 9/2016 | Haddach et al. | |
| 2017/0143737 A1 | 5/2017 | Soong | |
| 2019/0233422 A1 | 8/2019 | Haddach | |
| 2020/0361937 A1 | 11/2020 | Haddach | |
| 2021/0317120 A1 | 10/2021 | Haddach | |

FOREIGN PATENT DOCUMENTS

| | | |
|---|---|---|
| CN | 101781312 A | 7/2010 |
| CN | 101888780 A | 11/2010 |
| CN | 106349244 A | 1/2017 |
| DE | 2929414 A1 | 2/1981 |
| EP | 1325009 B1 | 3/2006 |
| EP | 2414355 A2 | 2/2012 |
| JP | S5333227 A | 3/1978 |

(Continued)

OTHER PUBLICATIONS

Jaworska et al. (2004).*
Balduzzi et al. Trastuzumab-containing regimens for metastatic breast cancer (Review). Cochrane Database of Systematic Reviews pp. 1-4 (2014).
U.S. Appl. No. 16/739,354 Office Action dated Apr. 8, 2021.
Akira Ogata. Chemical Experimental Procedures, Nankodo Co., Ltd., pp. 366 to 399 (1963).
Hirayama Yoshinaki. Handbook of organic compound crystal—Principle and know-how, Marzen Co., Ltd., p. 57-84 (Jan. 25, 2008).
Takata. API form Screening and selection in the stage of drug development. Pharm Stage 6(10):20-25 (2007).
Achiron et al. RAM-589.555 a new Polymerase-1 inhibitor as innovative targeted-treatment for multiple sclerosis. Journal of Neuroimmunology 302:41-48 (2017).

(Continued)

*Primary Examiner* — Shirley V Gembeh
(74) *Attorney, Agent, or Firm* — Wilson Sonsini Goodrich & Rosati

(57) ABSTRACT

Generally, the present invention provides novel quinolone compounds and pharmaceutical composition thereof which may inhibit cell proliferation and/or induce cell apoptosis. The present invention also provides methods of preparing such compounds and compositions, and methods of making and using the same.

6 Claims, No Drawings

(56) References Cited

FOREIGN PATENT DOCUMENTS

| JP | S61175647 A | 8/1986 |
|---|---|---|
| JP | H08245540 A | 9/1996 |
| KR | 20120061056 A | 6/2012 |
| KR | 20130090726 A | 8/2013 |
| WO | WO-0228860 A2 | 4/2002 |
| WO | WO-2007038215 A1 | 4/2007 |
| WO | WO-2008060693 A2 | 5/2008 |
| WO | WO-2009046383 A1 | 4/2009 |
| WO | WO-2010135751 A2 | 11/2010 |
| WO | WO-2013059559 A2 | 4/2013 |
| WO | WO-2015172123 A1 | 11/2015 |
| WO | WO-2016141042 A2 | 9/2016 |
| WO | WO-2018183540 A1 | 10/2018 |

OTHER PUBLICATIONS

Agrawal et al. Synthesis, Analytical Analysis and Medicinal Aspect of Novel Benzimidazoles and their Megal Complexes. Chem Biol Drug Des 82:630-634 (2013).
Andaloussi et al., Novel imidazo[1,2-a]naphthyridinic systems (part 1): synthesis, antiproliferative and DNA-intercalating activities. European Journal of Medicinal Chemistry 43(11):2505-2517 (2008).
Augustine et al. gem-Dibromomethylarenes: a convenient substitute for noncommercial aldehydes in the knoevenagel-doebner reaction for the synthesis of alpha,beta-unsaturated carboxylic acids. J Org Chem 72:9854-9856 (2007).
Babichev et al. Unexpected O →N-migration of methyl group in 5-methoxy-6-cyanobenzimidazo[1,2-a][1,8]naphthyridine. Chem Heterocycl Compd 25:230 (1989).
Beaulieu et al., Synthesis and biological evaluation of 4-amino derivatives of benzimidazoquinoxaline, benzimidazoquinoline, and benzopyrazoloquinazoline as potent IKK inhibitors. Bioorg Med Chem Lett. 17(5):1233-1237 (2007).
Berge et al. Pharmaceutical Salts. Journal of Pharmaceutical Sciences 66(1):1-19 (Jan. 1977).
Bundgaard. Chapter 5: Design and Application of Prodrugs. A Textbook of Drug Design and Development, (pp. 113-191) (1991).
Bundgaard. Means to Enhance Penetration: Prodrugs as a Means to Improve the Delivery of Peptide Drugs. Advanced Drug Delivery Review 8:1-38 (1992).
Cai et al. Synthesis of Aza-Fused Polycyclic Quinolines through Copper-Catalyzed Cascade Reactions. Organic Letters 12(7):1500-1503 (2010).
Chemical Abstract Compounds, STN Registry entry for RN 183858-23-3 (1996).
Chemical Abstract Compounds, STN Registry entry for RN 183858-24-4 (1996).
Chemical Abstract Compounds, STN Registry entry for RN 93438-49-4 (1984).
Chen et al. Overexpression of 5-lipoxygenase in rat and human esophageal adenocarcinoma and inhibitory effects of zileuton and celecoxib on carcinogenesis. Clin Cancer Res. 10(19):6703-9 (2004).
Cortes et al. Effect of Low Doses of Actinomycin D on Neuroblastoma Cell Lines. Molecular Cancer 15:1 (2016).
Ding et al. A novel anti-pancreatic cancer agent, LY293111. Anti-cancer Drugs 16(5):467-473 (2005).
Drygin et al. Anticancer activity of CX-3543: a direct inhibitor of rRNA biogenesis. Cancer Res 69:7653-7661 (2009).
Drygin et al. RNA Polymerase I Transcription. Encyclopedia of Cancer pp. 1-5 (2014).
Ebitani et al. Reconstructed hydrotalcite as a highly active heterogeneous base catalyst for carbon-carbon bond formations in the presence of water. J Org Chem 71:5440-5447 (2006).
Hranjec et al. Benzimidazole Derivatives related to 2,3-acrylonitriles, benzimidazo [1,2-a] Quinolines and Fluorenes: Synthesis, Antitumor Evaluation in vitro and crystal structure determination. European Journal of Medicinal Chemistry 45:2405-2417 (2010).
Hranjec et al. Novel Cyano- and Amidino-Substituted Derivatives of Styryl-2-Benzimidazoles and Benzimidazo[1,2-a]quinolines. Synthesis, Photochemical Synthesis, DNA Binding, and Antitumor Evaluation, Part 3. J Med Chem 50(23):5696-711 (2007).
Hranjec et al. Synthesis of novel benzimidazolyl-substituted acrylonitriles and amidino-substituted benzimidazo[1,2-a]quinolines. Molecules 12:1817-1828 (2007).
Huang et al. An efficient one-pot synthesis of benzo[4,5]imidazo[1,2-a]quinoxalines via copper-catalyzed process. Org Lett. 15(21):5480-3 (2013).
Hudis. Trastuzumab—Mechanism of Action and Use in Clinical Practice. The New England Journal of Medicine 357(1):39-51 ((Jul. 5, 2007).
Kato et al. Novel Strategy for Synthesis of Substituted Benzimidazo[1,2-a]quinolines. Organic Letters 15:3794-3797 (2013).
Kim et al. Genetic Requirement for Mycl and Efficacy of Rna Pol I inhibition in Mouse Models of Small Cell Lung Cancer. Genes Develop 30:1289-1299 (2016).
Leung et al. Copper-CX-5461: A novel liposomal formulation for small molecule rRNA synthesis inhibitor. Journal of Controlled Release 286:1-9 (2018).
Lu et al. Organocatalytic Decarboxylative Doebner-Knoevenagel Reactions between Arylaldehydes and Monoethyl Malonate Mediated by a Bifunctional Polymeric Catalyst. Synlett 2011(12):1723-1726 (2011).
Mase et al. Organocatalytic Knoevenagel condensations by means of carbamic acid ammonium salts. Org Lett 15:1854-1857 (2013).
Mogilaiah et al. Synthesis of Some Novel Bridgehead Nitrogen Heterocyclic Systems Containing 1,8-Naphthyridine Moiety. Indian Journal of Chemistry 42B:192-194 (2003).
Mohite et al. A practical and convenient protocol for the synthesis of (E)-α,β-unsaturated acids. Org Lett 15:4564-4567 (2013).
PCT/US2015/030046 International Search Report and Written Opinion dated Sep. 10, 2015.
PCT/US2016/020418 International Search Report and Written Opinion dated Aug. 30, 2016.
PCT/US2018/024898 International Search Report and Written Opinion dated Aug. 9, 2018.
Perin et al., Biological Activity and DNA Binding Studies of 2-Substituted Benzimidazo [1,2-a]quinolines bearing different amino side chains. Medicinal Chemistry Communication 4:1537 (2013).
Perin et al. Novel biologically active nitro and amino substituted benzimidazo[1,2-a]quinolines. Bioorg Med Chem. 19(21):6329-39 (2011).
Perin et al. Synthesis, Antiproliferative Activity and DNA Binding Properties of Novel 5-Aminobenzimidazo [1,2-a] quinoline-6-carbonitriles. European Journal of Medicinal Chemistry 80:218-227 (2014).
Ranu et al. Ionic Liquid as Catalyst and Reaction Medium—A Simple, Efficient and Green Procedure for Knoevenagel Condensation of Aliphatic and Aromatic Carbonyl Compounds Using a Task-Specific Basic Ionic Liquid. Eur J Org Chem 2006(16):3767-3770 (2006).
Rebello et al. The Dual Inhibition of RNA Pol 1 Transcription and PIM Kinase as a New Therapeutic Approach to Treat Advanced Prostate Cancer. American Association for Cancer Research 22:5539-5552 (2016).
Schwaebe et al. Facile and Efficient Generation of Quinolone Amides from Esters Using Aluminum Chloride. Tetrahedron Letters 52:1096-1100 (2011).
Shvedov et al. Synthesis of derivatives of pyrazino[1,2-a]benzimidazole, aza analogs ofβ-carboline. Pharmaceutical Chemistry Journal 3(10):566-570 (1969) (Translated from Khimiko-Farmatsevticheskii Zhurnal 10, pp. 15-20, Oct. 1969) (English translation).
Shvedov et al., Synthesis of derivatives of pyrazino[1,2-a]benzimidazole, aza analogs of β-carboline. Pharmaceutical Chemistry Journal 3(10:)566-570 (1969).
Su et al. Organic Reactions in Ionic Liquids: Knoevenagel Condensation Catalyzed by Ethylenediammonium Diacetate. Synthesis 2003(4):0555-0559 (2003).
U.S. Appl. No. 14/708,230 Office Action dated Feb. 25, 2016.
U.S. Appl. No. 14/935,155 Office Action dated Jan. 27, 2017.

(56) References Cited

OTHER PUBLICATIONS

U.S. Appl. No. 15/485,106 Office Action dated Oct. 31, 2017.
U.S. Appl. No. 15/555,024 Office Action dated May 8, 2020.
U.S. Appl. No. 15/661,770 Office Action dated Jun. 12, 2018.
U.S. Appl. No. 15/864,965 Office Action dated May 31, 2018.
U.S. Appl. No. 16/430,129 Office Action dated Nov. 5, 2019.
Widder et al. Section III: Prodrugs Kinetics. Method in Enzymology. 112:309-396 (1985).
Wolfgang-R. Knappe, Photochemie des 10-phenylisoalloxazins: intramolekulare singulett-und intermolekulare triplett-reaktionen. Chemische Berichte 107:1614-1636 (1974).
Yadav et al. Phosphane-Catalyzed Knoevenagel Condensation: A Facile Synthesis of α-Cyanoacrylates and α-Cyanoacrylonitriles. Eur J Org Chem 2004(3):546-551 (2004).
Zanzoul et al., A benzimidazopyridoquinoxaline as promising scaffold for G-quadruplex DNA targeting. Medicinal Chemistry Research Sep. 2014, vol. 23:4042-4049 (2014).

* cited by examiner

COMPOSITIONS, USES AND METHODS FOR MAKING THEM

CROSS-REFERENCE TO RELATED APPLICATIONS

This application is a continuation of U.S. patent application Ser. No. 16/430,129; filed Jun. 3, 2019; which is a continuation of U.S. patent application Ser. No. 15/864,965; filed Jan. 8, 2018, now issued as U.S. Pat. No. 10,442,801; which is a continuation of U.S. patent application Ser. No. 15/485,106; filed Apr. 11, 2017, now issued as U.S. Pat. No. 9,951,066; which is a continuation of U.S. patent application Ser. No. 14/935,155, filed Nov. 6, 2015, now issued as U.S. Pat. No. 9,758,518; is a continuation of Ser. No. 14/708,230, filed May 9, 2015, now issued as U.S. Pat. No. 9,512,123, which claims priority to U.S. Provisional Patent Application No. 61/991,282, filed May 9, 2014; U.S. Provisional Patent Application No. 62/050,020, filed Sep. 15, 2014; U.S. Provisional Patent Application No. 62/054,054, filed Sep. 23, 2015; and U.S. Provisional Patent Application No. 62/128,208, filed Mar. 4, 2015, each of which are hereby incorporated by reference in their entirety

STATEMENT REGARDING FEDERAL FUNDING

This invention was made with government support under Federal Grant Number W81XWH-15-1-0224 awarded by the Department of Defense Office of the Congressionally Directed Medical Research Programs. The government has certain rights in the invention.

FIELD OF THE INVENTION

The present invention provides novel compounds and pharmaceutical composition thereof which may inhibit cell proliferation and/or induce cell apoptosis. The present invention also provides methods of preparing such compounds and compositions, and methods of making and using the same.

BACKGROUND OF THE INVENTION

Hypertrophy of the nucleolus, the cellular site for ribosome biogenesis, has been linked to malignant transformation for more than a hundred years. The ribosome is a RNA-protein complex that is responsible for the protein synthesis (translation) in the cell. Carcinogenesis, with the associated upregulation of growth and proliferation rates, requires a significant increase in the rate of translation and hence necessitates an increase in cellular ribosome content. Ribosome biogenesis is a highly complex energy-consuming process in which the synthesis of pre-ribosomal RNA by RNA Polymerase I (Pol I) serves as the rate limiting step.

Not surprisingly, Pol I transcription in normal cells is tightly controlled, through the action of multiple tumor suppressor proteins (including p53, pRB and PTEN) which serve as inhibitors. The loss of such control due to mutations in tumor suppressor genes or activation of certain oncogenic pathways, such as cMyc and PI3K/Ak/mTOR, results in the hyperactivation of Pol I transcription that is commonly found in malignancy.

In addition to cancer, hyperactivation of Pol I transcription has been linked to poor prognosis in multiple sclerosis and has been shown to play a role in the infections cycle of certain pathologic viruses, including cytomegalovirus, hepatitis B virus and hepatitis C virus. Therefore, agents that selectively disrupt Pol I transcription are conceptually attractive as anticancer, anti-inflammatory and antiviral therapeutics

SUMMARY OF THE INVENTION

Provided herein are novel compounds and methods of treating or preventing any one of the diseases or conditions described herein comprising administering a therapeutically effective amount of a compound described herein, or a pharmaceutically acceptable salt, or solvate thereof, to a mammal in need thereof. In specific embodiments, the compound inhibits ribosome biogenesis by inhibiting POL1 transcription and the disease or condition is amenable to treatment or prevention by the inhibition of POL1 transcription.

In one aspect, described herein is a method for treating or preventing cancer in a mammal comprising administering a therapeutically effective amount of a compound described herein, or a pharmaceutically acceptable salt, or solvate thereof, to the mammal in need thereof. In another aspect, described herein is a method for treating or preventing an inflammatory disease in a mammal comprising administering a therapeutically effective amount of a compound described herein, or a pharmaceutically acceptable salt, or solvate thereof, to the mammal in need thereof.

In still another aspect, described herein is a method for treating or preventing a proliferative disorder in a mammal comprising administering a therapeutically effective amount of a compound described herein, or a pharmaceutically acceptable salt, or solvate thereof, to the mammal in need thereof. In another aspect, described herein is a method for treating or preventing a disease or disorder in a mammal comprising administering a therapeutically effective amount of a compound described herein, wherein the compound inhibits ribosome biogenesis by inhibiting POL1 transcription.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Compounds

Compounds described herein, including pharmaceutically acceptable salts, prodrugs, active metabolites and pharmaceutically acceptable solvates thereof, inhibit ribosome biogenesis by inhibiting POL1 transcription.

In one aspect, the present invention provides a compound of Formula (I),

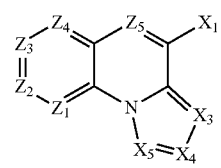

I and pharmaceutically acceptable salts, esters, prodrugs, hydrates and tautomers thereof; wherein:

$Z_5$ is N or $CX_2$;

each $Z_1$, $Z_2$, $Z_3$, and $Z_4$ is N, CH, or $CR_1$, provided any three N are non-adjacent; and further provided that one or more of $Z_1$, $Z_2$, $Z_3$, and $Z_4$ is $CR_1$;

each $R_1$ is independently an optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, or each $R_1$ is independently H, halo, $CF_3$, $OR_2$, $NR_2R_3$, $NR_2OR_3$, $NR_2NR_2R_3$, $SR_2$, $SOR_2$, $SO_2R_2$, $SO_2NR_2R_3$, $NR_2SO_2R_3$, $NR_2CONR_2R_3$, $NR_2COOR_3$, $NR_2COR_3$, CN, $COOR_2$, COOH, $CONR_2R_3$, $OOCR_2$, $COR_2$, or $NO_2$;

Two $R_1$ groups on adjacent atoms may form a carboxylic ring, heterocyclic ring, aryl or heteroaryl, each of which may be optionally substituted and/or fused with a cyclic ring; and wherein $R_2$ and $R_3$ groups on the same atom or on adjacent atoms can be linked to form a 3-8 membered ring, optionally containing one or more N, O or S atoms; and each $R_2$ and $R_3$ groups, and each ring formed by linking $R_2$ and $R_3$ groups together, is optionally substituted with one or more substituents selected from halo, =O, =N—CN, =N—OR', =NR', OR', $N(R)_2$, SR', $SO_2R'$, $SO_2NR'_2$, NR'$SO_2R'$, NR'$CONR'_2$, NR'COOR', NR'COR', CN, COOR', $CON(R')_2$, OOCR', COR', and $NO_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S;

or each $R_1$ is independently —W, -L-W, —X-L-A; wherein X is $NR_6$, O, or S; W is an optionally substituted 4-7 membered azacyclic ring, optionally containing an additional heteroatom selected from N, O and S as a ring member; L is a bond, $C_1$-$C_{10}$ alkylene, $C_1$-$C_{10}$ heteroalkylene, $C_2$-$C_{10}$ alkenylene or $C_2$-$C_{10}$ heteroalkenylene linker, each of which is optionally substituted with one or more substituents selected from the group consisting of halogen, oxo (=O), or $C_1$-$C_6$ alkyl; and A is heterocycloalkyl, heteroaryl or $NR_4R_5$ where $R_4$ and $R_5$ are independently H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, $R_4$ and $R_5$ can be linked to form a 3-8 membered ring, optionally containing one or more N, O or S; and each $R_4$ and $R_5$ groups, and each ring formed by linking $R_4$ and $R_5$ groups together, is optionally substituted with one or more substituents selected from halo, =O, =N—CN, =N—OR=, =NR', OR', $N(R')_2$, SR', $SO_2R'$, $SO_2NR'_2$, NR'$SO_2R'$, NR'$CONR'_2$, NR'COOR', NR'COR', CN, COOR', $CON(R)_2$, OOCR', COR', and $NO_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S;

$R_6$ is H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, $R_6$ can be linked to $R_4$ or $R_5$ to form a 3-8 membered ring; and $R_4$ or $R_5$ is optionally substituted with one or more substituents selected from halo, =O, =N—CN, =N—OR', =NR', OR', $N(R')_2$, SR', $SO_2R'$, $SO_2NR'_2$, NR'$SO_2R'$, NR'$CONR'_2$, NR'COOR', NR'COR', CN, COOR', $CON(R')_2$, OOCR', COR', and $NO_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_6$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S;

$X_1$ is an optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, optionally substituted with one or more halogens, =O, $CF_3$, CN, $OR_7$, $NR_8R_9$, $SR_7$, $SO_2NR_8R_9$, $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, or;

$X_1$ is H, $NR_2R_3$, $SOR_2$, $SO_2R_2$, $SO_2NR_2R_3$, $NR_2SO_2R_3$, $NR_2CONR_2R_3$, $NR_2COOR_3$, $NR_2COR_3$, CN, $COOR_2$, ester bioisostere, COOH, carboxy bioisostere, $CONR_2R_3$, amide bioisostere, $OOCR_2$, $COR_2$, or $NO_2$;

$X_2$ is, H, halogen, $CF_3$, CN, $OR_7$, $NR_8R_9$, $SR_7$, $SO_2NR_8R_9$, $C_1$-$C_{10}$ alkyl, $C_1$-$C_{10}$ heteroalkyl, $C_2$-$C_{10}$ alkenyl, or $C_2$-$C_{10}$ heteroalkenyl, each of which is optionally substituted with one or more halogens, =O, or an optionally substituted 3-7 membered carbocyclic or heterocyclic ring.

each $X_3$, $X_4$ and $X_5$ is N or $CR_{10}$ each $R_{10}$ is independently an optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, or each $R_1$ is independently H, halo, $CF_3$, $OR_2$, $NR_2R_3$, $NR_2OR_3$, $NR_2NR_2R_3$, $SR_2$, $SOR_2$, $SO_2R_2$, $SO_2NR_2R_3$, $NR_2SO_2R_3$, $NR_2CONR_2R_3$, $NR_2COOR_3$, $NR_2COR_3$, CN, $COOR_2$, COOH, $CONR_2R_3$, $OOCR_2$, $COR_2$, or $NO_2$;

and wherein $R_2$ and $R_3$ groups on the same atom or on adjacent atoms can be linked to form a 3-8 membered ring, optionally containing one or more N, O or S atoms; and each $R_2$ and $R_3$ groups, and each ring formed by linking $R_2$ and $R_3$ groups together, is optionally substituted with one or more substituents selected from halo, =O, =N—CN, =N—OR=, =NR', OR', $N(R)_2$, SR', $SO_2R'$, $SO_2NR'_2$, NR'$SO_2R'$, NR'$CONR'_2$, NR'$CO_OR'$, NR'COR', CN, COOR', $_CON(R')_2$, OOCR', COR', and $NO_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S;

Two $R_{10}$ groups on adjacent atoms may form a carboxylic ring, heterocyclic ring, aryl or heteroaryl, each of which is optionally substituted and/or fused with a cyclic ring;

or each $R_{10}$ is independently —W, -L-W, —X-L-A; wherein X is $NR_6$, O, or S; W is an optionally substituted 4-7 membered azacyclic ring, optionally containing an additional heteroatom selected from N, O and S as a ring member; L is a bond, a $C_1$-$C_{10}$ alkylene, $C_1$-$C_{10}$ heteroalkylene, $C_2$-$C_{10}$ alkenylene or $C_2$-$C_{10}$ heteroalkenylene linker, each of which is optionally substituted with one or more substituents selected from the group consisting of halogen, oxo (=O), or $C_1$-$C_6$ alkyl; and A is heterocycloalkyl, heteroaryl or $NR_4R_5$ where $R_4$ and $R_5$ are independently H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group.

In one aspect, the present invention provides a compound of Formula I(A),

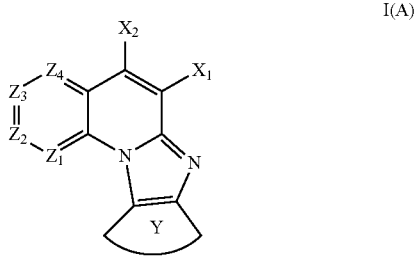

I(A)

and pharmaceutically acceptable salts, esters, prodrugs, hydrates and tautomers thereof; wherein:

Y is an optionally substituted 5-6 membered carbocyclic or heterocyclic ring;

$X_1$ is an optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, optionally substituted with one or more halogens, =O, $CF_3$, CN, $OR_7$, $NR_8R_9$, $SR_7$, $SO_2NR_8R_9$, $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, wherein each $R_7$, $R_8$ and $R_9$ is independently selected from H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, =O, =N—CN, =N—OR=, =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$; wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S; or $X_1$ is H, NR$_2$R$_3$, SOR$_2$, SO$_2$R$_2$, SO$_2$NR$_2$R$_3$, NR$_2$SO$_2$R$_3$, NR$_2$CONR$_2$R$_3$, NR$_2$COOR$_3$, NR$_2$COR$_3$, CN, COOR$_2$, ester bioisostere, COOH, carboxy bioisostere, CONR$_2$R$_3$, amide bioisostere, OOCR$_2$, COR$_2$, or NO$_2$, wherein each R$_2$ and R$_3$ is independently selected from H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein R$_2$ and R$_3$ groups on the same atom or on adjacent atoms can be linked to form a 3-8 membered ring, optionally containing one or more N, O or S atoms; and each R$_2$ and R$_3$ groups, and each ring formed by linking R$_2$ and R$_3$ groups together, is optionally substituted with one or more substituents selected from halo, =O, =N—CN, =N—OR=, =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$; wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S;

$X_2$ is, H, halogen, $CF_3$, CN, $C_1$-$C_{10}$ alkyl, $C_1$-$C_{10}$ heteroalkyl, $C_2$-$C_{10}$ alkenyl, or $C_2$-$C_{10}$ heteroalkenyl, each of which is optionally substituted with one or more halogens, =O, an optionally substituted 3-7 membered carbocyclic or heterocyclic ring, OR$_7$, NR$_8$R$_9$, SR$_7$, or SO$_2$NR$_8$R$_9$; wherein each R$_7$, R$_8$ and R$_9$ is independently selected from H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$; wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S, wherein R$_7$ is not hydrogen when $X_2$ is OR$_7$;

each $Z_1$, $Z_2$, $Z_3$, and $Z_4$ is independently N, CH, or CR$_1$, provided that any three N atoms are non-adjacent; and further provided that one or more of $Z_1$, $Z_2$, $Z_3$, and $Z_4$ is CR$_1$; wherein each R$_1$ is independently an optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group; or each R$_1$ is independently H, halo, $CF_3$, OR$_2$, NR$_2$R$_3$, NR$_2$OR$_3$, NR$_2$NR$_2$R$_3$, SR$_2$, SOR$_2$, SO$_2$R$_2$, SO$_2$NR$_2$R$_3$, NR$_2$SO$_2$R$_3$, NR$_2$CONR$_2$R$_3$, NR$_2$COOR$_3$, NR$_2$COR$_3$, CN, COOR$_2$, COOH, CONR$_2$R$_3$, OOCR$_2$, COR$_2$, or NO$_2$; wherein each R$_2$ and R$_3$ is independently selected from H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein R$_2$ and R$_3$ groups on the same atom or on adjacent atoms can be linked to form a 3-8 membered ring, optionally containing one or more N, O or S atoms; and each $R_2$ and $R_3$ groups, and each ring formed by linking $R_2$ and $R_3$ groups together, is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$; wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S; or each $R_1$ is independently —W, -L-W, —X-L-A; wherein X is $NR_6$, O, or S; wherein $R_6$ is H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group; wherein $R_6$ can be linked to $R_4$ or $R_5$ to form a 3-8 membered ring and $R_4$ and $R_5$ are each independently optionally substituted with one or more substituents selected from halo, =O, =N—CN, =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$; wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S; each W is independently an optionally substituted 4-7 membered azacyclic ring, optionally containing an additional heteroatom selected from N, O and S as a ring member is a bond, $C_1$-$C_{10}$ alkylene, $C_1$-$C_{10}$ heteroalkylene, $C_2$-$C_{10}$ alkenylene or $C_2$-$C_{10}$ heteroalkenylene linker, each of which is optionally substituted with one or more substituents selected from the group consisting of halogen, oxo (=O), or $C_1$-$C_6$ alkyl; and A is heterocycloalkyl, heteroaryl or $NR_4R_5$ wherein $R_4$ and $R_5$ are each independently H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group; wherein $R_4$ and $R_5$ are optionally linked to form a 3-8 membered ring, optionally containing one or more N, O or S; and each $R_4$ and $R_5$ groups, and each ring formed by linking $R_4$ and $R_5$ groups together, is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$; wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

In some embodiments, $X_1$ is CN, COOR$_2$, or CONR$_2$R$_3$.

In some embodiments, X is $NR_6$.

In one aspect, the present invention provides a compound of Formula II(A), II(B), II(C). II(D) and II(E),

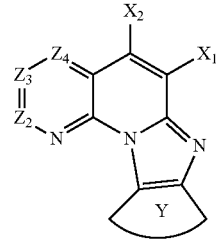

II(A)

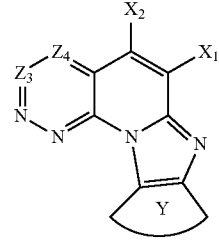

II(B)

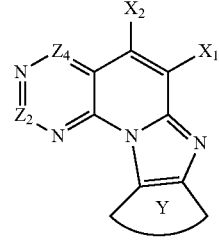

II(C)

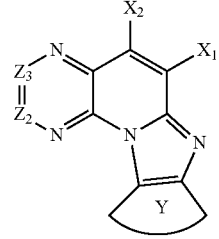

II(D)

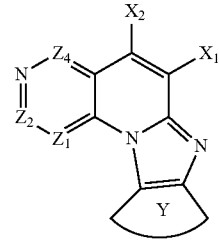

II(E)

or a pharmaceutically acceptable salt or ester thereof.

In some embodiments, $Z_1$, $Z_2$, $Z_3$ and $Z_4$ are independently CH or CR$_1$.

In some embodiments, each $R_1$ is independently an optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, or each $R_1$ is independently halo, $CF_3$, OR$_2$, NR$_2$R$_3$, NR$_2$OR$_3$, NR$_2$NR$_2$R$_3$, SR$_2$, SOR$_2$, SO$_2$R$_2$, $SO_2NR_2R_3$, $NR_2SO_2R_3$, $NR_2CONR_2R_3$, $NR_2COOR_3$, $NR_2COR_3$, CN, $COOR_2$, COOH, $CONR_2R_3$, $OOCR_2$, $COR_2$, or $NO_2$.

In some embodiments, each $R_1$ is independently —W, -L-W, —X-L-A; wherein X is $NR_6$, O, or S; W is an optionally substituted 4-7 membered azacyclic ring, optionally containing an additional heteroatom selected from N, O and S as a ring member; L is a bond, $C_1$-$C_{10}$ alkylene, $C_1$-$C_{10}$ heteroalkylene, $C_2$-$C_{10}$ alkenylene or $C_2$-$C_{10}$ heteroalkenylene linker, each of which is optionally substituted with one or more substituents selected from the group consisting of halogen, oxo (=O), or $C_1$-$C_6$ alkyl; and A is heterocycloalkyl, heteroaryl, quaternary amine or $NR_4R_5$ where $R_4$ and $R_5$ are independently H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group.

In some embodiments, $R_4$ and $R_5$ are linked to form a 3-8 membered ring, optionally containing one or more N, O or S; and each $R_4$ and $R_5$ groups, and each ring formed by linking $R_4$ and $R_5$ groups together, is optionally substituted with one or more substituents selected from halo, =O, =N—CN,=N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

In some embodiments, $R_6$ is H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group; or $R_6$ can be linked to $R_4$ or $R_5$ to form a 3-8 membered ring; and $R_4$ or $R_5$ is optionally substituted with one or more substituents selected from halo, =O, =N—CN,=N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

In some embodiments, Y is an optionally substituted 5-6 membered carbocyclic or heterocyclic ring.

In some embodiments, $X_1$ is an optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, or $X_1$ is H, $NR_2R_3$, $SOR_2$, $SO_2R_2$, $SO_2NR_2R_3$, $NR_2SO_2R_3$, $NR_2CONR_2R_3$, $NR_2COOR_3$, $NR_2COR_3$, CN, $COOR_2$, COOH, polar substituent, carboxy bioisostere, $CONR_2R_3$, $OOCR_2$, $COR_2$, or $NO_2$.

In some embodiments, $X_2$ is H, halogen, $CF_3$, CN, $OR_7$, $NR_8R_9$, $SR_7$, $SO_2NR_8R_9$, $C_1$-$C_{10}$ alkyl, $C_1$-$C_{10}$ heteroalkyl, $C_2$-$C_{10}$ alkenyl, or $C_2$-$C_{10}$ heteroalkenyl, each of which is optionally substituted with one or more halogens, =O, or an optionally substituted 3-7 membered carbocyclic or heterocyclic ring, wherein $R_2$ and $R_3$ groups on the same atom or on adjacent atoms can be linked to form a 3-8 membered ring, optionally containing one or more N, O or S; and each $R_2$ and $R_3$ groups, and each ring formed by linking $R_2$ and $R_3$ groups together, is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S;

In some embodiments, the Compound of Formula (I) has the following structure of Formula III(A), III(B) or III(C):

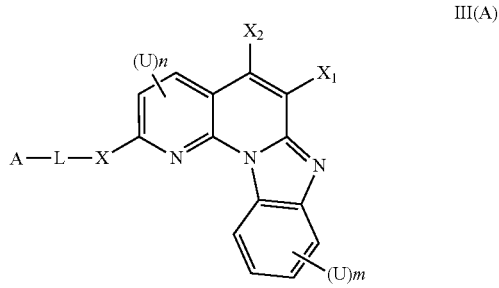

III(A)

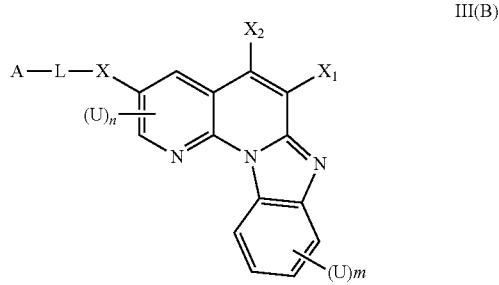

III(B)

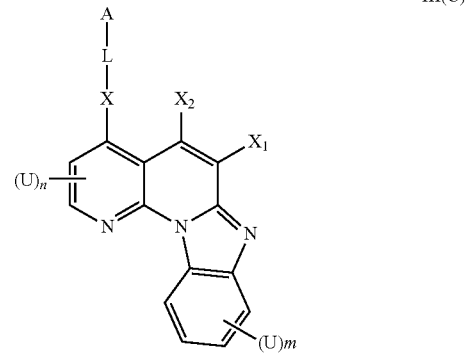

III(C)

or a pharmaceutically acceptable salt or ester thereof.

In some embodiments, L is a bond, $C_1$-$C_{10}$ alkylene, $C_1$-$C_{10}$ heteroalkylene, $C_2$-$C_{10}$ alkenylene or $C_2$-$C_{10}$ heteroalkenylene linker, each of which is optionally substituted with one or more substituents selected from the group consisting of halogen, oxo (=O), or $C_1$-$C_6$ alkyl.

In some embodiments, A is heterocycloalkyl, heteroaryl, quaternary amine or $NR_4R_5$ where $R_4$ and $R_5$ are independently H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group.

In some embodiments, $R_4$ and $R_5$ can be linked to form a 3-8 membered ring, optionally containing one or more N, O or S; and each $R_4$ and $R_5$ groups, and each ring formed by linking $R_4$ and $R_5$ groups together, is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

In some embodiments, X is $NR_6$, O, or S.

In some embodiments, $R_6$ is H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group.

In some embodiments, $R_6$ is linked to $R_4$ or $R_5$ to form a 3-8 membered ring; and $R_4$ or $R_5$ are optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

In some embodiments, $X_1$ is an optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, or $X_1$ is H, $NR_2R_3$, $SOR_2$, $SO_2R_2$, $SO_2NR_2R_3$, $NR_2SO2R_3$, $NR_2CONR_2R_3$, $NR_2COOR_3$, $NR_2COR_3$, CN, $COOR_2$, ester bioisostere, COOH, carboxy bioisostere, $CONR_2R_3$, amide bioisostere, $OOCR_2$, $COR_2$, or $NO_2$.

In some embodiments, $X_2$ is H, halogen, $CF_3$, CN, $OR_7$, $NR_8R_9$, $SR_7$, $SO_2NR_8R_9$, $C_1$-$C_{10}$ alkyl, $C_1$-$C_{10}$ heteroalkyl, $C_2$-$C_{10}$ alkenyl, or $C_2$-$C_{10}$ heteroalkenyl, each of which is optionally substituted with one or more halogens, =O, or an optionally substituted 3-7 membered carbocyclic or heterocyclic ring.

In some embodiments, $(U)_n$ and $(U)_m$ are independently H, halogen, $CF_3$, CN, $OR_7$, $NR_8R_9$, $SR_7$, $SO_2NR_8R_9$, $C_1$-$C_{10}$ alkyl, $C_1$-$C_{10}$ heteroalkyl, $C_2$-$C_{10}$ alkenyl, or $C_2$-$C_{10}$ heteroalkenyl, each of which is optionally substituted with one or more halogens, =O, or an optionally substituted 3-7 membered carbocyclic or heterocyclic ring.

In some embodiments, $R_2$ and $R_3$ groups on the same atom or on adjacent atoms are linked to form a 3-8 membered ring, optionally containing one or more N, O or S; and each $R_2$ and $R_3$ groups, and each ring formed by linking $R_2$ and $R_3$ groups together, is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

In some preferred embodiments, $X_2$ is H and $X_1$ is $CONR_2R_3$, wherein $R_2$ and $R_3$ are independently selected from H, $C_1$-$C_{10}$ alkly, $C_1$-$C_{10}$ heteroalkyl, $C_2$-$C_{10}$ alkenyl, and $C_2$-$C_{10}$ heteralkenyl, each of which is optionally substituted with one or more halogens, =O, or an optionally substituted 3-7 membered carbocyclic or heterocyclic ring.

In one aspect, the present invention provides a compound of Formula IV(A), IV(B) and IV(C),

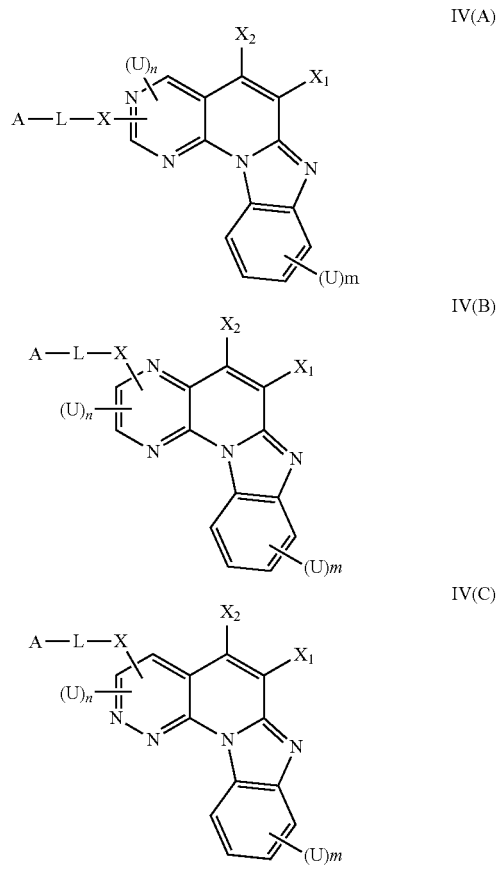

and pharmaceutically acceptable salts, esters, prodrugs, hydrates and tautomers thereof; wherein:

L is a bond, $C_1$-$C_{10}$ alkylene, $C_1$-$C_{10}$ heteroalkylene, $C_2$-$C_{10}$ alkenylene or $C_2$-$C_{10}$ heteroalkenylene linker, each of which is optionally substituted with one or more substituents selected from the group consisting of halogen, oxo (=O), or $C_1$-$C_6$ alkyl;

A is heterocycloalkyl, heteroaryl or $NR_4R_5$ where $R_4$ and $R_5$ are independently H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, $R_4$ and $R_5$ can be linked to form a 3-8 membered ring, optionally containing one or more N, O or S; and each $R_4$ and $R_5$ groups, and each ring formed by linking $R_4$ and $R_5$ groups together, is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S;

X is $NR_6$, O, or S;

$R_6$ is H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group;

$R_6$ can be linked to $R_4$ or $R_5$ to form a 3-8 membered ring; and $R_4$ or $R_5$ is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S;

$X_1$ is an optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, or $X_1$ is H, $NR_2R_3$, $SOR_2$, $SO_2R_2$, $SO_2NR_2R_3$, $NR_2SO_2R_3$, $NR_2CONR_2R_3$, $NR_2COOR_3$, $NR_2COR_3$, CN, $COOR_2$, ester bioisostere, COOH, carboxy bioisostere, $CONR_2R_3$, amide bioisostere, $OOCR_2$, $COR_2$, or $NO_2$;

$X_2$ is H, halogen, $CF_3$, CN, $OR_7$, $NR_8R_9$, $SR_7$, $SO_2NR_8R_9$, $C_1$-$C_{10}$ alkyl, $C_1$-$C_{10}$ heteroalkyl, $C_2$-$C_{10}$ alkenyl, or $C_2$-$C_{10}$ heteroalkenyl, each of which is optionally substituted with one or more halogens, =O, or an optionally substituted 3-7 membered carbocyclic or heterocyclic ring;

$(U)_n$ and $(U)_m$ are independently H, halogen, $CF_3$, CN, $OR_7$, $NR_8R_9$, $SR_7$, $SO_2NR_8R_9$, $C_1$-$C_{10}$ alkyl, $C_1$-$C_{10}$ heteroalkyl, $C_2$-$C_{10}$ alkenyl, or $C_2$-$C_{10}$ heteroalkenyl, each of which is optionally substituted with one or more halogens, =O, or an optionally substituted 3-7 membered carbocyclic or heterocyclic ring;

wherein $R_2$ and $R_3$ groups on the same atom or on adjacent atoms can be linked to form a 3-8 membered ring, optionally containing one or more N, O or S; and each $R_2$ and $R_3$ groups, and each ring formed by linking $R_2$ and $R_3$ groups together, is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

In one aspect, the present invention provides a compound of Formula V(A), V(B), V(C) and V(D),

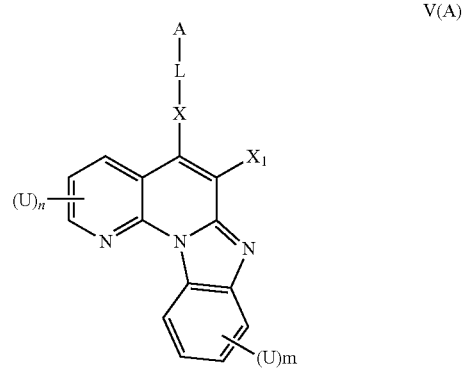

V(A)

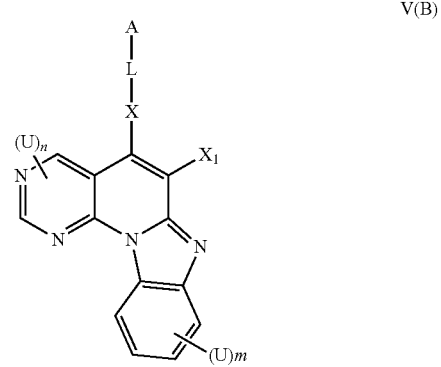

V(B)

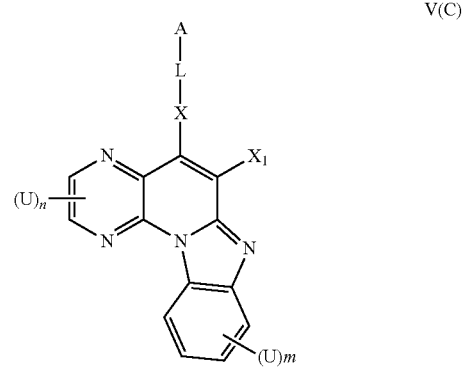

V(C)

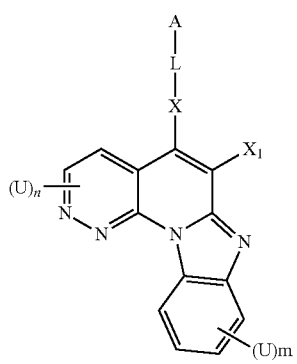

V(D)

and pharmaceutically acceptable salts, esters, prodrugs, hydrates and tautomers thereof; wherein:

L is a bond, $C_1$-$C_{10}$ alkylene, $C_1$-$C_{10}$ heteroalkylene, $C_2$-$C_{10}$ alkenylene or $C_2$-$C_{10}$ heteroalkenylene linker, each of which is optionally substituted with one or more substituents selected from the group consisting of halogen, oxo (=O), or $C_1$-$C_6$ alkyl;

A is heterocycloalkyl, heteroaryl or $NR_4R_5$ where $R_4$ and $R_5$ are independently H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, $R_4$ and $R_5$ can be linked to form a 3-8 membered ring, optionally containing one or more N, O or S; and each $R_4$ and $R_5$ groups, and each ring formed by linking $R_4$ and $R_5$ groups together, is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S;

X is $NR_6$, O, or S;

$R_6$ is H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group;

$R_6$ can be linked to $R_4$ or $R_5$ to form a 3-8 membered ring; and $R_4$ or $R_5$ is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S;

$X_1$ is an optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, or $X_1$ is H, NR$_2$R$_3$, SOR$_2$, SO$_2$R$_2$, SO$_2$NR$_2$R$_3$, NR$_2$SO$_2$R$_3$, NR$_2$CONR$_2$R$_3$, NR$_2$COOR$_3$, NR$_2$COR$_3$, CN, COOR$_2$, ester bioisostere, COOH, carboxy bioisostere, CONR$_2$R$_3$, amide bioisostere, OOCR$_2$, COR$_2$, or NO$_2$;

(U)$_n$ and (U)$_m$ are independently H, halogen, CF$_3$, CN, OR$_7$, NR$_8$R$_9$, SR$_7$, SO$_2$NR$_8$R$_9$, $C_1$-$C_{10}$ alkyl, $C_1$-$C_{10}$ heteroalkyl, $C_2$-$C_{10}$ alkenyl, or $C_2$-$C_{10}$ heteroalkenyl, each of which is optionally substituted with one or more halogens, =O, or an optionally substituted 3-7 membered carbocyclic or heterocyclic ring;

wherein $R_2$ and $R_3$ groups on the same atom or on adjacent atoms can be linked to form a 3-8 membered ring, optionally containing one or more N, O or S; and each $R_2$ and $R_3$ groups, and each ring formed by linking $R_2$ and $R_3$ groups together, is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

In some embodiments, the Compound of Formula (I) has the following structure of Formula VI:

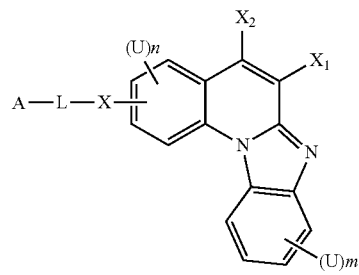

VI or a pharmaceutically acceptable salt or ester thereof.

In some embodiments, L is a bond, $C_1$-$C_{10}$ alkylene, $C_1$-$C_{10}$ heteroalkylene, $C_2$-$C_{10}$ alkenylene or $C_2$-$C_{10}$ heteroalkenylene linker, each of which is optionally substituted with one or more substituents selected from the group consisting of halogen, oxo (=O), or $C_1$-$C_6$ alkyl.

In some embodiments, A is heterocycloalkyl, heteroaryl, quaternary amine or NR$_4$R$_5$ wherein R$_4$ and R$_5$ are independently H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, or R$_4$ and R$_5$ can be linked to form a 3-8 membered ring, optionally containing one or more N, O or S; and each R$_4$ and R$_5$ groups, and each ring formed by linking R$_4$ and R$_5$ groups together, is optionally substituted with one or more substituents selected from halo, =O, =N—CN, =N—OR', =NR', OR', N(R')$_2$, SR', SO$_2$R', $SO_2NR'_2$, $NR'SO_2R'$, $NR'CONR'_2$, $NR'COOR'$, $NR'COR'$, CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

In some embodiments, X is NR$_6$, O, or S; wherein R$_6$ is H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group; or R$_6$ can be linked to R$_4$ or R$_5$ to form a 3-8 membered ring.

In some embodiments, X$_1$ is an optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, or X$_1$ is H, NR$_2$R$_3$, SOR$_2$, SO$_2$R$_2$, SO$_2$NR$_2$R$_3$, NR$_2$SO$_2$R$_3$, NR$_2$CONR$_2$R$_3$, NR$_2$COOR$_3$, NR$_2$COR$_3$, CN, COOR$_2$, ester bioisostere, COOH, carboxy bioisostere, CONR$_2$R$_3$, amide bioisostere, OOCR$_2$, COR$_2$, or NO$_2$, wherein R$_2$ and R$_3$ groups on the same atom or on adjacent atoms can be linked to form a 3-8 membered ring, optionally containing one or more N, O or S; and each R$_2$ and R$_3$ groups, and each ring formed by linking R$_2$ and R$_3$ groups together, is optionally substituted with one or more substituents selected from halo, =O, =N—CN, =N—OR', =NR', OR', N(R')$_2$, SR', SO$_2$R', SO$_2$NR'2, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

In some embodiments, X$_2$ is H, halogen, CF$_3$, CN, OR$_7$, NR$_8$R$_9$, SR$_7$, SO$_2$NR$_8$R$_9$, $C_1$-$C_{10}$ alkyl, $C_1$-$C_{10}$ heteroalkyl, $C_2$-$C_{10}$ alkenyl, or $C_2$-$C_{10}$ heteroalkenyl, each of which is optionally substituted with one or more halogens, =O, or an optionally substituted 3-7 membered carbocyclic or heterocyclic ring.

In some embodiments, (U)$_n$ and (U)$_m$ are independently H, halogen, CF$_3$, CN, OR$_7$, NR$_8$R$_9$, SR$_7$, SO$_2$NR$_8$R$_9$, $C_1$-$C_{10}$ alkyl, $C_1$-$C_{10}$ heteroalkyl, $C_2$-$C_{10}$ alkenyl, or $C_2$-$C_{10}$ heteroalkenyl, each of which is optionally substituted with one or more halogens, =O, or an optionally substituted 3-7 membered carbocyclic or heterocyclic ring.

In one aspect, the present invention provides a compound of Formula VII(A) and VII(B),

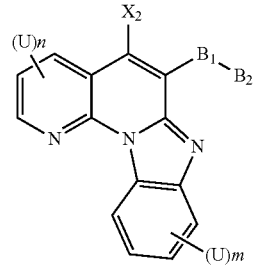

VII(A)

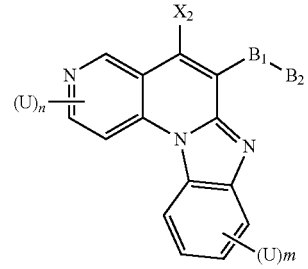

VII(B)

and pharmaceutically acceptable salts, esters, prodrugs, hydrates and tautomers thereof; wherein:

B$_1$ is a bond or C=O, B$_2$ is X-L-A

L is a bond, $C_1$-$C_{10}$ alkylene, $C_1$-$C_{10}$ heteroalkylene, $C_2$-$C_{10}$ alkenylene or $C_2$-$C_{10}$ heteroalkenylene linker, each of which is optionally substituted with one or more substituents selected from the group consisting of halogen, oxo (=O), or $C_1$-$C_6$ alkyl;

A is heterocycloalkyl, heteroaryl or NR$_4$R$_5$ wherein R$_4$ and R$_5$ are independently H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, or R$_4$ and R$_5$ can be linked to form a 3-8 membered ring, optionally containing one or more N, O or S; and each R$_4$ and R$_5$ groups, and each ring formed by linking R$_4$ and R$_5$ groups together, is optionally substituted with one or more substituents selected from halo, =O, =N—CN, =N—OR', =NR', OR', N(R')$_2$, SR', SO$_2$R', SO$_2$NR'2, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S;

X is CR$_6$R$_6$, NR$_6$, O, or S; wherein R$_6$ is H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group; or R$_6$ can be linked to R$_4$ or R$_5$ to form a 3-8 membered ring;

X$_2$ is H, halogen, CF$_3$, CN, OR$_7$, NR$_8$R$_9$, SR$_7$, SO$_2$NR$_8$R$_9$, $C_1$-$C_{10}$ alkyl, $C_1$-$C_{10}$ heteroalkyl, $C_2$-$C_{10}$ alkenyl, or $C_2$-$C_{10}$ heteroalkenyl, each of which is optionally substituted with one or more halogens, =O, or an optionally substituted 3-7 membered carbocyclic or heterocyclic ring.

$(U)_n$ and $(U)_m$ are independently H, halogen, $CF_3$, CN, $OR_7$, $NR_8R_9$, $SR_7$, $SO_2NR_8R_9$, $C_1$-$C_{10}$ alkyl, $C_1$-$C_{10}$ heteroalkyl, $C_2$-$C_{10}$ alkenyl, or $C_2$-$C_{10}$ heteroalkenyl, each of which is optionally substituted with one or more halogens, =O, or an optionally substituted 3-7 membered carbocyclic or heterocyclic ring.

In one aspect, the present invention provides a compound of Formula VIII(A), VIII(B) and VIII(C),

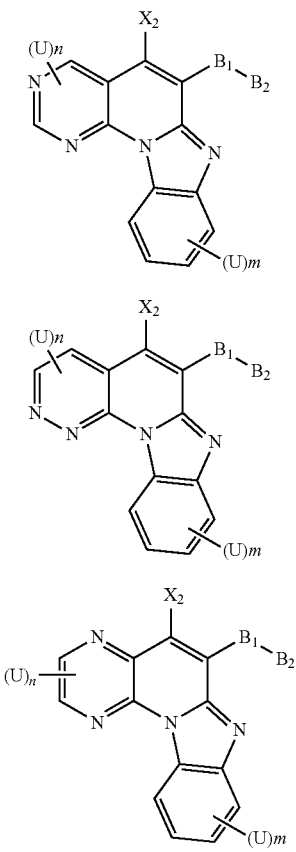

VIII(A)

VIII(B)

VIII(C)

and pharmaceutically acceptable salts, esters, prodrugs, hydrates and tautomers thereof; wherein:

$B_1$ is a bond or C=O, $B_2$ is X-L-A

L is a bond, $C_1$-$C_{10}$ alkylene, $C_1$-$C_{10}$ heteroalkylene, $C_2$-$C_{10}$ alkenylene or $C_2$-$C_{10}$ heteroalkenylene linker, each of which is optionally substituted with one or more substituents selected from the group consisting of halogen, oxo (=O), or $C_1$-$C_6$ alkyl;

A is heterocycloalkyl, heteroaryl or $NR_4R_5$ wherein $R_4$ and $R_5$ are independently H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, or $R_4$ and $R_5$ can be linked to form a 3-8 membered ring, optionally containing one or more N, O or S; and each $R_4$ and $R_5$ groups, and each ring formed by linking $R_4$ and $R_5$ groups together, is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S;

X is $CR_6R_6NR_6$, O, or S; wherein $R_6$ is H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group; or $R_6$ can be linked to $R_4$ or $R_5$ to form a 3-8 membered ring;

$X_2$ is H, halogen, $CF_3$, CN, $OR_7$, $NR_8R_9$, $SR_7$, $SO_2NR_8R_9$, $C_1$-$C_{10}$ alkyl, $C_1$-$C_{10}$ heteroalkyl, $C_2$-$C_{10}$ alkenyl, or $C_2$-$C_{10}$ heteroalkenyl, each of which is optionally substituted with one or more halogens, =O, or an optionally substituted 3-7 membered carbocyclic or heterocyclic ring.

$(U)_n$ and $(U)_m$ are independently H, halogen, $CF_3$, CN, $OR_7$, $NR_8R_9$, $SR_7$, $SO_2NR_8R_9$, $C_1$-$C_{10}$ alkyl, $C_1$-$C_{10}$ heteroalkyl, $C_2$-$C_{10}$ alkenyl, or $C_2$-$C_{10}$ heteroalkenyl, each of which is optionally substituted with one or more halogens, =O, or an optionally substituted 3-7 membered carbocyclic or heterocyclic ring.

Any combination of the groups described above for the various variables is contemplated herein. Throughout the specification, groups and substituents thereof are chosen by one skilled in the field to provide stable moieties and compounds.

In one aspect, described herein are pharmaceutical compositions comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is in the form of a tablet, a pill, a capsule, a liquid, a suspension, a gel, a dispersion, a solution, an emulsion, an ointment, or a lotion.

In one aspect, described herein is a method of treating or preventing any one of the diseases or conditions described herein comprising administering a therapeutically effective amount of a compound described herein, or a pharmaceutically acceptable salt, or solvate thereof, to a mammal in need thereof.

In another aspect, described herein is a method for treating or preventing cancer, or fibrosis, or combinations thereof in a mammal comprising administering a therapeutically effective amount of a compound described herein, or a pharmaceutically acceptable salt, or solvate thereof, to the mammal in need thereof.

In one aspect, described herein is a method for treating or preventing cancer in a mammal comprising administering a therapeutically effective amount of a compound described herein, or a pharmaceutically acceptable salt, or solvate thereof, to the mammal in need thereof. In some embodiments, the cancer is amenable to treatment with an inhibitor of POL1 transcription. In some embodiments, the method further comprises administering a second therapeutic agent to the mammal in addition to the compound described herein, or a pharmaceutically acceptable salt, or solvate thereof.

In one aspect, described herein is a method for treating or preventing an inflammatory disease in a mammal comprising administering a therapeutically effective amount of a compound described herein, or a pharmaceutically acceptable salt, or solvate thereof, to the mammal in need thereof. In some embodiments, the inflammatory disease is amenable to treatment with an inhibitor of POL1 transcription. In some embodiments, the method further comprises administering a second therapeutic agent to the mammal in addition to the compound described herein, or a pharmaceutically acceptable salt, or solvate thereof.

In one aspect, described herein is a method for treating or preventing a proliferative disorder in a mammal comprising administering a therapeutically effective amount of a compound described herein, or a pharmaceutically acceptable salt, or solvate thereof, to the mammal in need thereof. In some embodiments, the proliferative disorder is amenable to treatment with an inhibitor of POL1 transcription. In some embodiments, the method further comprises administering a second therapeutic agent to the mammal in addition to the compound described herein, or a pharmaceutically acceptable salt, or solvate thereof.

In one aspect, described herein is a method for treating or preventing a disease or disorder in a mammal comprising administering a therapeutically effective amount of a compound described herein, wherein the compound inhibits ribosome biogenesis by inhibiting POL1 transcription. In some embodiments, the method further comprises administering a second therapeutic agent to the mammal in addition to the compound described herein, or a pharmaceutically acceptable salt, or solvate thereof.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by inhalation; and/or (e) t administered by nasal administration; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the aforementioned aspects involving the treatment of POL1 transcription related diseases or conditions are further embodiments comprising administering at least one additional agent in addition to the administration of a compound described herein, or a pharmaceutically acceptable salt thereof. In various embodiments, each agent is administered in any order, including simultaneously.

In any of the embodiments disclosed herein, the mammal is a human.

In some embodiments, compounds provided herein are administered to a human.

In some embodiments, compounds provided herein are orally administered.

Articles of manufacture, which include packaging material, a compound described herein, or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for inhibiting ribosome biogenesis by inhibiting POL1 transcription, or for the treatment, prevention or amelioration of one or more symptoms of a disease or condition that would benefit from inhibition of POL1 transcription, are provided.

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound described herein with an acid. In some embodiments, the compound described herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1, 5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluene-sulfonic acid (p); and undecylenic acid.

In some embodiments, a compound described herein is prepared as a chloride salt, sulfate salt, bromide salt, mesylate salt, maleate salt, citrate salt or phosphate salt. In some embodiments, a compound described herein is prepared as a hydrochloride salt.

In some embodiments, pharmaceutically acceptable salts are obtained by reacting a compound described herein with a base. In some embodiments, the compound described herein is acidic and is reacted with a base. In such situations, an acidic proton of the compound described herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, di cyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt. In some embodiments, the compounds provided herein are prepared as a sodium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of compounds described herein, as well as active metabolites of these compounds having the same type of activity.

In some embodiments, sites on the organic radicals (e.g. alkyl groups, aromatic rings) of compounds described herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the compounds described herein possess one or more stereocenters and each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of steroisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. For example, see Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference.

In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound described herein as set forth herein are included within the scope of the claims. In some cases, some of the herein-described compounds are a prodrug for another derivative or active compound.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Synthesis of Compounds

Compounds described herein are synthesized using standard synthetic techniques or using methods know in the art in combination with method described herein.

General synthetic method for preparing intermediates and compounds described herein is shown in Scheme 1.

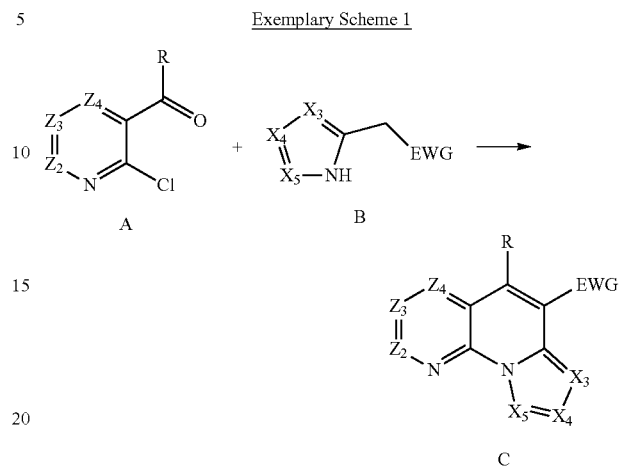

Compounds of formula C are formed by reacting compounds of formula A with compound of formula B under known condensation conditions (See, e.g., Eur. J. Org. Chem., 2004, 546-551, J. Org. Chem., 2006, 71, 5440-5447, Synthesis, 2003, 555-559, Eur. J. Org. Chem., 2006, 3767-3770, Org. Lett., 2013, 15, 1854-1857, 1 Org. Chem., 2007, 72, 9854-9856, Synlett, 2011, 1723-1726, Org. Lett., 2013, 15, 4564-4567, Eur. J. Org. Chem., 2006, 3767-3770).

In certains instances the reaction of compounds A and compounds B lead in one step to compounds C. In other instances two steps are needed to form compounds C from compounds A and B. First step is the formation of the condensation products followed by nucleophilic reaction under appropriate conditions.

Another general synthetic method for preparing starting materials described herein is shown in Exemplary Scheme 2.

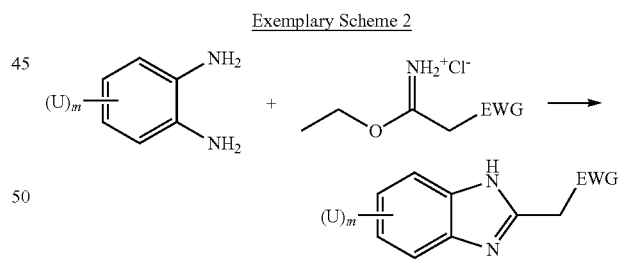

Exemplary starting materials useful in Exemplary Scheme 2 include:

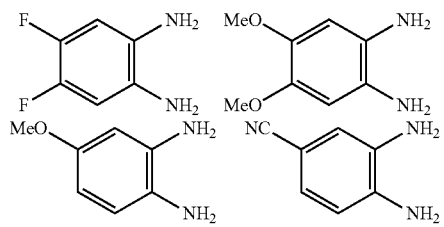

27

-continued

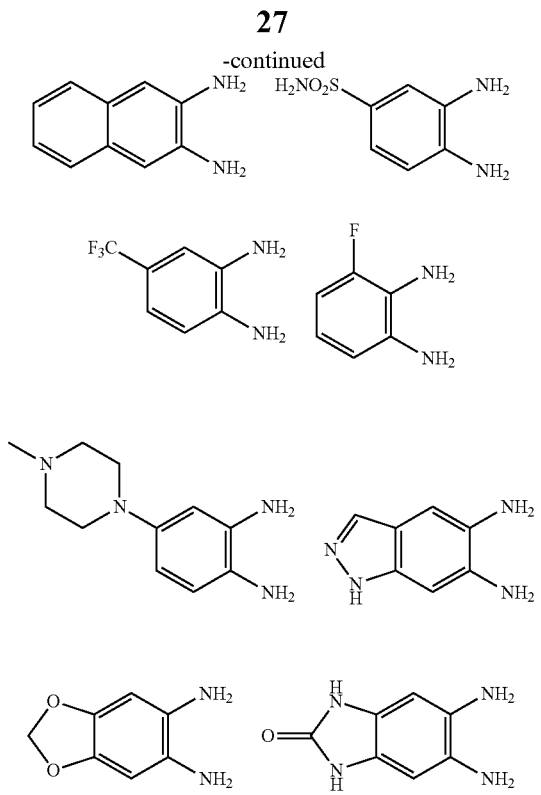

28

-continued

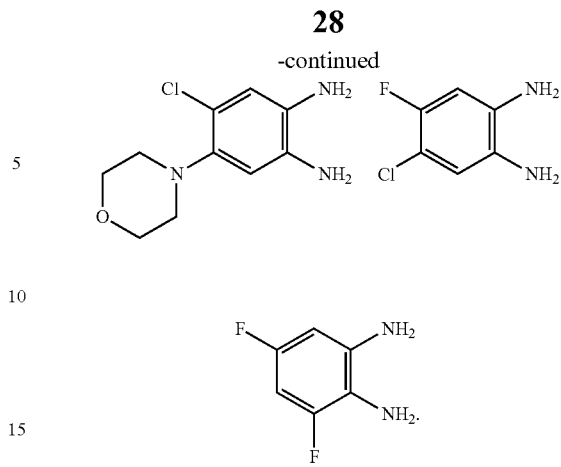

As used herein, "EWG" refers to an electron withdrawing group. As understood in the art, an electron withdrawing group is an atom or group that draws electron density from neighboring atoms towards itself, usually by resonance or inductive effects.

In some embodiments, the preparation of the compounds is made with the sequence of steps shown in Exemplary Scheme 3.

Exemplary Scheme 3

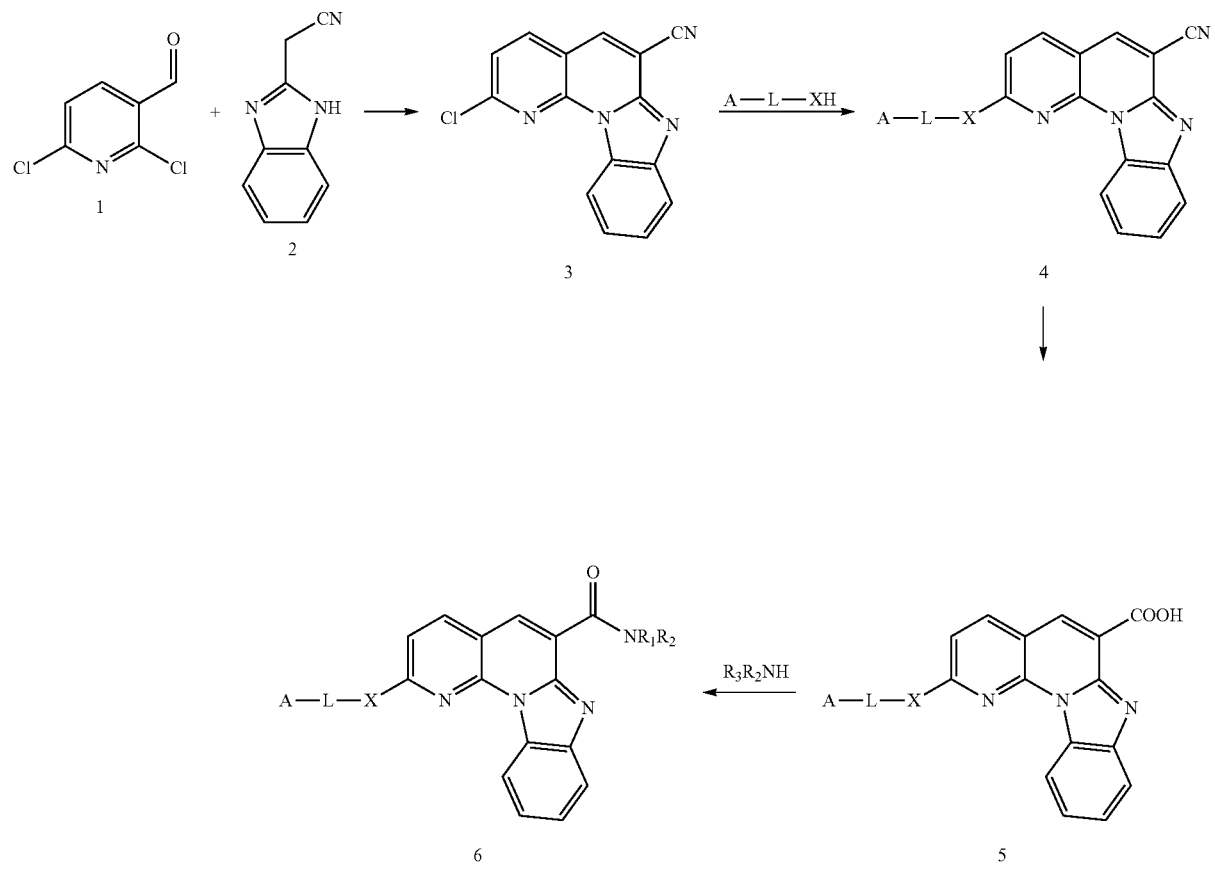

Compound 3 is prepared from the reaction of reagents 1 and 2 using knoevenagel condensation. Compound 4 is prepared by reacting Compound 3 with reagent A-L-XH. The formation Compound 5 from Compound 4 is known in the art. Compound 6 is prepared by the coupling reaction of acid 5 and amines.

In some embodiments, the preparation of the compounds is made with the sequence of steps shown in Exemplary Scheme 4.

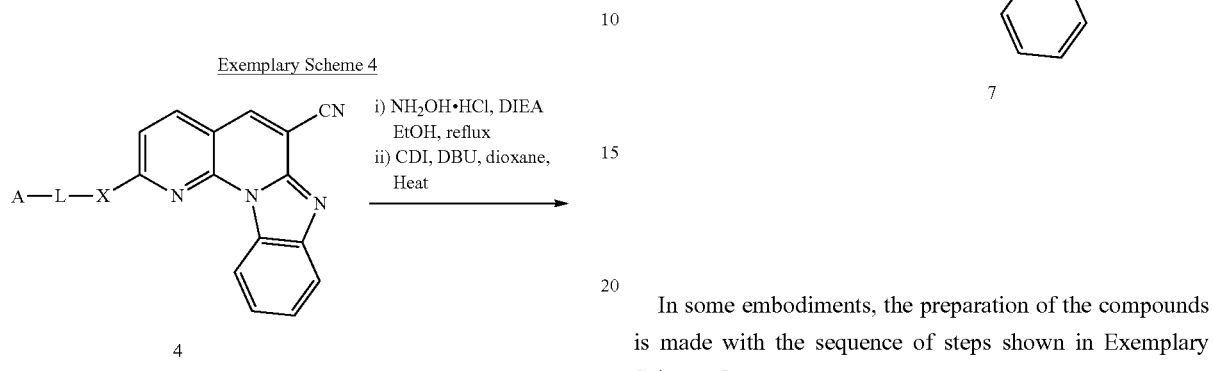

In some embodiments, the preparation of the compounds is made with the sequence of steps shown in Exemplary Scheme 5.

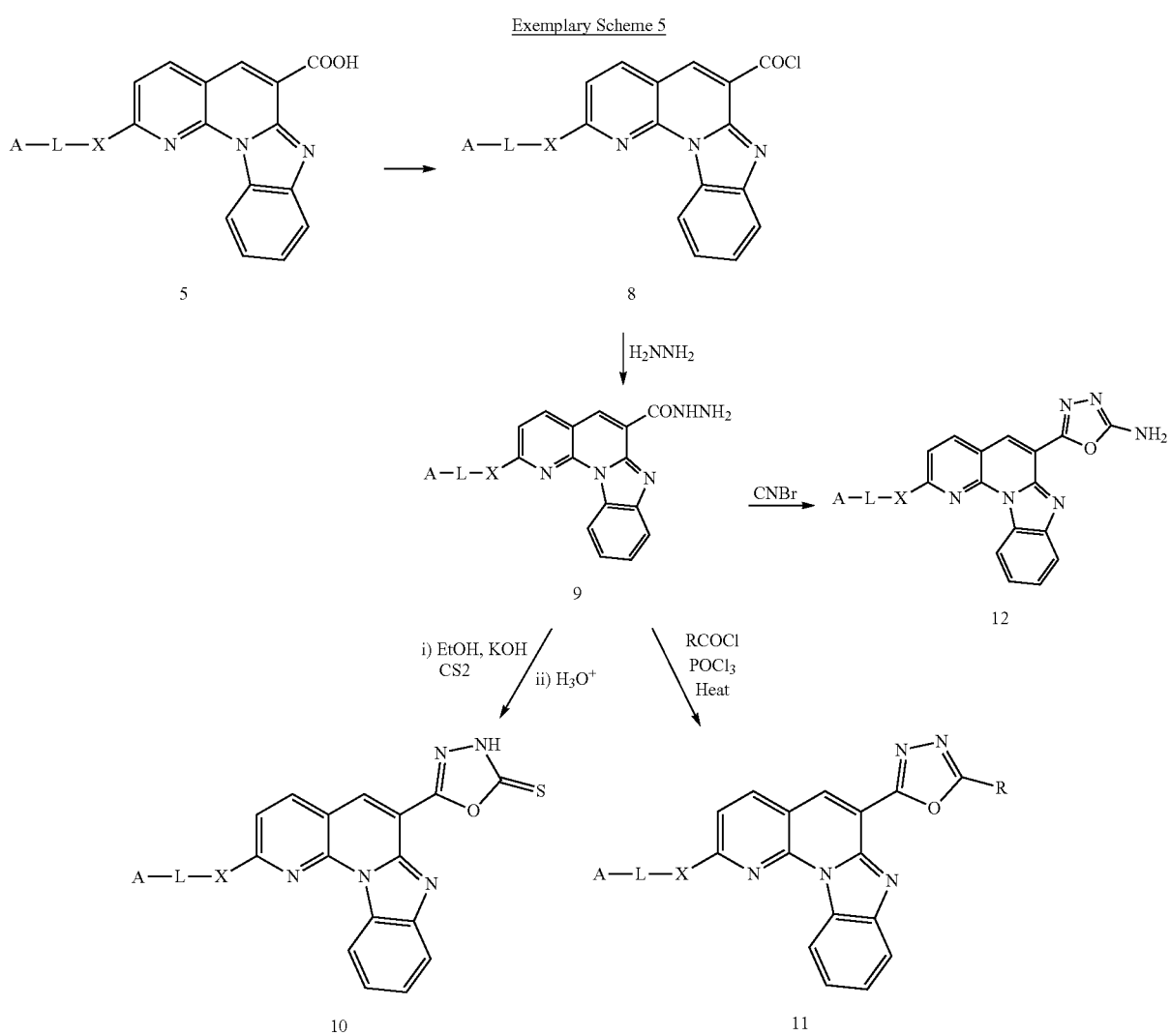

In some embodiments, the preparation of the compounds is made with the sequence of steps shown in Exemplary Scheme 6.
Exemplary Scheme 6
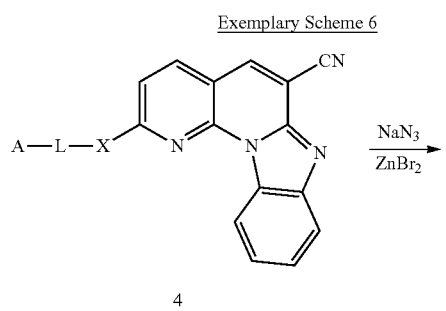
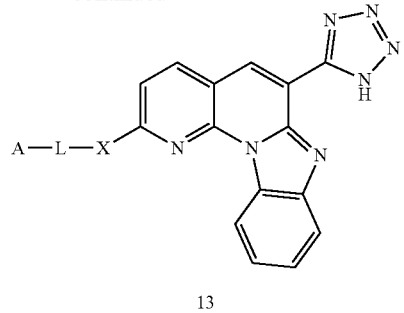
In some embodiments, the preparation of the compounds is made with the sequence of steps shown in Exemplary Scheme 7.
Exemplary Scheme 7
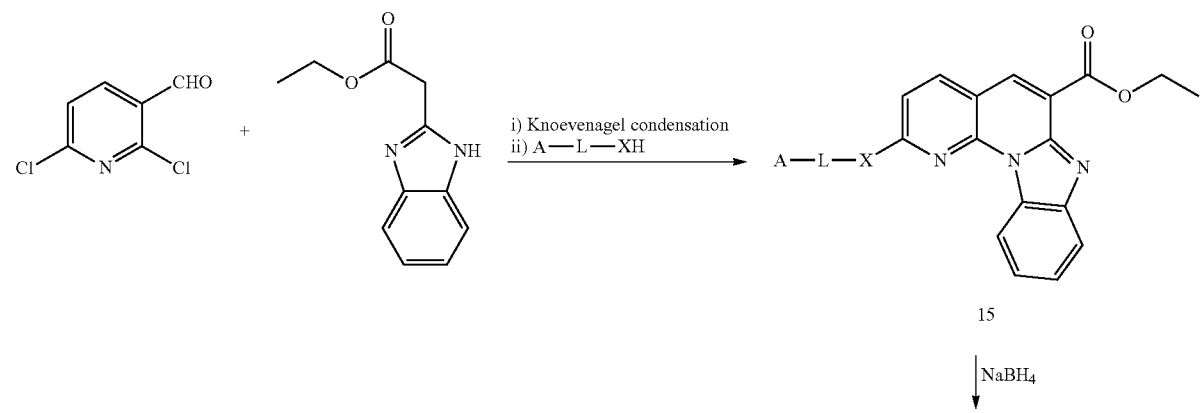
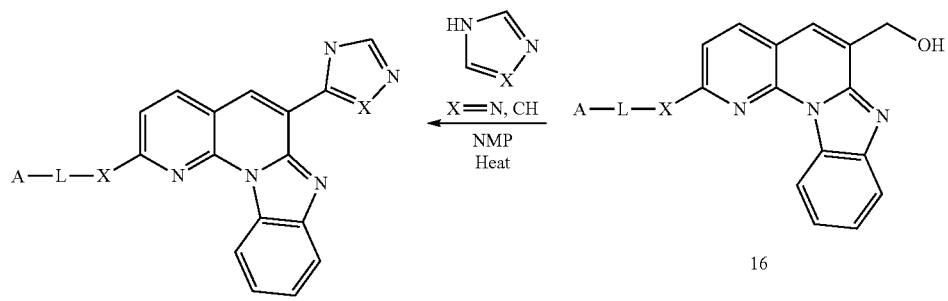

In some embodiments, the preparation of the compounds is made with the sequence of steps shown in Exemplary Scheme 8.

Exemplary Scheme 8

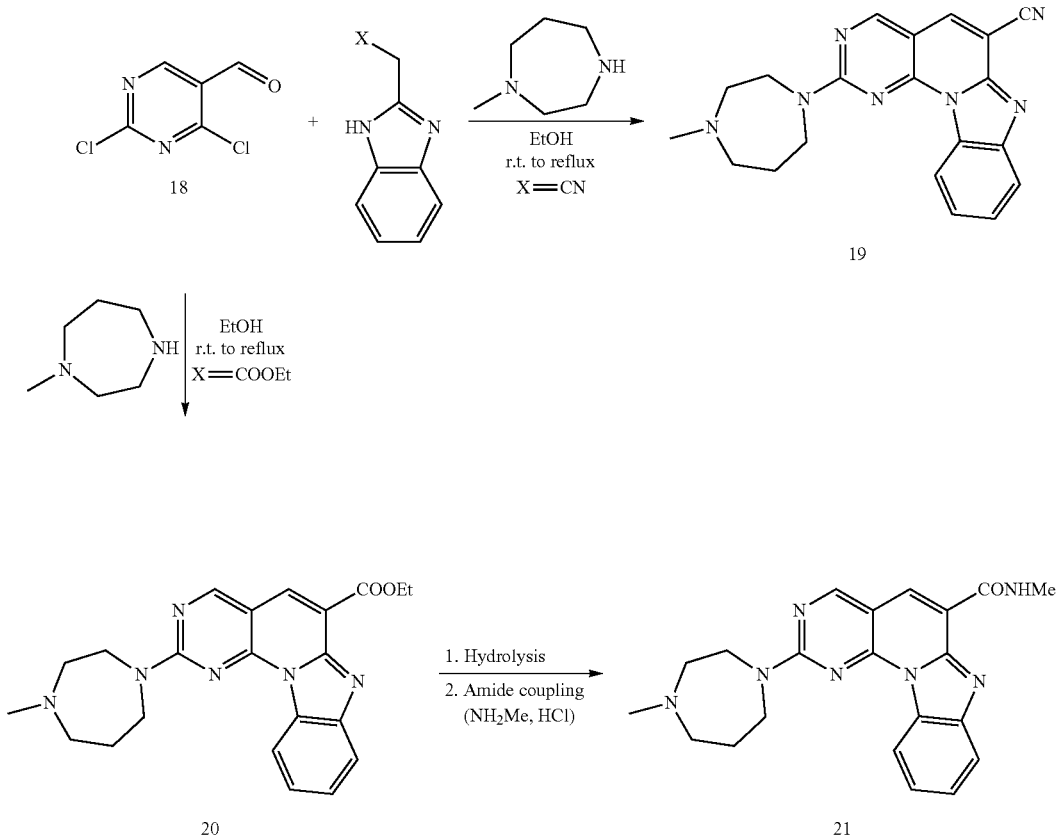

The aldehyde 18 (prepared, for example, according to U.S. Pat. No. 8,637,529 or 7,998,978) is reacted with 2,6-dichloropyridine-3-carboxyaldehyde and N-methylhomopiperazine in ethanol to give compound 19. Alternatively, the reaction of aldehyde 18 with ethyl benzimidazole-2-acetate and N-methylhomopiperazine in ethanol gives compound 20.

The ester group in compound 20 can be hydrolyzed under acidic or basic conditions to form the acid analog which can be coupled to an amine, for example methyl amine, under normal amide coupling to give compound 21.

In some embodiments, the preparation of the compounds is made with the sequence of steps shown in Exemplary Scheme 9.

Exemplary Scheme 9

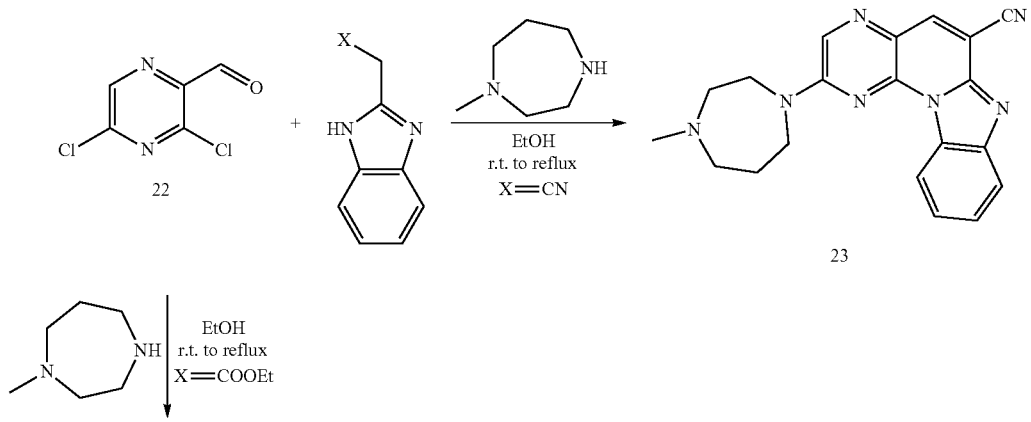

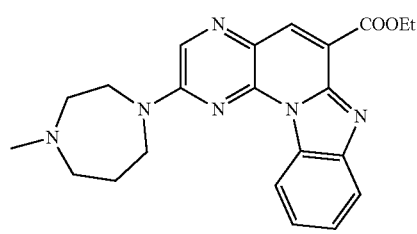

24

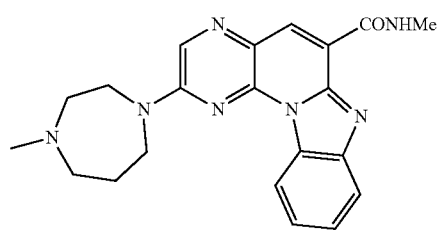

25

The aldehyde 22 (prepared according to U.S. Pat. No. 8,518,952) is reacted with 2,6-dichloropyridine-3-carboxy-aldehyde and N-methylhomopiperazine in ethanol to give compound 23. Alternatively, the reaction of aldehyde 22 with ethyl benzimidazole-2-acetate and N-methylhomopiperazine in ethanol gives compound 24.

The ester group in compound 20 can be hydrolyzed under acidic or basic conditions to form the acid analog which can be coupled to an amine, for example methyl amine, under normal amide coupling conditions to give compound 25.

In some embodiments, the preparation of the compounds is made with the sequence of steps shown in Exemplary Scheme 10.

Exemplary Scheme 10

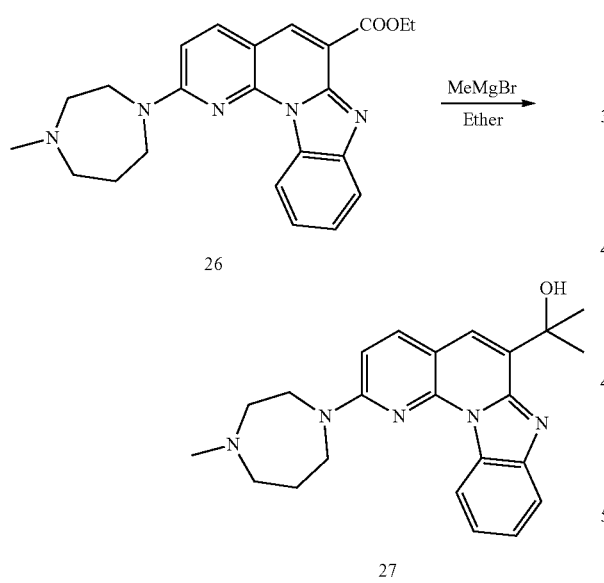

Non-limiting specific examples of A-L-XH in the compounds described herein are illustrated in FIG. 1.

FIG. 1

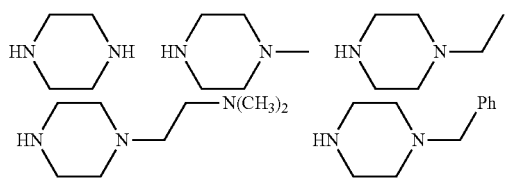

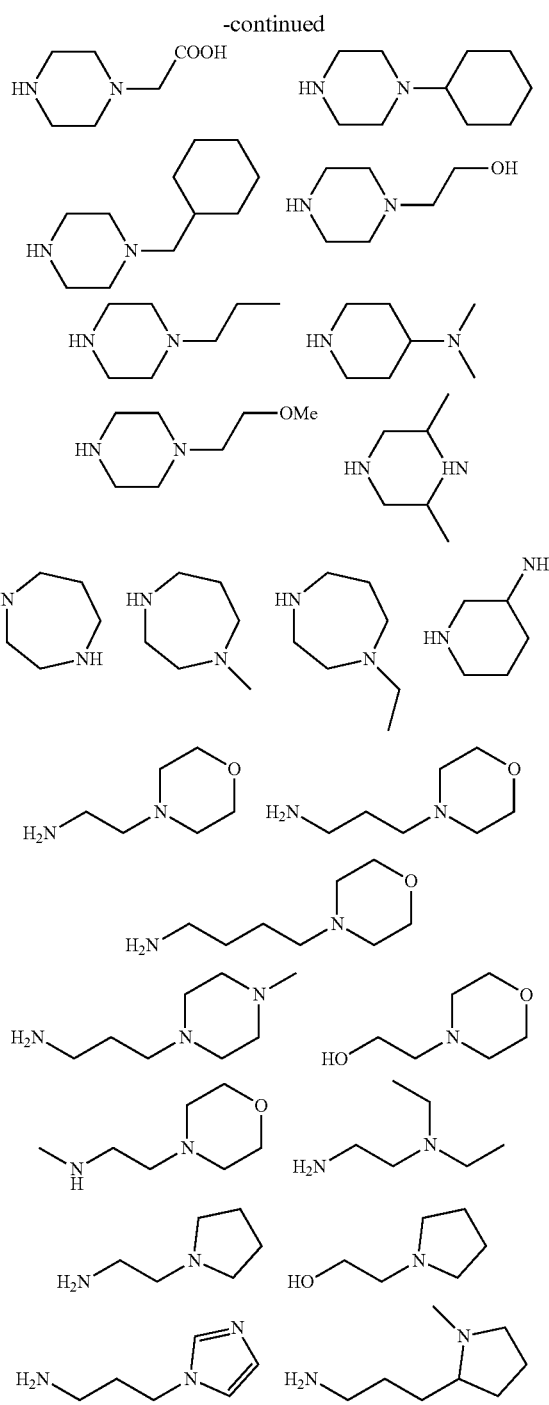

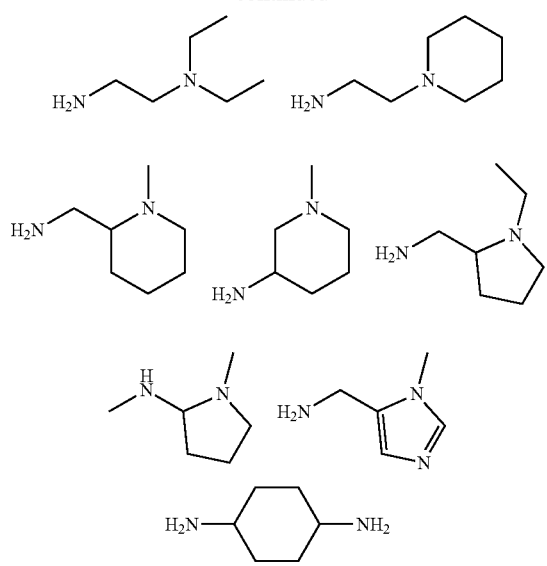
Non-limiting specific examples of R$_3$R$_2$NH in the compounds described herein are illustrated in FIG. 2.
FIG. 2
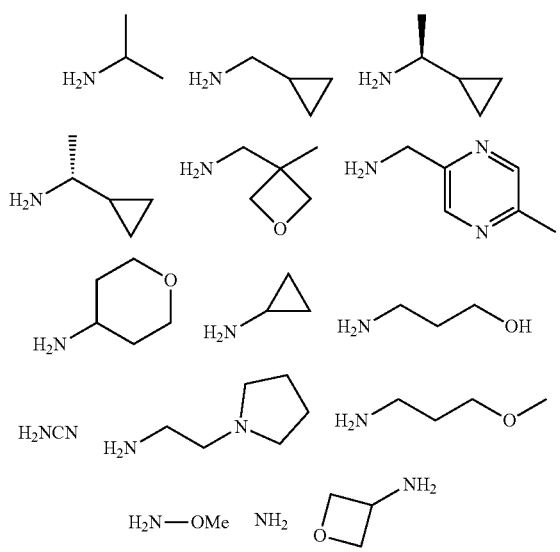
Non-limiting specific examples of compounds of Formula II(C) as described herein are illustrated in FIG. 3.
FIG. 3
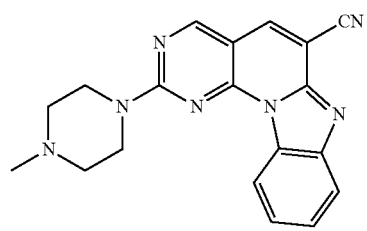
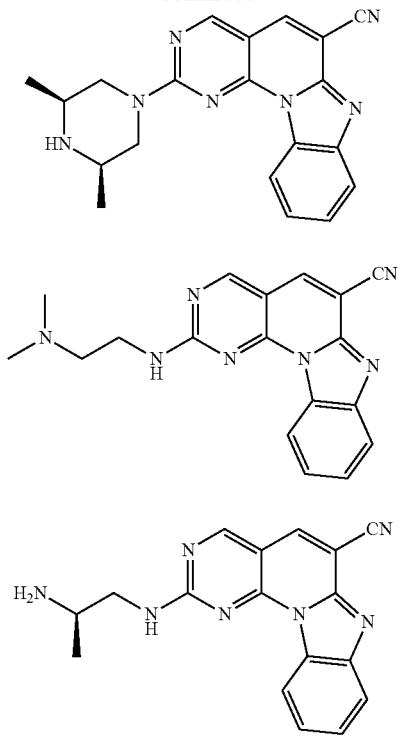

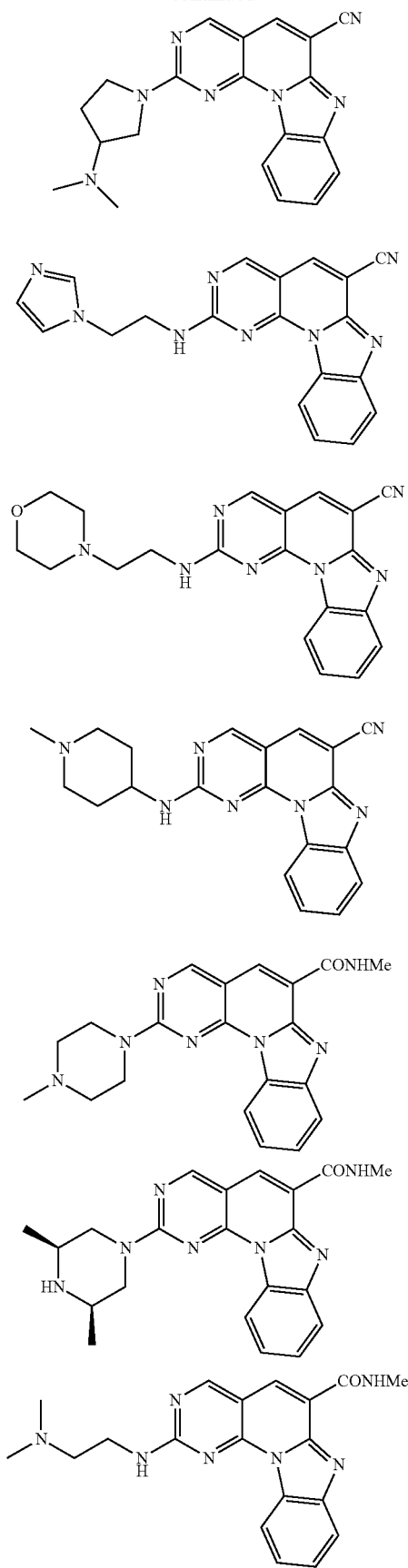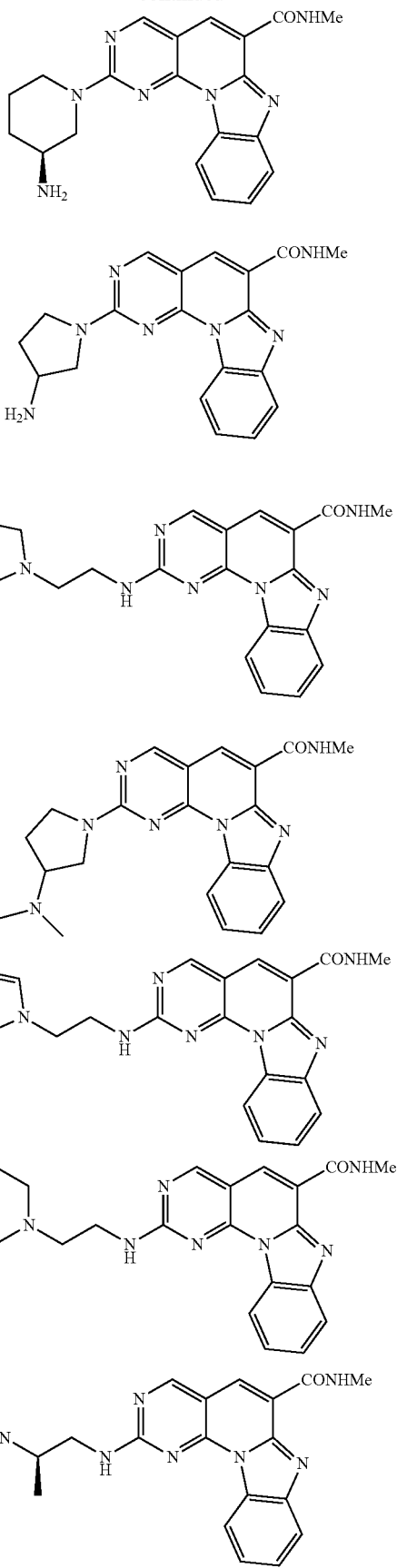

41
-continued
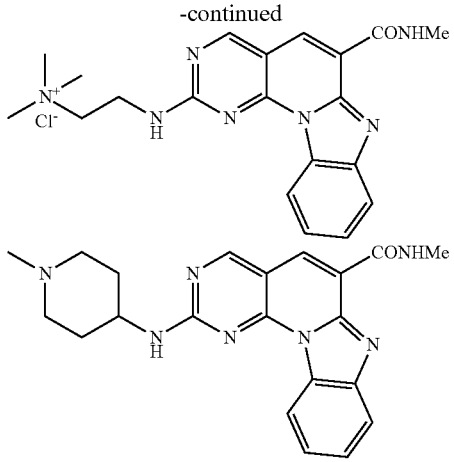
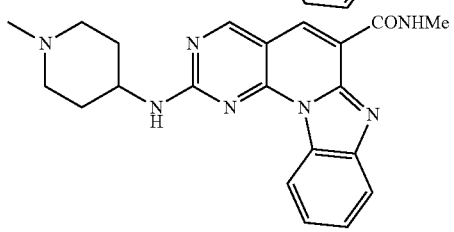
Non-limiting specific examples of compounds of Formula II(D) as described herein are illustrated in FIG. 4.
FIG. 4
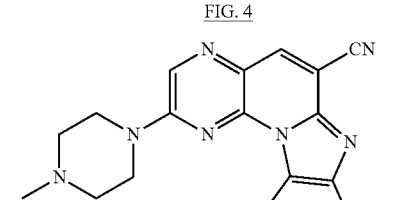
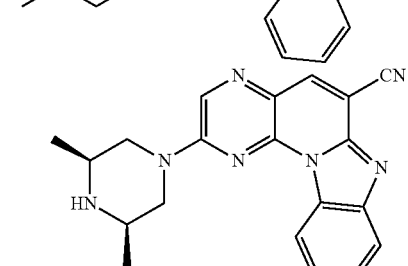
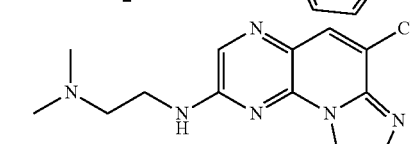
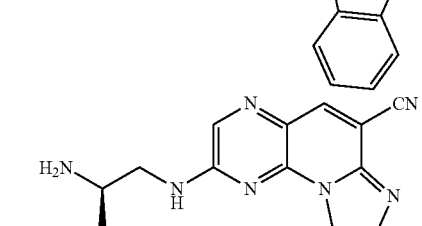
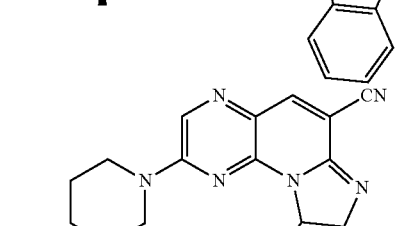
42
-continued
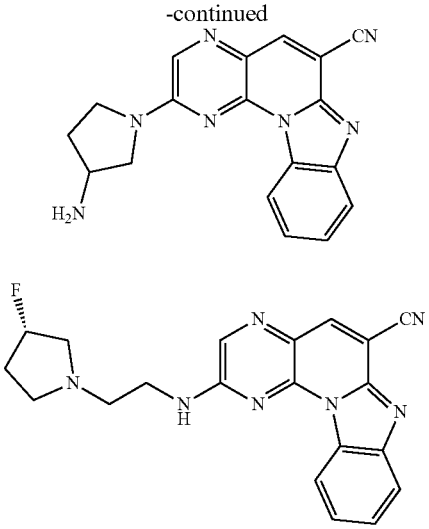
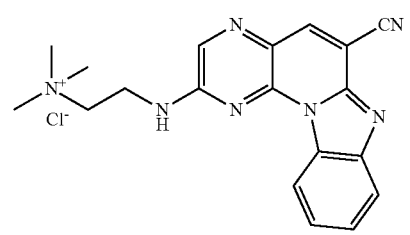
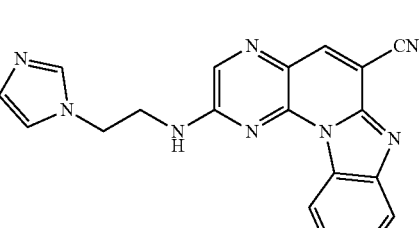
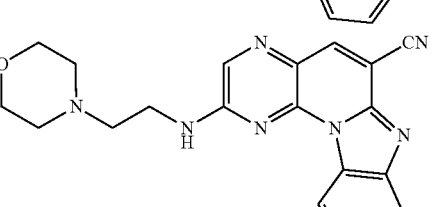
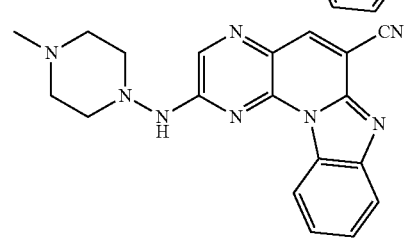

-continued
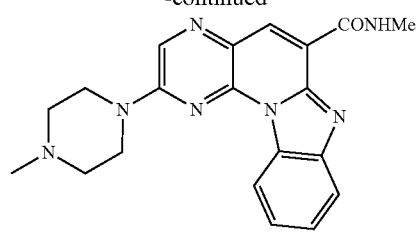
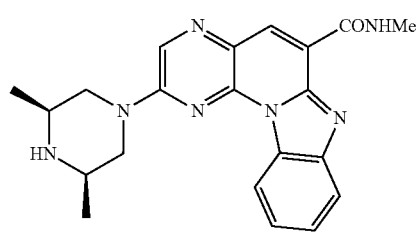
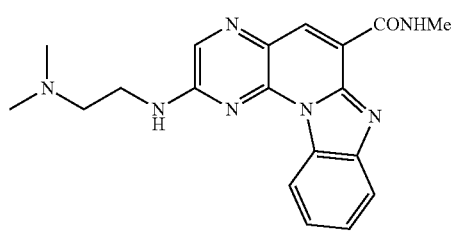
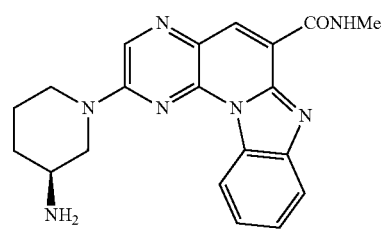
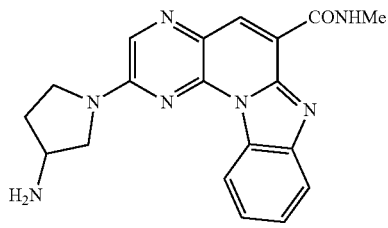
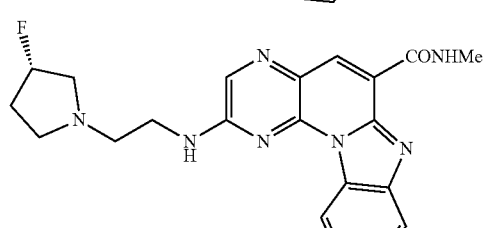
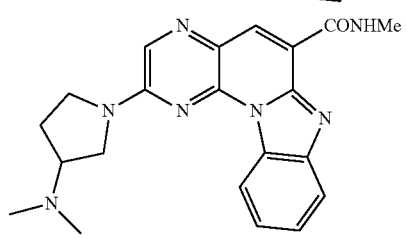
-continued
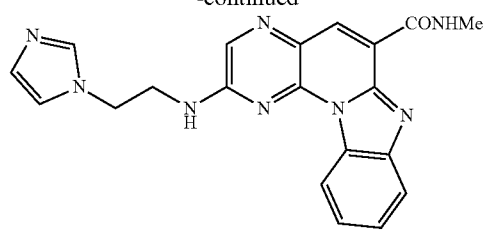
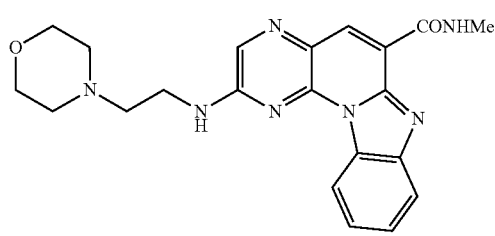
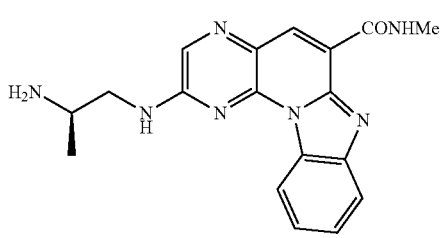
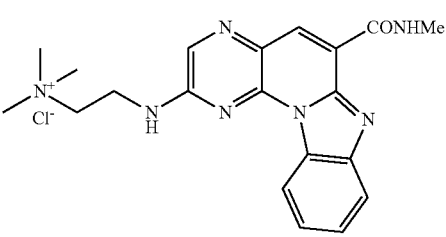
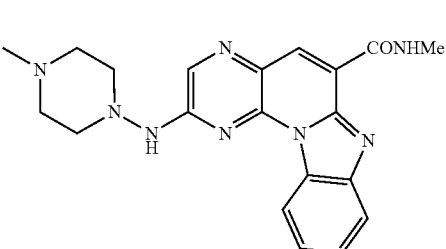
Non-limiting specific examples of compounds described herein are illustrated in FIG. 5.
FIG. 5
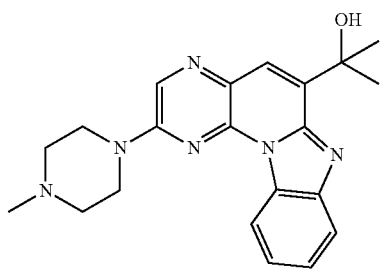

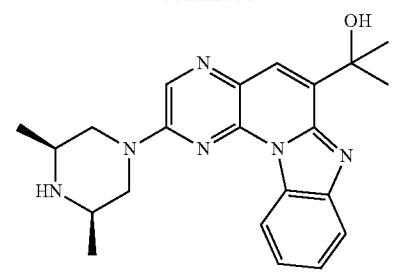
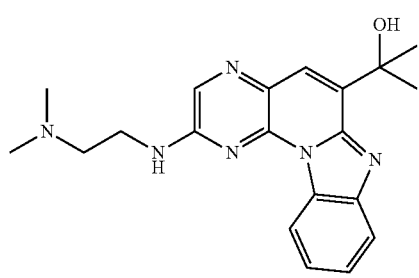
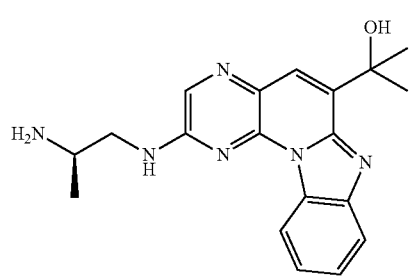
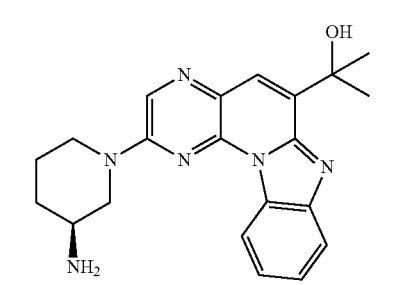
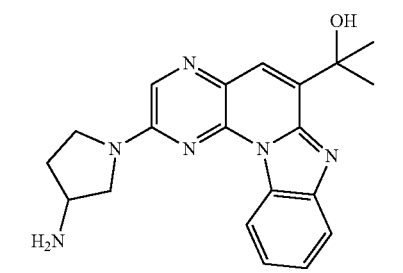
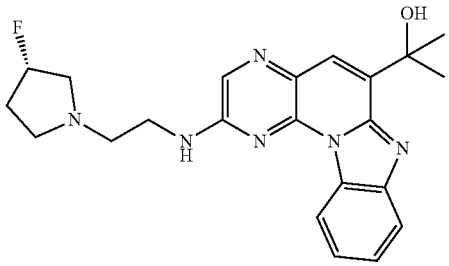
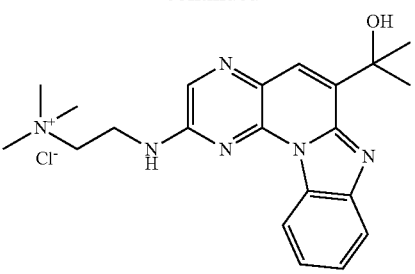
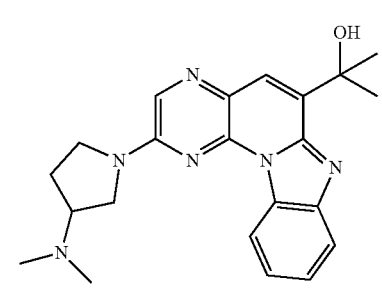
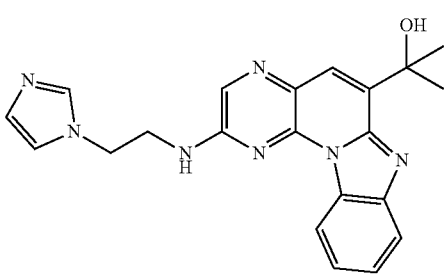
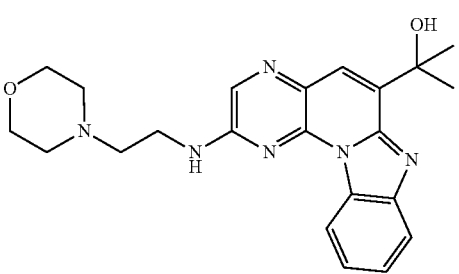
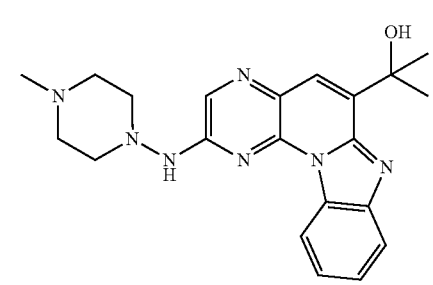

A method for preparing compounds of formula VI(B) are illustrated in Exemplary Scheme 11.
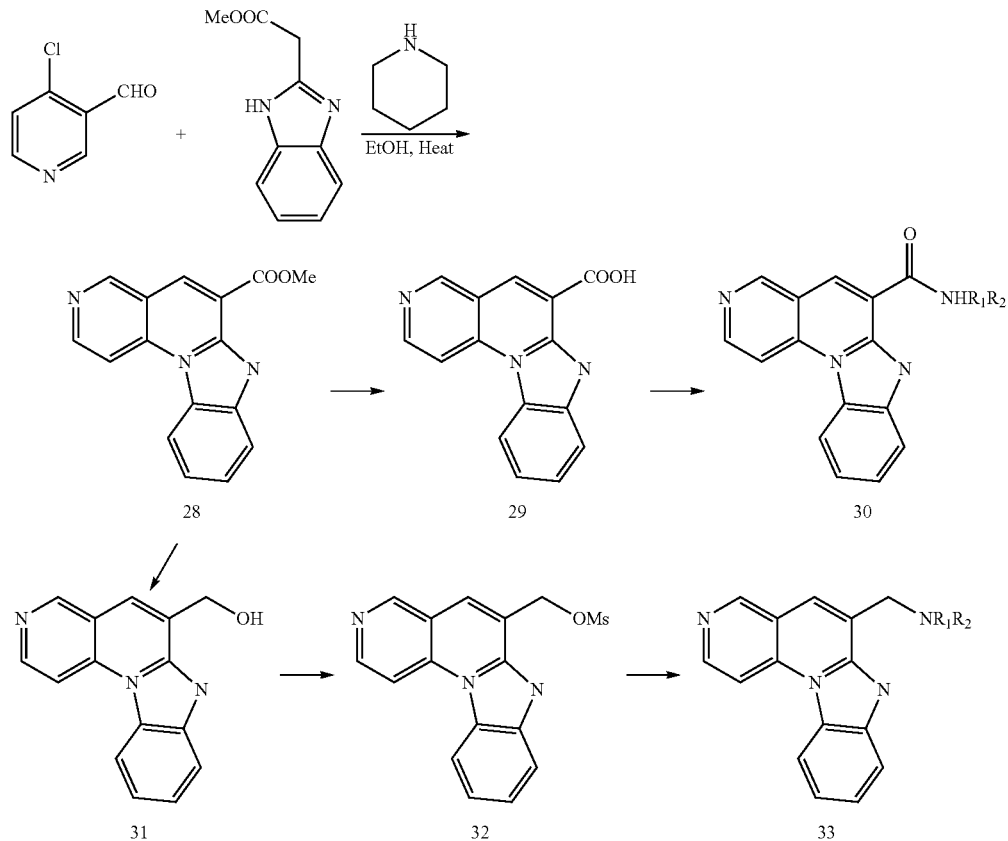
Method for preparing compounds of Formula VI(A) are illustrated in Exemplary Scheme 12.
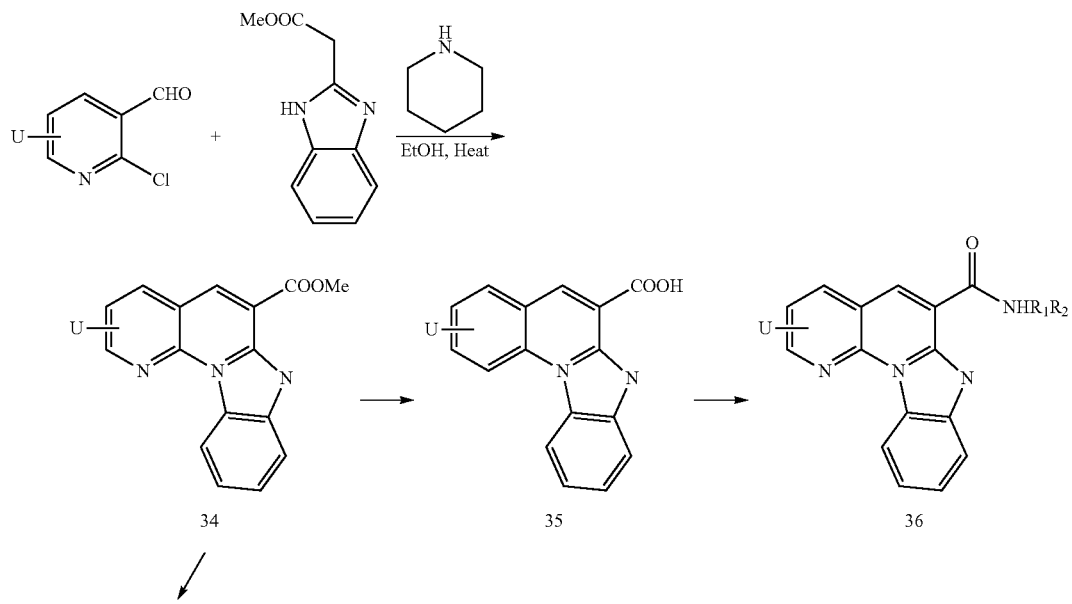

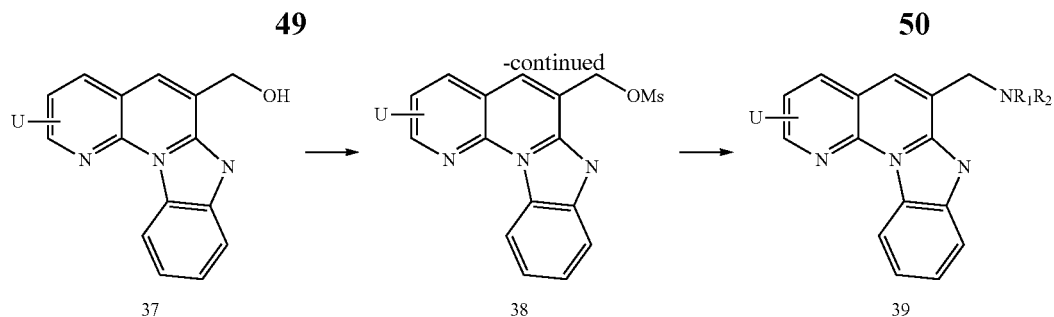

Compounds 30 and 34 can be prepared as described in exemplary scheme 8. The methyl ester group in compound 28 and 34 can be converted to a hydroxyl using a reducing agent such as LiBH₄ under appropriate conditions. The transformation of hydroxyl group in compounds 31 and 37 to a leaving group, followed by nucleophilic substitution leads to compounds 33 and 39 respectively.

FIG. 6 provides non-limiting representative examples of substituted chloropyridinecarboxaldehyde.

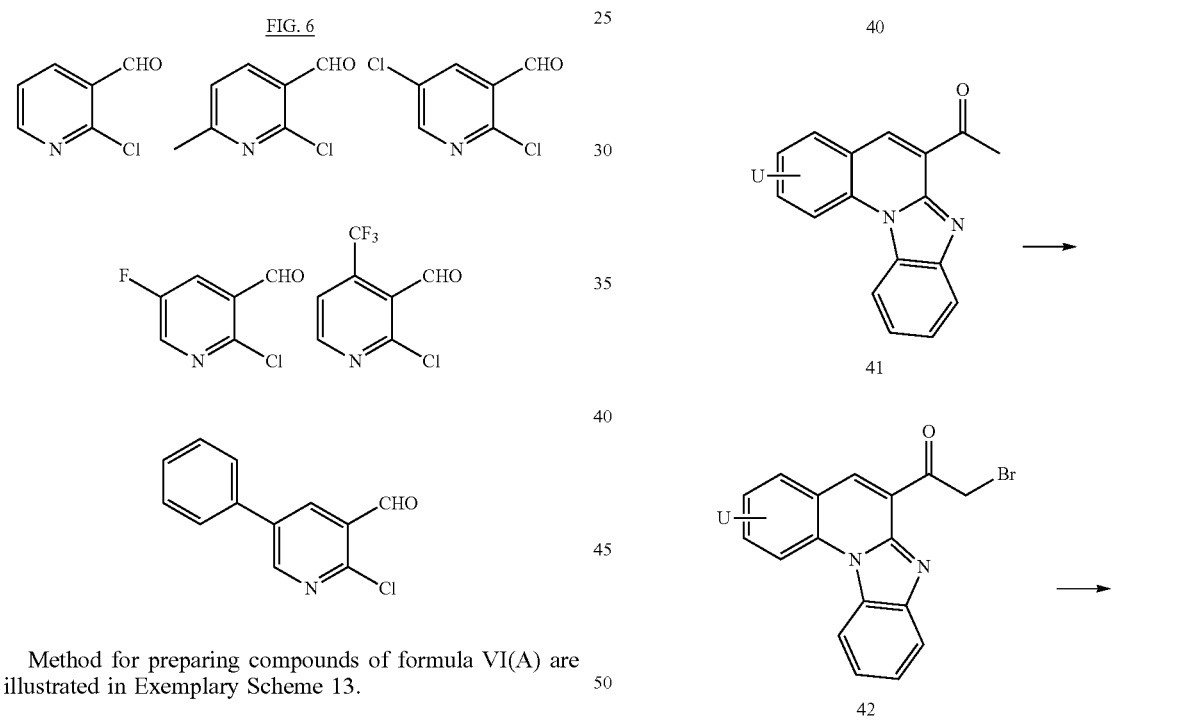

FIG. 6

Method for preparing compounds of formula VI(A) are illustrated in Exemplary Scheme 13.

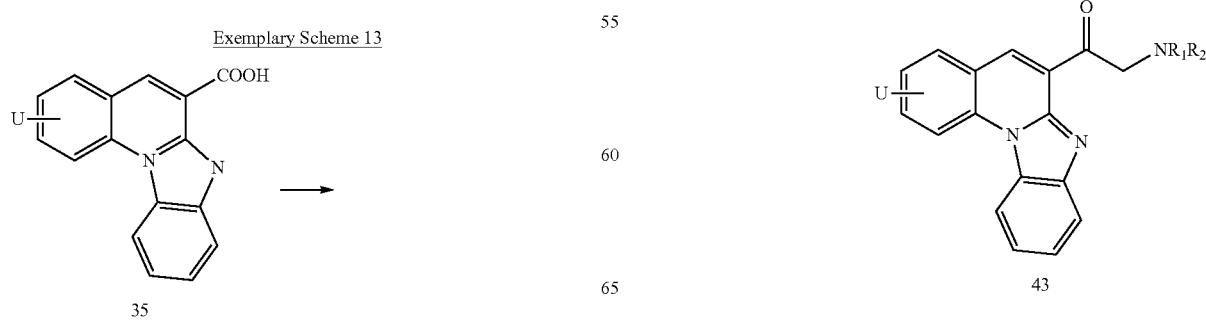

Exemplary Scheme 13

Compound 35 reacts with N,O-dimethylhydroxylamine hydrochloride under appropriate amide coupling conditions to give compound 40 and subsequent treatment of this compound with an organometallic reagent such as MeMgBr leads to compound 41. The treatement of compound 41 with brominating reagent such as N-Bromosuccinimide gives compound 42. The nucleophilic substitution with amines leads to compound 43.

A method for preparing compounds of formula V(A), V(B), V(C) and V(D) are illustrated in Exemplary Scheme 14.

Exemplary Scheme 14

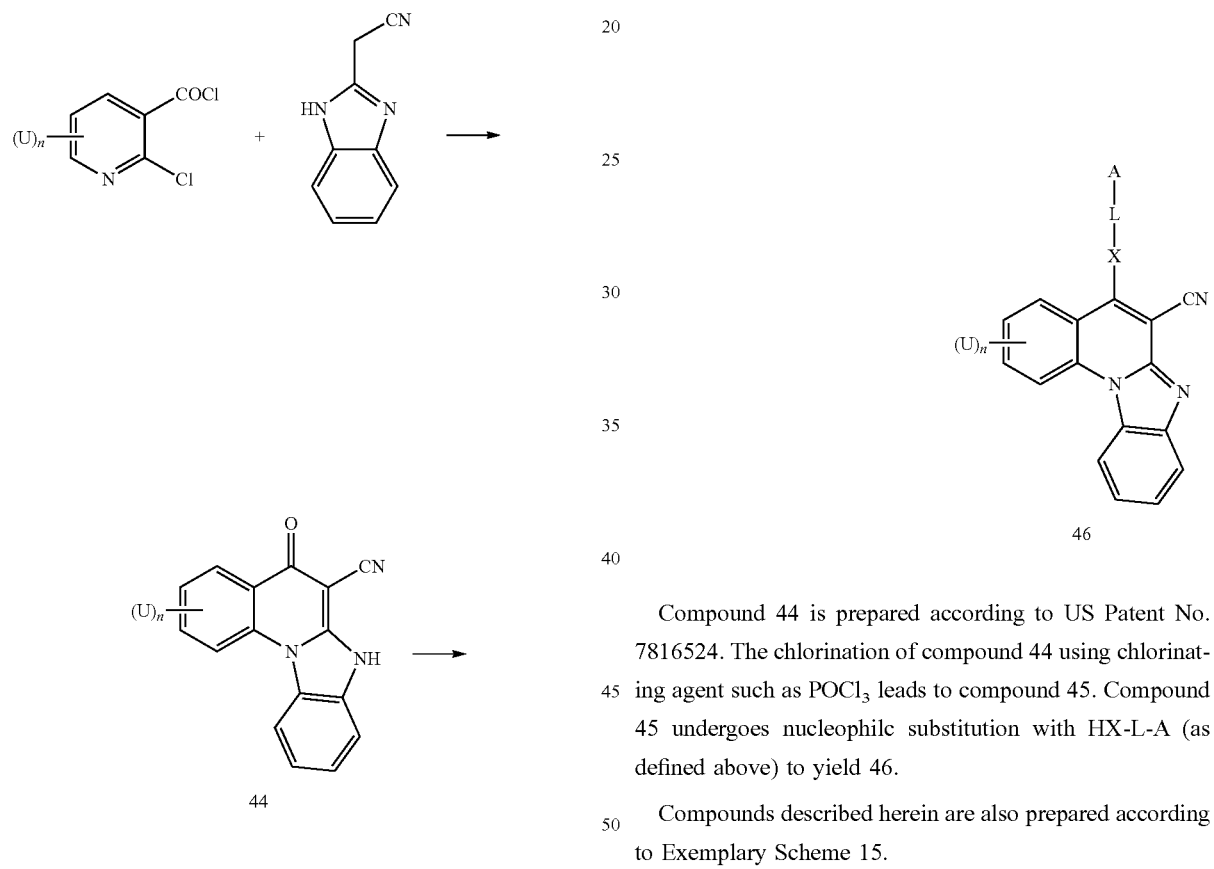

44

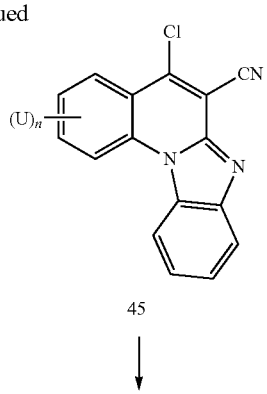

45

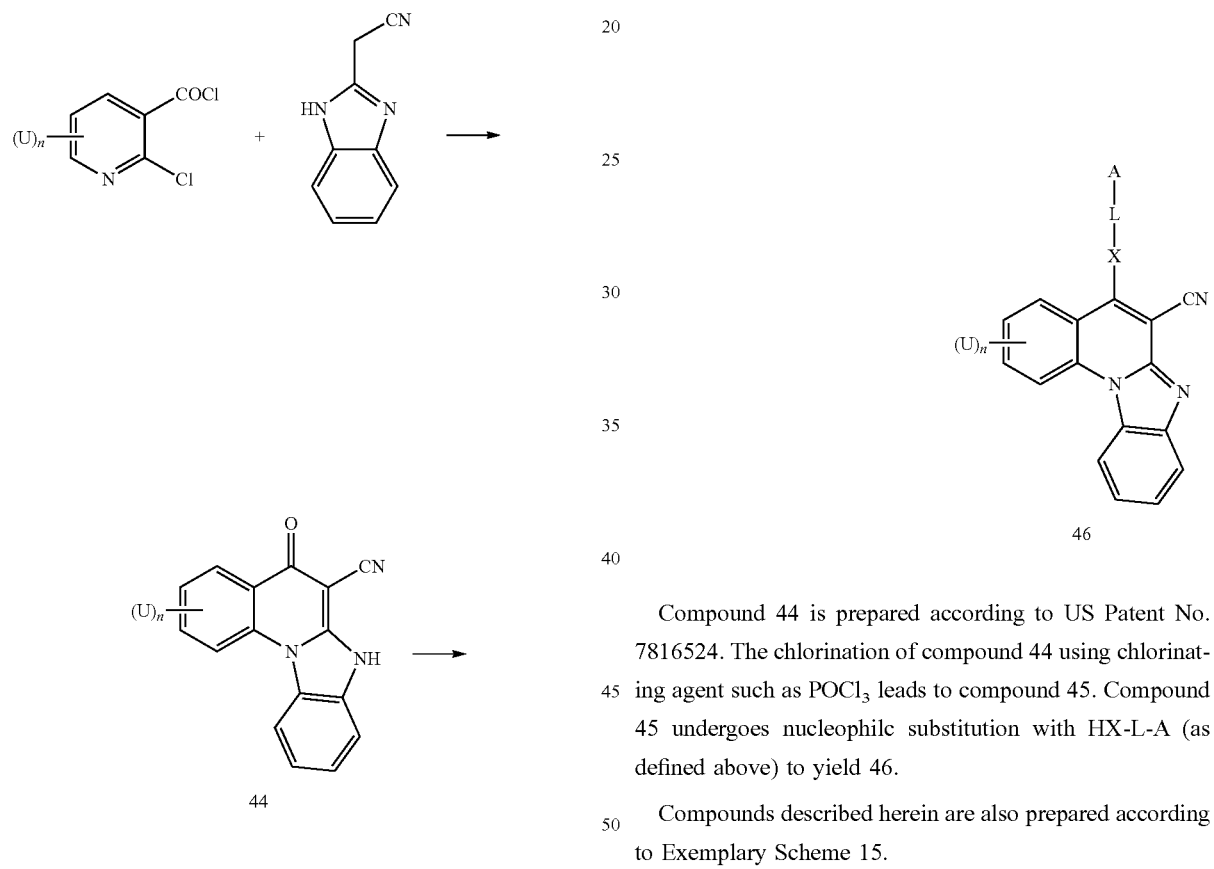

46

Compound 44 is prepared according to US Patent No. 7816524. The chlorination of compound 44 using chlorinating agent such as POCl₃ leads to compound 45. Compound 45 undergoes nucleophilc substitution with HX-L-A (as defined above) to yield 46.

Compounds described herein are also prepared according to Exemplary Scheme 15.

Exemplary Scheme 15

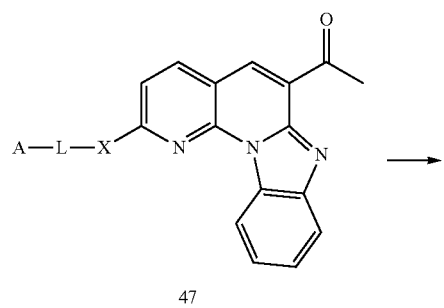

47

53 54
-continued
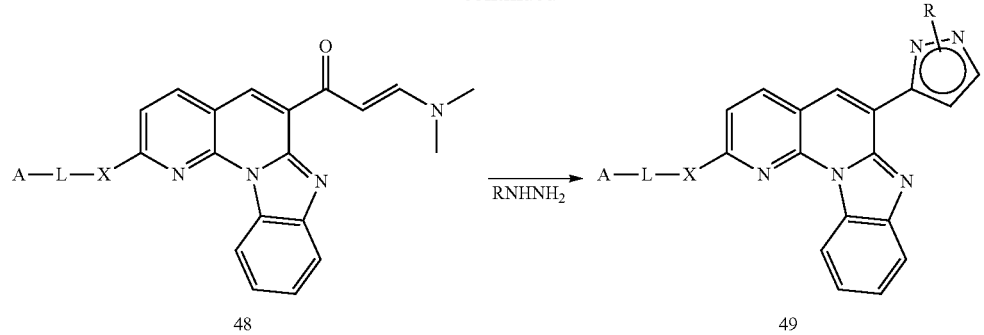
48
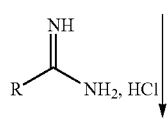
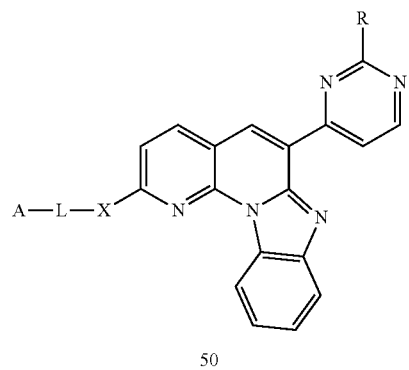
50
Compound 47 can be prepared as described in exemplary scheme 14. Compound 47 reacts with N,N-Dimethyformamide dimethy acetal to give compound 48. Compound 48 reacts with substituted hydrazine or substituted amidine to yield compound 49 and 50 respectively.
FIG. 7 provides non-limiting representative examples of $R_2R_1NH$ used in exemplary schemes 12, 13, 14, and 15.
FIG. 7
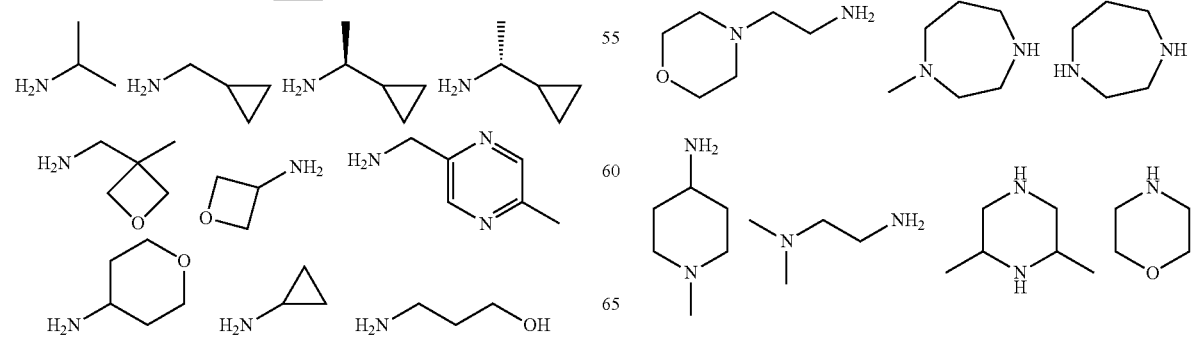
-continued
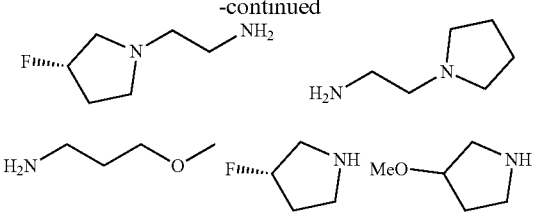

Compounds described herein are also prepared according to Exemplary Scheme 16.

Exemplary Scheme 16

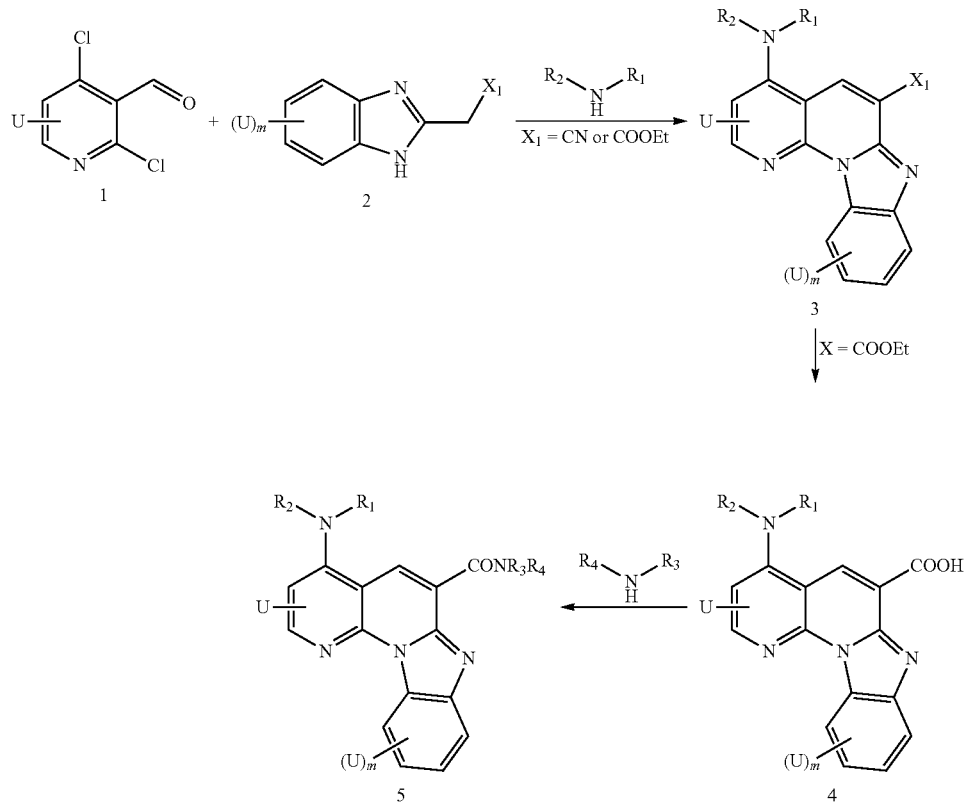

Compound 3 is prepared from the reaction of reagents 1 and 2 in appropriate solvent and appropriate temperature in the presence of an amine. The acid 4 can be prepared from hydrolysis of compound 3 (X=COOEt) and subsequent amide coupling leads to compound 5.

Non-limiting specific examples that can be preared by the method set forth in Exemplary Scheme 16 include:

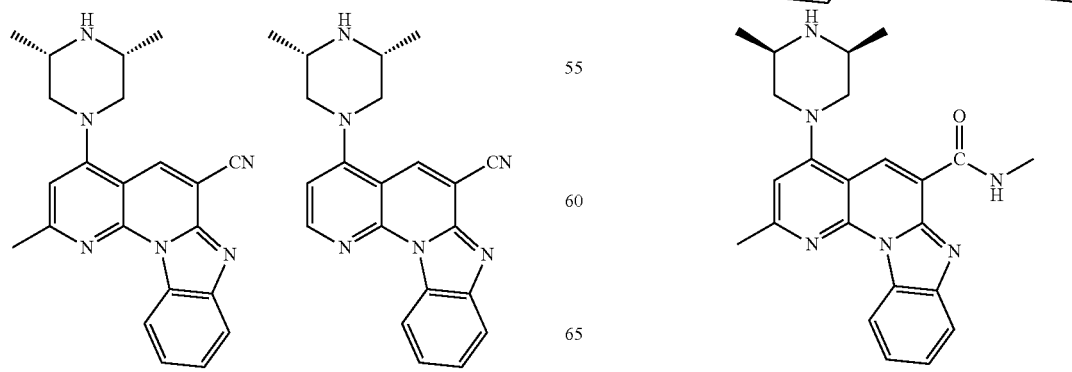

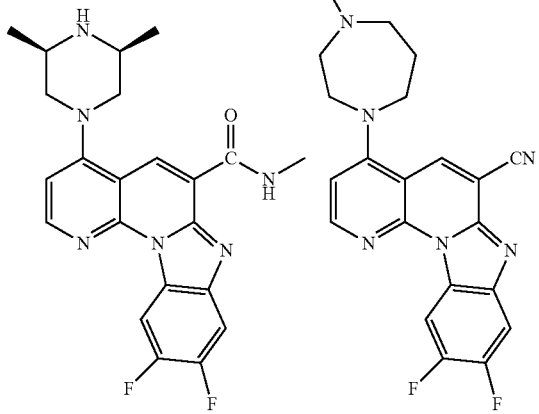
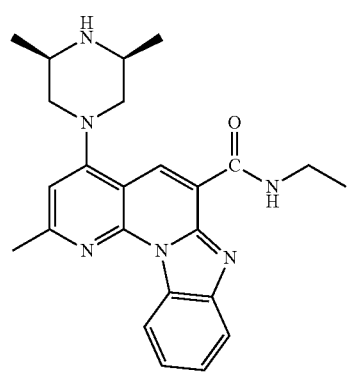
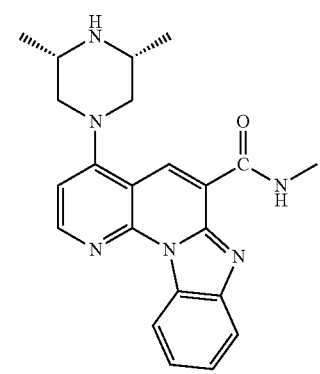
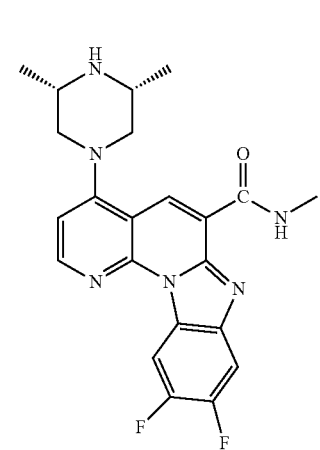
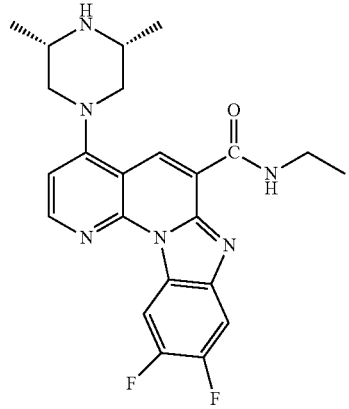
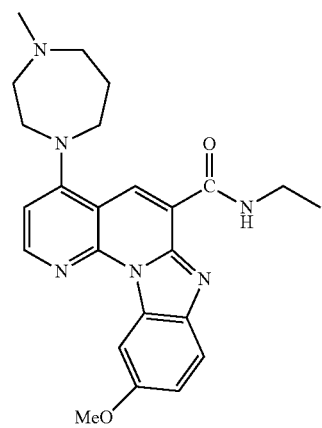
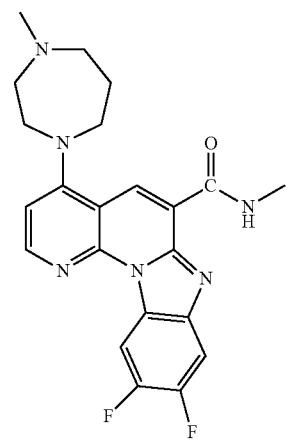
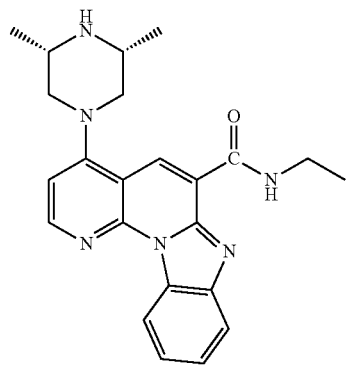

59
-continued
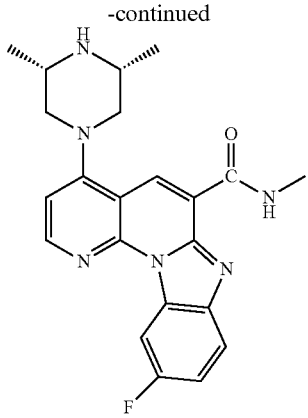
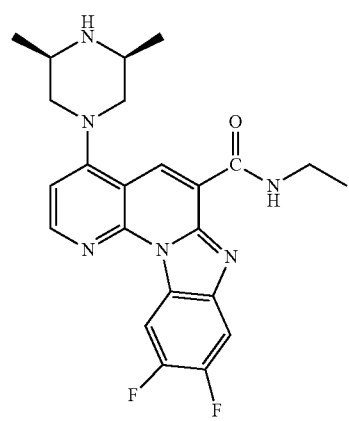
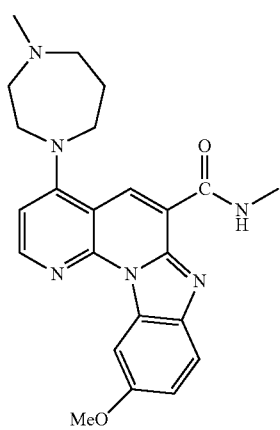
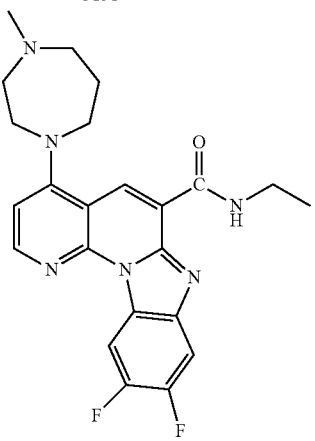
60
-continued
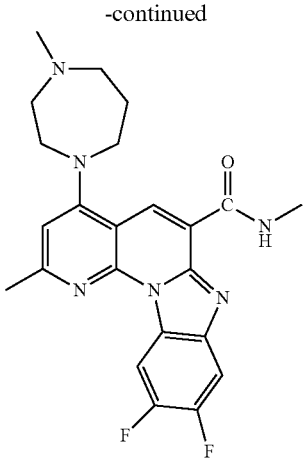
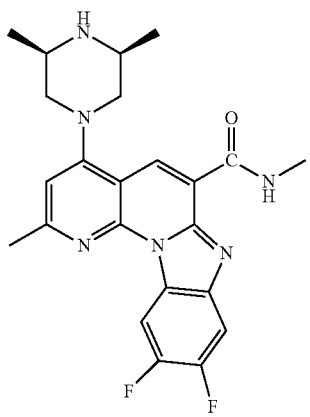
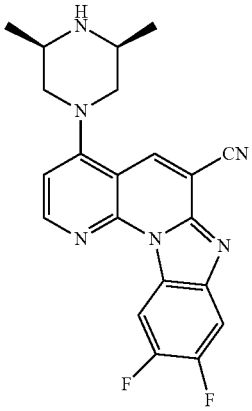
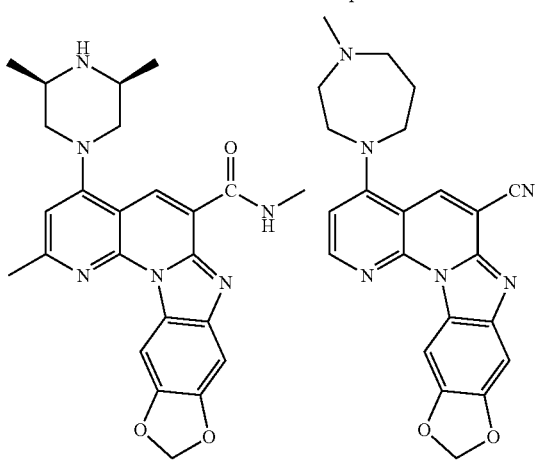

-continued
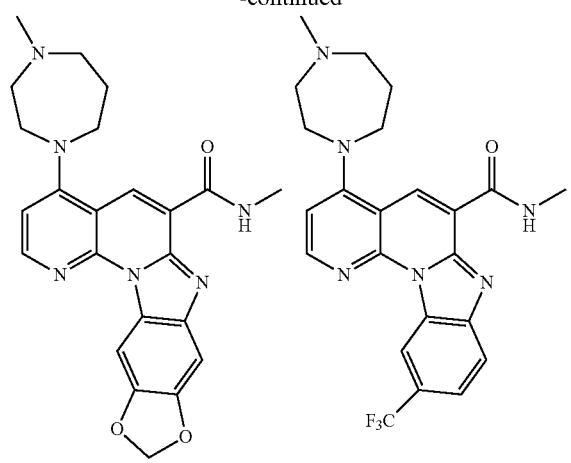
-continued
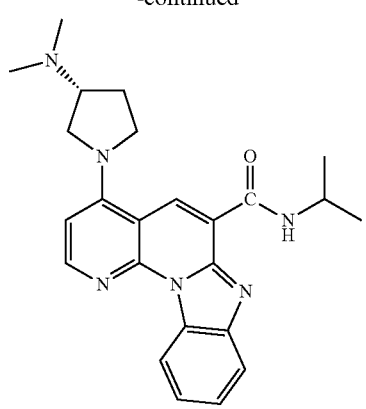
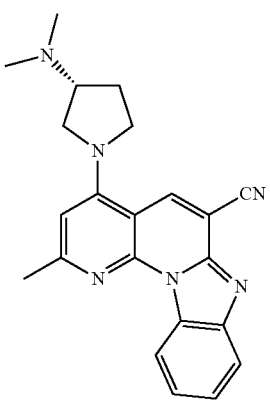 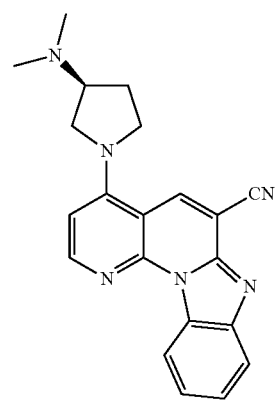
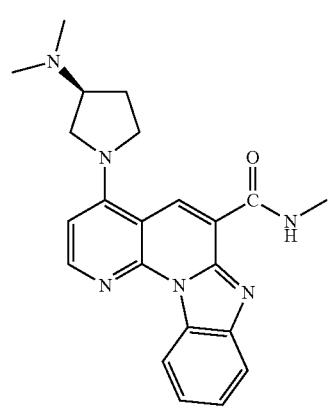
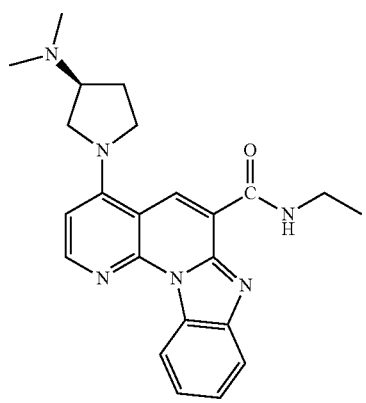

63
-continued
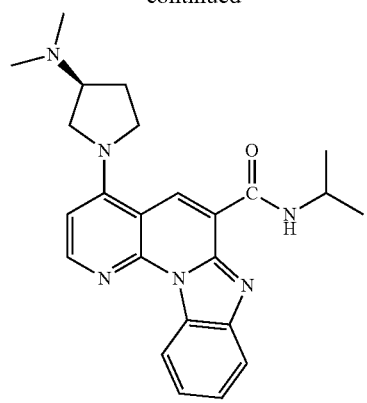
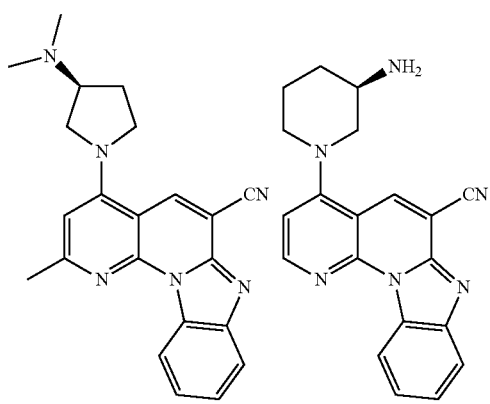
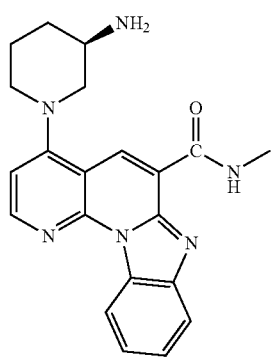
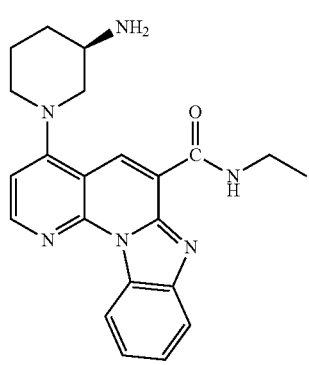
64
-continued
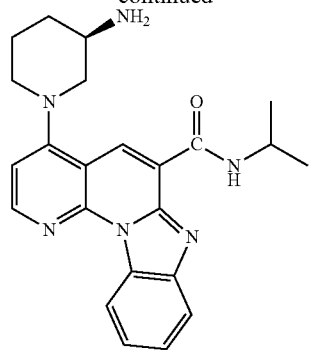
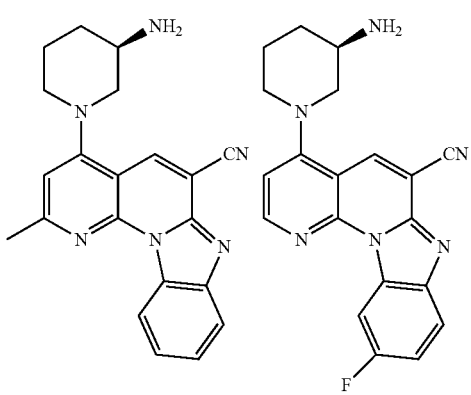
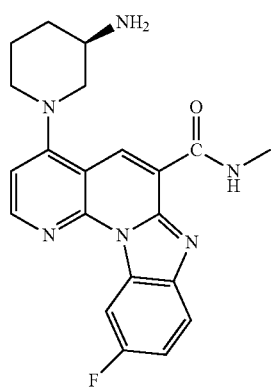
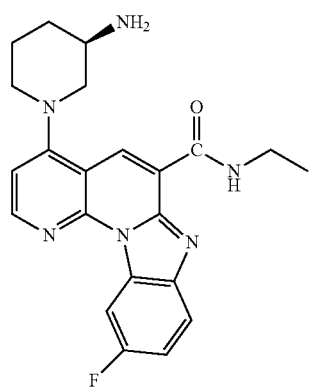

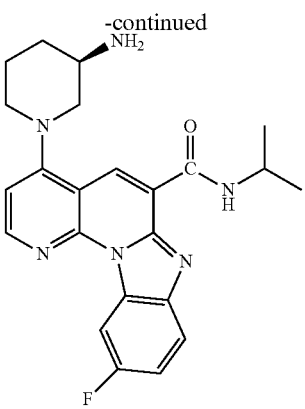
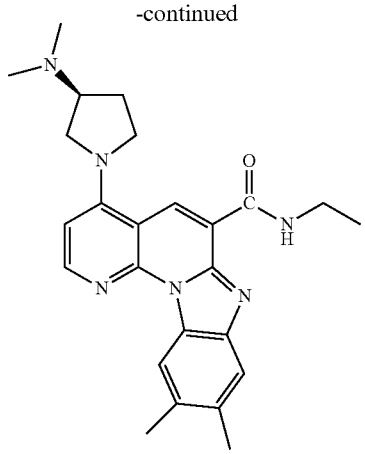
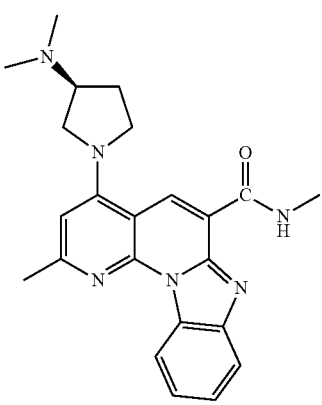
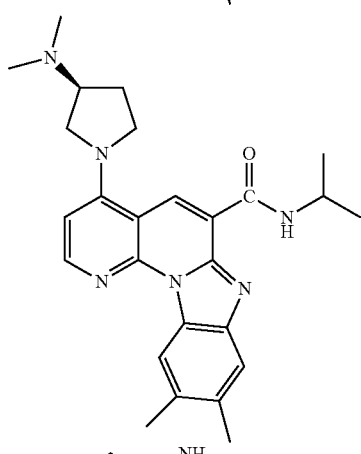
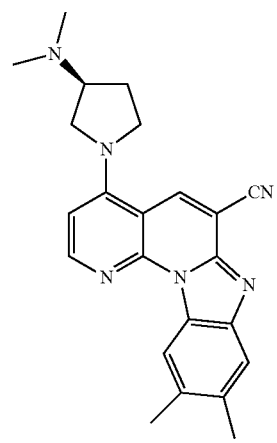
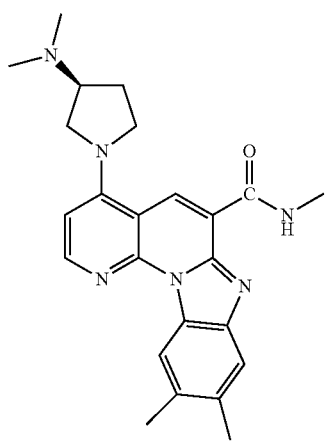

Other specific non-limiting examples prepared by the methods described herein include:

4-(4-Methyl-piperazin-1-yl)-1,7,11b-triaza-benzo[c]fluorene-6-carboxylic acid methylamide 2-Methyl-4-(4-methyl-piperazin-1-yl)-1,7,11b-triaza-benzo[c]fluorene-6-carboxylic acid methylamide 4-(4-Methyl-piperazin-1-yl)-2-trifluoromethyl-1,7,11b-triaza-benzo[c]fluorene-6-carboxylic acid hydroxyamide 2-Methyl-4-(4-methyl-piperazin-1-yl)-1,7,11b-triaza-benzo[c]fluorene-6-carboxylic acid hydroxyamide 4-(4-Methyl-piperazin-1-yl)-1,7,11b-triaza-benzo[c]fluorene-6-carboxylic acid hydroxyamide 4-(4-Methyl-piperazin-1-yl)-1,7,11b-triaza-benzo[c]fluorene-6-carboxylic acid methoxy-amide 2-Methyl-4-(4-methyl-piperazin-1-yl)-1,7,11b-triaza-benzo[c]fluorene-6-carboxylic acid methoxy-amide 4-(4-Methyl-piperazin-1-yl)-2-trifluoromethyl-1,7,11b-triaza-benzo[c]fluorene-6-carboxylic acid methoxy-amide 4-(3-Amino-piperidin-1-yl)-1,7,11b-triaza-benzo[c]fluorene-6-carboxylic acid methylamide
4-(3-Amino-piperidin-1-yl)-2-methyl-1,7,11b-triaza-benzo[c]fluorene-6-carboxylic acid methylamide
4-(3-Amino-piperidin-1-yl)-2-trifluoromethyl-1,7,11b-triaza-benzo[c]fluorene-6-carboxylic acid methylamide
4-[2-(3-Fluoro-pyrrolidin-1-yl)-ethylamino]-2-trifluoromethyl-1,7,11b-triaza-benzo[c]fluorene-6-carboxylic acid methylamide
4-[2-(3-Fluoro-pyrrolidin-1-yl)-ethylamino]-2-methyl-1,7,11b-triaza-benzo[c]fluorene-6-carboxylic acid methylamide
4-[2-(3-Fluoro-pyrrolidin-1-yl)-ethylamino]-2-methyl-1,7,11b-triaza-benzo[c]fluorene-6-carbonitrile
2-Methyl-4-(4-methyl-piperazin-1-yl)-1,7,11b-triaza-benzo[c]fluorene-6-carbonitrile
2-Methyl-4-(4-methyl-[1,4]diazepan-1-yl)-1,7,11b-triaza-benzo[c]fluorene-6-carbonitrile
4-(4-Ethyl-[1,4]diazepan-1-yl)-2-methyl-1,7,11b-triaza-benzo[c]fluorene-6-carbonitrile
4-(4-Isopropyl-[1,4]diazepan-1-yl)-2-methyl-1,7,11b-triaza-benzo[c]fluorene-6-carbonitrile
4-[1,4]Diazepan-1-yl-2-methyl-1,7,11b-triaza-benzo[c]fluorene-6-carbonitrile
4-[1,4]Diazepan-1-yl-2-methyl-1,7,11b-triaza-benzo[c]fluorene-6-carboxylic acid methylamide
4-[1,4]Diazepan-1-yl-1,7,11b-triaza-benzo[c]fluorene-6-carboxylic acid methylamide
[4-(4-Methyl-[1,4]diazepan-1-yl)-1,7,11b-triaza-benzo[c]fluoren-6-yl]-morpholin-4-yl-methanone
4-(4-Methyl-[1,4]diazepan-1-yl)-1,7,11b-triaza-benzo[c]fluorene-6-carboxylic acid (2-hydroxy-ethyl)-amide
4-(4-Methyl-[1,4]diazepan-1-yl)-1,7,11b-triaza-benzo[c]fluorene-6-carboxylic acid (2-methoxy-ethyl)-amide
4-(4-Methyl-[1,4]diazepan-1-yl)-1,7,11b-triaza-benzo[c]fluorene-6-carboxylic acid (2-methoxy-1-methyl-ethyl)-amide
2-Methyl-4-(4-methyl-[1,4]diazepan-1-yl)-1,7,11b-triaza-benzo[c]fluorene-6-carboxylic acid (2-methoxy-1-methyl-ethyl)-amide
2-Methyl-4-(4-methyl-[1,4]diazepan-1-yl)-1,7,11b-triaza-benzo[c]fluorene-6-carboxylic acid (2-methoxy-ethyl)-amide
4-(3,5-Dimethyl-piperazin-1-yl)-2-methyl-1,7,11b-triaza-benzo[c]fluorene-6-carboxylic acid (2-methoxy-ethyl)-amide
4-(3,5-Dimethyl-piperazin-1-yl)-2-methyl-1,7,11b-triaza-benzo[c]fluorene-6-carboxylic acid oxetan-3-ylamide
4-(3,5-Dimethyl-piperazin-1-yl)-2-methyl-1,7,11b-triaza-benzo[c]fluorene-6-carboxylic acid (pyridin-3-ylmethyl)-amide
10-Chloro-4-(3,5-dimethyl-piperazin-1-yl)-2-methyl-1,7,11b-triaza-benzo[c]fluorene-6-carboxylic acid methylamide
9-Chloro-4-(3,5-dimethyl-piperazin-1-yl)-1,7,11b-triaza-benzo[c]fluorene-6-carboxylic acid methylamide
4-(3,5-Dimethyl-piperazin-1-yl)-9,10-dimethyl-1,7,11b-triaza-benzo[c]fluorene-6-carboxylic acid methylamide
4-(2-Morpholin-4-yl-ethylamino)-1,7,11b-triaza-benzo[c]fluorene-6-carboxylic acid methylamide
4-(2-Diethyl amino-ethylamino)-1,7,11b-triaza-benzo[c]fluorene-6-carboxylic acid methylamide
4-[(1-Methyl-1H-imidazol-4-ylmethyl)-amino]-1,7,11b-triaza-benzo[c]fluorene-6-carboxylic acid methylamide
4-(2-Imidazol-1-yl-ethylamino)-1,7,11b-triaza-benzo[c]fluorene-6-carboxylic acid methylamide
4-[4-(2-Methoxy-ethyl)-piperazin-1-yl]-1,7,11b-triaza-benzo[c]fluorene-6-carboxylic acid methylamide
4-[4-(2-Methoxy-ethyl)-piperazin-1-yl]-1,7,11b-triaza-benzo[c]fluorene-6-carboxylic acid isopropylamide
4-(4-Methyl-[1,4]diazepan-1-yl)-6-[1,3,4]oxadiazol-2-yl-1,7,11b-triaza-benzo[c]fluorene
4-(4-Methyl-[1,4]diazepan-1-yl)-6-(5-methyl-[1,3,4]oxadiazol-2-yl)-1,7,11b-triaza-benzo[c]fluorene
4-(4-Methyl-[1,4]diazepan-1-yl)-6-(4H-[1,2,4]triazol-3-yl)-1,7,11b-triaza-benzo[c]fluorine
4-(4-Methyl-[1,4]di azepan-1-yl)-6-(1H-tetrazol-5-yl)-1,7,11b-triaza-benzo[c]fluorine
4-(4-Methyl-[1,4]di azepan-1-yl)-6-oxazol-2-yl-1,7,11b-triaza-benzo[c]fluorine
4-(3,5-Dimethyl-piperazin-1-yl)-6-oxazol-2-yl-1,7,11b-triaza-benzo[c]fluorine
4-(3,5-Dimethyl-piperazin-1-yl)-6-[1,3,4]oxadiazol-2-yl-1,7,11b-triaza-benzo[c]fluorine
4-(3,5-Dimethyl-piperazin-1-yl)-6-(4H-[1,2,4]triazol-3-yl)-1,7,11b-triaza-benzo[c]fluorine
4-(3,5-Dimethyl-piperazin-1-yl)-6-(5-methyl-4H-[1,2,4]triazol-3-yl)-1,7,11b-triaza-benzo[c]fluorene
3-Fluoro-2-(4-methyl-[1,4]diazepan-1-yl)-1,7,11b-triaza-benzo[c]fluorene-6-carboxylic acid methylamide
3-Fluoro-2-(4-methyl-[1,4]diazepan-1-yl)-1,7,11b-triaza-benzo[c]fluorene-6-carboxylic acid isopropylamide
2-(3,5-Dimethyl-piperazin-1-yl)-3-fluoro-1,7,11b-triaza-benzo[c]fluorene-6-carboxylic acid methylamide
3-Fluoro-2-(4-methyl-piperazin-1-yl)-1,7,11b-triaza-benzo[c]fluorene-6-carboxylic acid methylamide
3-Fluoro-2-[4-(2-methoxy-ethyl)-piperazin-1-yl]-1,7,11b-triaza-benzo[c]fluorene-6-carboxylic acid methylamide
3-Fluoro-2-(2-pyrrolidin-1-yl-ethylamino)-1,7,11b-triaza-benzo[c]fluorene-6-carboxylic acid methylamide
2-(3,5-Dimethyl-piperazin-1-yl)-3-fluoro-1,7,11b-triaza-benzo[c]fluorene-6-carboxylic acid methylamide
2-(3,5-Dimethyl-piperazin-1-yl)-3-fluoro-1,7,11b-triaza-benzo[c]fluorene-6-carboxylic acid isopropylamide
2-(3,5-Dimethyl-piperazin-1-yl)-3-fluoro-1,7,11b-triaza-benzo[c]fluorene-6-carboxylic acid cyclopropylamide
2-(3,5-Dimethyl-piperazin-1-yl)-3-fluoro-1,7,11b-triaza-benzo[c]fluorene-6-carboxylic acid (2-methoxy-ethyl)-amide
2-(3,5-Dimethyl-piperazin-1-yl)-3-fluoro-1,7,11b-triaza-benzo[c]fluorene-6-carboxylic acid ethylamide
2-(3,5-Dimethyl-piperazin-1-yl)-4-methyl-1,7,11b-triaza-benzo[c]fluorene-6-carboxylic acid ethylamide
2-(3,5-Dimethyl-piperazin-1-yl)-4-methyl-1,7,11b-triaza-benzo[c]fluorene-6-carboxylic acid methylamide
2-(3,5-Dimethyl-piperazin-1-yl)-4-methyl-1,7,11b-triaza-benzo[c]fluorene-6-carboxylic acid cyclopropylamide
2-(3,5-Dimethyl-piperazin-1-yl)-4-methyl-1,7,11b-triaza-benzo[c]fluorene-6-carboxylic acid (2-methoxy-ethyl)-amide
2-(3,5-Dimethyl-piperazin-1-yl)-4-trifluoromethyl-1,7,11b-triaza-benzo[c]fluorene-6-carboxylic acid (2-methoxy-ethyl)-amide
2-(3,5-Dimethyl-piperazin-1-yl)-4-trifluoromethyl-1,7,11b-triaza-benzo[c]fluorene-6-carboxylic acid methylamide
2-[1,4]Diazepan-1-yl-4-trifluoromethyl-1,7,11b-triaza-benzo[c]fluorene-6-carboxylic acid methylamide
2-[1,4]Diazepan-1-yl-4-methyl-1,7,11b-triaza-benzo[c]fluorene-6-carboxylic acid methylamide
2-[1,4]Diazepan-1-yl-3-fluoro-1,7,11b-triaza-benzo[c]fluorene-6-carboxylic acid methylamide
2-[1,4]Diazepan-1-yl-1,7,11b-triaza-benzo[c]fluorene-6-carboxylic acid methylamide
2-(4-Ethyl-[1,4]diazepan-1-yl)-1,7,11b-triaza-benzo[c]fluorene-6-carboxylic acid methylamide 2-(4-Isopropyl-[1,4]diazepan-1-yl)-1,7,11b-triaza-benzo[c]fluorene-6-carboxylic acid methylamide
2-(4-Methyl-[1,4]diazepan-1-yl)-1,7,11b-triaza-benzo[c]fluorene-6-carboxylic acid ethylamide
2-(4-Methyl-[1,4]di azepan-1-yl)-1,7,11b-triaza-benzo[c]fluorene-6-carboxylic acid (pyridin-3-ylmethyl)-amide
2-(4-Methyl-[1,4]diazepan-1-yl)-1,7,11b-triaza-benzo[c]fluorene-6-carboxylic acid (2-imidazol-1-yl-ethyl)-amide
10-Chloro-2-(4-methyl-[1,4]diazepan-1-yl)-1,7,11b-triaza-benzo[c]fluorene-6-carboxylic acid methylamide
10-Cyano-2-(4-methyl-[1,4]diazepan-1-yl)-1,7,11b-triaza-benzo[c]fluorene-6-carboxylic acid methylamide
9,10-Dimethyl-2-(4-methyl-[1,4]diazepan-1-yl)-1,7,11b-triaza-benzo[c]fluorene-6-carboxylic acid methylamide
4-Methyl-2-(4-methyl-[1,4]diazepan-1-yl)-1,7,11b-triaza-benzo[c]fluorene-6-carboxylic acid methylamide
2-(4-Methyl-[1,4]di azepan-1-yl)-4-trifluoromethyl-1,7,11b-triaza-benzo[c]fluorene-6-carboxylic acid methylamide
3-Fluoro-2-(4-methyl-[1,4]diazepan-1-yl)-1,7,11b-triaza-benzo[c]fluorene-6-carboxylic acid hydroxyamide
3-Fluoro-2-(4-methyl-[1,4]diazepan-1-yl)-1,7,11b-triaza-benzo[c]fluorene-6-carboxylic acid methoxy-amide
3-Fluoro-2-(4-methyl-[1,4]diazepan-1-yl)-1,7,11b-triaza-benzo[c]fluorene-6-carboxylic acid N'-methyl-hydrazide
3-Fluoro-2-(4-methyl-[1,4]diazepan-1-yl)-1,7,11b-triaza-benzo[c]fluorene-6-carboxylic acid amide
2-(4-Methyl-[1,4]di azepan-1-yl)-1,7,11b-triaza-benzo[c]fluorene-6-carboxylic acid amide
2-[1,4]Diazepan-1-yl-1,7,11b-triaza-benzo[c]fluorene-6-carboxylic acid amide
2-[1,4]Diazepan-1-yl-1,7,11b-triaza-benzo[c]fluorene-6-carboxylic acid
2-(4-Methyl-[1,4]diazepan-1-yl)-1,7,11b-triaza-benzo[c]fluorene-6-carboxylic acid (2-hydroxy-1-methyl-ethyl)-amide
2-(4-Methyl-[1,4]diazepan-1-yl)-1,7,11b-triaza-benzo[c]fluorene-6-carboxylic acid (2-methoxy-1-methyl-ethyl)-amide
[2-(4-Methyl-[1,4]diazepan-1-yl)-1,7,11b-triaza-benzo[c]fluoren-6-yl]-pyrrolidin-1-yl-methanone
[2-(4-Methyl-[1,4]diazepan-1-yl)-1,7,11b-triaza-benzo[c]fluoren-6-yl]-(2-methyl-pyrrolidin-1-yl)-methanone
(3-Hydroxymethyl-pyrrolidin-1-yl)-[2-(4-methyl-[1,4]diazepan-1-yl)-1,7,11b-triaza-benzo[c]fluoren-6-yl]-methanone
(3,3-Difluoro-pyrrolidin-1-yl)-[2-(4-methyl-[1,4]diazepan-1-yl)-1,7,11b-tri aza-benzo[c]fluoren-6-yl]-methanone
(3-Dimethylamino-pyrrolidin-1-yl)-[2-(4-methyl-[1,4]diazepan-1-yl)-1,7,11b-triaza-benzo[c]fluoren-6-yl]-methanone
2-(3-Dimethylamino-pyrrolidin-1-yl)-1,7,11b-triaza-benzo[c]fluorene-6-carboxylic acid methylamide
2-(4-Methyl-[1,4]di azepan-1-yl)-1,7,11b-triaza-benzo[c]fluoren-6-yl)-(4-methyl-piperazin-1-yl)-methanone
2-(4-Methyl-[1,4]di azepan-1-yl)-1,7,11b-triaza-benzo[c]fluorene-6-carboxylic acid (1-methyl-azetidin-3-yl)-amide
2-(4-Methyl-[1,4]di azepan-1-yl)-1,7,11b-triaza-benzo[c]fluorene-6-carboxylic acid (2-pyrrolidin-1-yl-ethyl)-amid
2-(4-Methyl-[1,4]diazepan-1-yl)-1,7,11b-triaza-benzo[c]fluorene-6-carboxylic acid (2,2-difluoro-ethyl)-amide
[1,4]Diazepan-1-yl-(3,7,11b-triaza-benzo[c]fluoren-6-yl)-methanone
(4-Methyl-[1,4]diazepan-1-yl)-(3,7,11b-triaza-benzo[c]fluoren-6-yl)-methanone
(4-Methyl-piperazin-1-yl)-(3,7,11b-triaza-benzo[c]fluoren-6-yl)-methanone
(3,5-Dimethyl-piperazin-1-yl)-(3,7,11b-triaza-benzo[c]fluoren-6-yl)-methanone
6-(5-Methyl-[1,3,4]oxadi azol-2-yl)-3,7,11b-triaza-benzo[c]fluorine
6-(4H-[1,2,4]Triazol-3-yl)-3,7,11b-triaza-benzo[c]fluorine
2-Methyl-3,7,11b-triaza-benzo[c]fluorene-6-carboxylic acid (2-pyrrolidin-1-yl-ethyl)-amide
2,4-Dimethyl-3,7,11b-triaza-benzo[c]fluorene-6-carboxylic acid (2-pyrrolidin-1-yl-ethyl)-amide
2-Methyl-3,7,11b-triaza-benzo[c]fluorene-6-carboxylic acid (2-morpholin-4-yl-ethyl)-amide
(4-Methyl-[1,4]diazepan-1-yl)-(2-methyl-3,7,11b-triaza-benzo[c]fluoren-6-yl)-methanone Certain Terminology Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$ alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$ alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers refers to a divalent alkyl radical. Any of the above mentioned monovalent alkyl groups may be an alkylene by abstraction of a second hydrogen atom from the alkyl. In some embodiments, an alkelene is a $C_1$-$C_6$alkylene. In other embodiments, an alkylene is a $C_1$-$C_4$alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

"Azacyclic" or "azacyclic ring" refers to a saturated, partially unsaturated, or aromatic 3-7 membered monocyclic ring or an 8-12 membered fused bicyclic ring system containing at least one nitrogen atom. Such azacyclic rings may optionally contain from 1-2 additional heteroatoms selected from N, O, and S as ring members, and may optionally be substituted to the extent such substitutions make chemical sense.

"Deuteroalkyl" refers to an alkyl group where 1 or more hydrogen atoms of an alkyl are replaced with deuterium.

The term "alkenyl" refers to a type of alkyl group in which at least one carbon-carbon double bond is present. In one embodiment, an alkenyl group has the formula —C(R)

=CR₂, wherein R refers to the remaining portions of the alkenyl group, which may be the same or different. In some embodiments, R is H or an alkyl. Non-limiting examples of an alkenyl group include —CH═CH₂, —C(CH₃)═CH₂—CH═CHCH₃, —C(CH₃)═CHCH₃, and —CH₂CH═CH₂.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. Non-limiting examples of an alkynyl group include —C≡CH, —C≡CCH₃—C≡CCH₂CH₃, —CH₂CCH.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

The term "aromatic" refers to a planar ring having a delocalized π-electron system containing 4n+2 π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a $C_6$-$C_{10}$ aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1] pentyl. In some embodiments, a cycloalkyl is a $C_3$-$C_6$ cycloalkyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoralkyl is a $C_1$-$C_6$ fluoroalkyl.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$ heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (═O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$ heteroaryl. In some embodiments, monocyclic heteroaryl is a $C_1$-$C_5$ heteroaryl. In some embodiments, monocyclic heteroaryl is a 5-membered or 6-membered heteroaryl. In some embodiments, bicyclic heteroaryl is a $C_6$-$C_9$ heteroaryl.

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$ heterocycloalkyl. In another aspect, a heterocycloalkyl is a $C_4$-$C_{10}$ heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, —NH$_2$, —NH(alkyl), —N(alkyl)$_2$, —OH, —CO$_2$H, —CO$_2$ alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —NH$_2$, —NH (CH$_3$), —N(CH$_3$)$_2$, —OH, —CO$_2$H, —CO$_2$(C$_1$-C$_4$ alkyl), —C(=O)NH$_2$, —C(=O)NH(C$_1$-C$_4$ alkyl), —C(=O)N (C$_1$-C$_4$ alkyl)$_2$, —S(=O)$_2$NH$_2$, —S(=O)$_2$NH(C$_1$-C$_4$ alkyl), —S(=O)$_2$N(C$_1$-C$_4$ alkyl)$_2$, C$_1$-C$_4$ alkyl, C$_3$-C$_6$cycloalkyl, C$_1$-C$_4$fluoroalkyl, C$_1$-C$_4$ heteroalkyl, C$_1$-C$_4$alkoxy, C$_1$-C$_4$ fluoroalkoxy, —SC$_1$-C$_4$ alkyl, —S(=O)C$_1$-C$_4$ alkyl, and —S(=O)$_2$C$_1$-C$_4$ alkyl. In some embodiments, optional substituents are independently selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

"Carboxylate bioisostere" or "carboxy bioisostere" as used herein refers to a moiety that is expected to be negatively charged to a substantial degree at physiological pH. In certain embodiments, the carboxylate bioisostere is a moiety selected from the group consisting of:

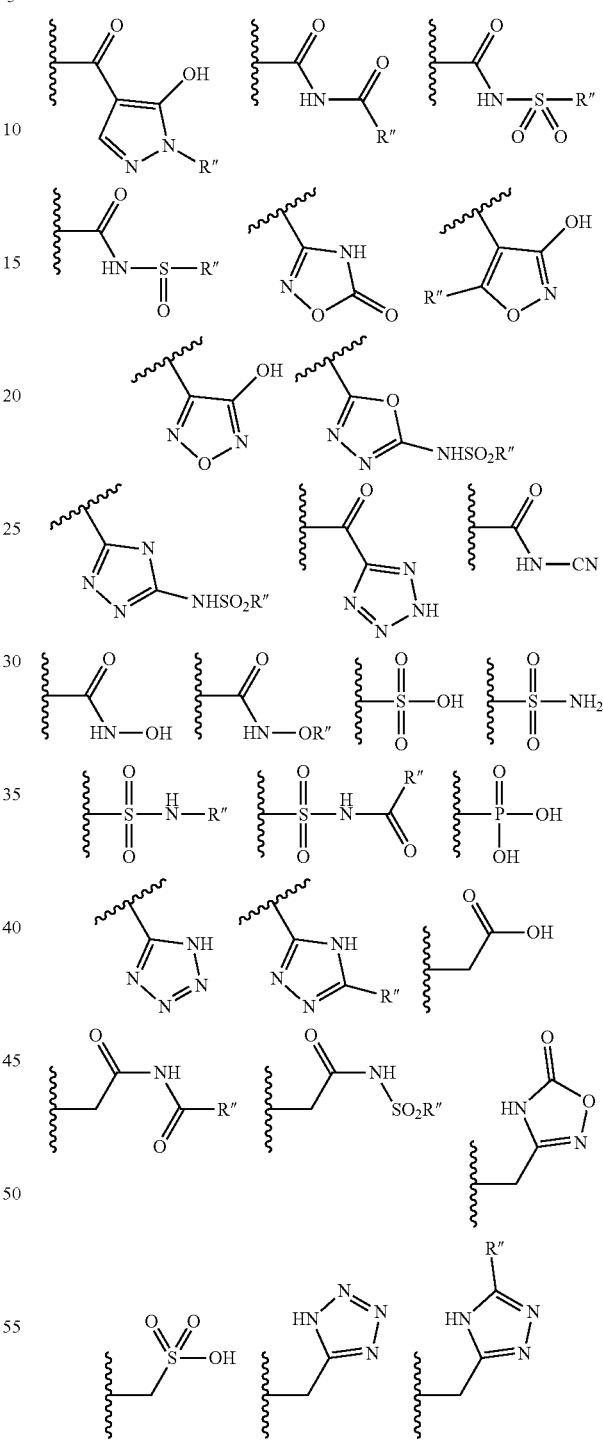

and salts of the forgoing, wherein each R" is independently H or an optionally substituted member selected from the group consisting of C$_{1-10}$ alkyl, C$_{2-10}$ alkenyl, C$_{2-10}$ heteroalkyl, C$_{3-8}$ carbocyclic ring; or R" is a C$_{1-10}$ alkyl, C$_{2-10}$ alkenyl, or C$_{2-10}$ heteroalkyl substituted with an optionally substituted C$_{3-8}$ carbocyclic ring or C$_{3-8}$ heterocyclic ring.

Amide bioisostere and ester bioisostere as used herein refer to a moieties represented by the following examples:

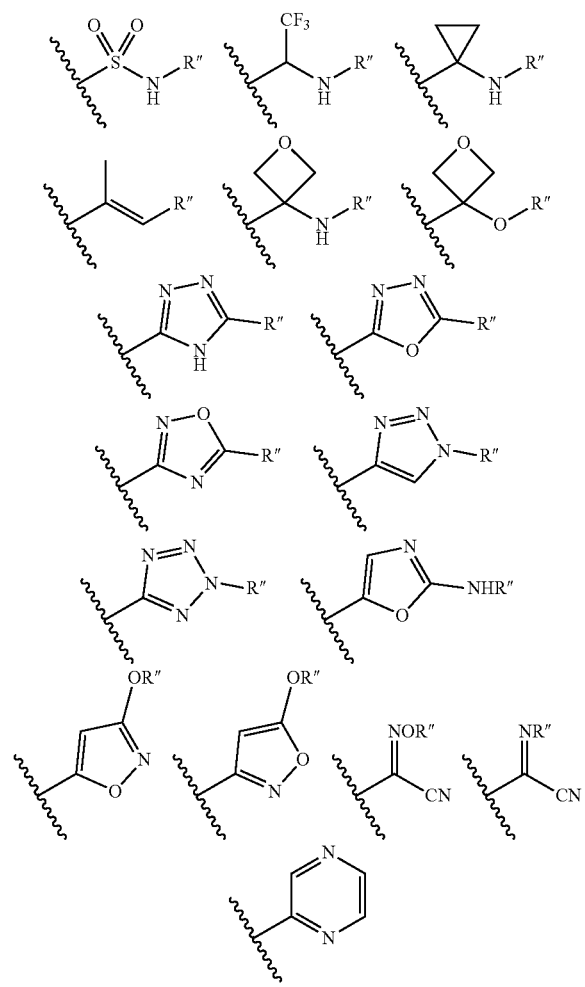

wherein each R" is independently H or an optionally substituted member selected from the group consisting of $C_{1-10}$ alkyl, $C_{2-10}$ alkenyl, $C_{2-10}$ heteroalkyl, $C_{3-8}$ carbocyclic ring; or R" is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring.

The compounds presented herein may possess one or more stereocenters and each center may exist in the R or S configuration. The compounds presented herein include all diastereomeric, enantiomeric, and epimeric forms as well as the appropriate mixtures thereof. Stereoisomers may be obtained, if desired, by methods known in the art such as, for example, the separation of individual stereoisomers by chiral chromatographic columns or by stereoselective synthesis.

A "quaternary amine" is a positively charged polyatomic ion of the structure $NR_4^+$, where R is an alkyl or aryl group. The four (4) R groups that make up the quaternary amine may be the same or different and may be connected to one another. Quaternary amines can be prepared by the alkylation of tertiary amines, in a process called quaternization, as well as by other methods known in the art.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein, or a pharmaceutically acceptable salt thereof, and a co-agent, are both administered to a patient simultaneously in the form of a single entity or dosage. The term "non-fixed combination" means that the active ingredients, e.g. a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. It is understood in the art that proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal compositions such as suppositories or retention enemas, e.g., containing conventional suppository bases such as cocoa butter, polyethylene glycol, or other glycerides.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds described herein, or a pharmaceutically acceptable salt thereof, are used in the preparation of medicaments for the treatment of diseases or conditions in a mammal that would benefit from inhibiting POL1 transcription. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In some embodiments, the invention provides methods of treating conditions associated with polymerase I transcription, comprising: administering to a patient in need thereof an effective amount of a compound of the invention. In another embodiment, the invention provides a method of inhibiting polymerase I transcription: comprising, contacting the enzyme with a compound of the invention. In a further embodiment, the invention provides a method of inhibiting polymerase I transcription: comprising, administering a first compound to a subject that is converted in vivo to a compound of the invention.

"Conditions associated with polymerase I transcription" include disorders and diseases in which the inhibition of polymerase I transcription provides a therapeutic benefit, such as cancer, allergy/asthma, diseases and conditions of the immune system, inflammation, disease and conditions of the central nervous system (CNS), cardiovascular disease, viral infections, dermatological disease, and diseases and conditions related to uncontrolled angiogenesis, and the like. Where general terms are used herein to describe conditions associated with polymerase I transcription it is understood that the more specifically described conditions mentioned in the various diagnostic manuals and other materials are included within the scope of this invention.

The term "cancer," as used herein refers to an abnormal growth of cells, which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias). See, Ding X Z et al., Anticancer Drugs. 2005 June; 16(5):467-73. Review; Chen X 52814-701.305 et al., Clin Cancer Res. 2004 Oct. 1; 10(19):6703-9, each of which are incorporated by reference herein in their entirety.

For example, it is understood that the treatment of cancer includes treatment of all neoplasia, regardless of their histopathological appearance. Particularly, the cancers that can be treated include, but are not limited to, cancer of blood, including myelofibrosis, leukemia (including acute myelogenous leukemia, chronic myelogenous leukemia, acute lymphocytic leukemia, chronic lymphocytic leukemia), cancer of the skin, including melanoma, basal cell carcinoma, and squamous cell carcinoma, bone, liver, lung (including small-cell lung tumor, non small-cell lung cancer and bronchioalveolar cancer), brain, breast, prostate, larynx, gall bladder, pancreas, rectum, bile duct, parathyroid, thyroid, adrenal, neural tissue, bladder, spleen, head and neck, included the jaw, mouth, and nose, colon, stomach, testes, esophagus, uterus, cervix and vulva, colorectal, bronchi, bile duct, bladder, kidney, ovary, pancreas, multiple myeloma, lymphomas, basal cell carcinoma, squamous cell carcinoma of both ulcerating and papillary type, osteo sarcoma, Ewing's sarcoma, veticulum cell sarcoma, myeloma, giant cell tumor, islet cell tumor, acute and chronic lymphocytic and granulocytic tumors, hairy-cell tumor, adenoma, hyperplasia, medullary carcinoma, pheochromocytoma, mucosal neuronms, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, myelodysplastic syndrome, mycosis fungicide, rhabdomyosarcoma, astrocytoma, non-Hodgkin's lymphoma, Kaposi's sarcoma, osteogenic and other sarcoma, malignant hypercalcemia, polycythermia vera, adenocarcinoma, glioblastoma multiforma, glioma, lymphomas, epidermoid carcinomas, and other carcinomas and sarcomas.

Benign tumors may also be treated by the compounds of the present invention and include, but are not limited to, hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas, pyogenic granulomas, and the like, and hamartoma conditions such as Peutz-Jeghers Syndrome (PJS), Cowden disease, Bannayan-Riley-Ruvalcaba Syndrome (BRRS), Proteus syndrome, Lhermitte-Duclos disease and Tuberous Sclerosis (TSC).

The compounds of the present invention may also be used to treat abnormal cell proliferation due to insults to body tissue during surgery. These insults may arise as a result of a 52814-701.305 variety of surgical procedures such as joint surgery, bowel surgery, and cheloid scarring. Diseases that produce fibrotic tissue include emphysema. Repetitive motion disorders that may be treated using the present invention include carpal tunnel syndrome.

The compounds of the invention may also be useful in the prevention of restenosis that is the control of undesired proliferation of normal cells in the vasculature in response to the introduction of stents in the treatment of vasculature disease.

Proliferative responses associated with organ transplantation that may be treated using Pol I transcription inhibitors of the invention include proliferative responses contributing to potential organ rejections or associated complications. Specifically, these proliferative responses may occur during transplantation of the heart, lung, liver, kidney, and other body organs or organ systems.

The compounds of the invention may also be useful the treatment of abnormal angiogenesis including the abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopaphy, and other ocular angiogenic diseases such as retinopathy of prematurity (retrolental fibroplastic), macular degeneration, corneal graft rejection, neuroscular glaucoma, Oster Webber syndrome, retinal/choroidal neuvascularization and corneal neovascularization, Best's disease, myopia, optic pits, Stargart's diseases, Pagets disease, vein occlusion, artery occlusion, sickle cell anemia, sarcoid, syphilis, pseudoxanthoma elasticum carotid abstructive diseases, chronic uveitis/vitritis, mycobacterial infections, Lyme's disease, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle), diseases caused by the abnormal proliferation of fibrovascular or fibrous tissue including all forms of proliferative vitreoretinopathy, atopic keratitis, superior limbic keratitis, pterygium keratitis sicca, sjogrens, acne rosacea, phylectenulosis, diabetic retinopathy, retinopathy of prematurity, corneal graft rejection, Mooren's ulcer, Terrien's marginal degeneration, marginal keratolysis, polyarteritis, Wegener sarcoidosis, scleritis, periphigoid radial keratotomy, neovascular glaucoma and retrolental fibroplasia, syphilis, Mycobacteria infections, lipid degeneration, 52814-701.305 chemical burns, bacterial ulcers, fungal ulcers, Herpes simplex infections, Herpes zoster infections, protozoan infections, and Kaposi sarcoma, Alzheimer's disease, Parkinson's disease amyotrophic lateral sclerosis (ALS), epilepsy, seizures, Huntington's disease, polyglutamine diseases, traumatic brain injury, ischemic and hemorrhaging stroke, cerebral ischemias or neurodegenerative disease, including apoptosis-driven neurodegenerative disease, caused by traumatic injury, acute hypoxia, ischemia or glutamate neurotoxicity.

For example, it is understood that treatments of inflammation include, but are not limited to, acute pancreatitis, chronic pancreatitis, asthma, allergies, chronic obstructive pulmonary disease, adult respiratory distress syndrome and chronic inflammatory diseases associated with uncontrolled angiogenesis, inflammatory bowel diseases such as Crohn's disease and ulcerative colitis, psoriasis, sarcoidois, and rheumatoid arthritis, sarcoidosis, and multisystem granulomatous disorder.

For example, it is understood that treatment of autoimmune includes, but is not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, multiple sclerosis, or Sjoegren's syndrome.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the LD50 and the $ED_{50}$. The dose ratio between the toxic and therapeutic effects is the therapeutic index and it is expressed as the ratio between LD50 and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain instances, it is appropriate to administer at least one compound described herein, or a pharmaceutically acceptable salt thereof, in combination with one or more other therapeutic agents. In certain embodiments, the pharmaceutical composition further comprises one or more anti-cancer agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

A wide variety of therapeutic agents may have a therapeutic additive or synergistic effect with the compounds according to the present invention. Combination therapies that comprise one or more compounds of the present invention with one or more other therapeutic agents can be used, for example, to: (1) enhance the therapeutic effect(s) of the one or more compounds of the present invention and/or the one or more other therapeutic agents; (2) reduce the side effects exhibited by the one or more compounds of the present invention and/or the one or more other therapeutic agents; and/or (3) reduce the effective dose of the one or more compounds of the present invention and/or the one or more other therapeutic agents. It is noted that combination therapy is intended to cover when agents are administered before or after each other (sequential therapy) as well as when the agents are administered at the same time.

Examples of such therapeutic agents that may be used in combination with the present compounds include, but are not limited to, anti-cell proliferation agents, anticancer agents, alkylating agents, antibiotic agents, antimetabolic agents, hormonal agents, plant-derived agents, and biologic agents.

Anti-cell proliferation agents useful in combination with the compounds of the present invention include, but are not limited to, retinoid acid and derivatives thereof, 2-methoxyestradiol, ANGIOSTATIN™ protein, ENDOSTATIN™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((l-azetidine-2-carboxylic acid (LACA), cishydroxyproline, d,1-3,4-dehydroproline, thiaproline, beta-aminopropionitrile fumarate, 4-propyl-5-(4-pyridinyl)-2(3H)-oxazolone, methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpha-2-antiplasmin, bisantrene, lobenzarit di sodium, n-(2-carboxyphenyl-4-chloroanthronilic acid disodium or "CCA", thalidomide, angostatic steroid, cargboxynaminolmidazole, metalloproteinase inhibitors such as BB94. Other anti-angiogenesis agents that may be used include antibodies, preferably monoclonal antibodies against these angiogenic growth factors: bFGF, aFGF, FGF-5, VEGF isoforms, VEGF-C, HGF/SF and Ang-1/Ang-2.

Inhibitors of mTOR, PI3K, MEK, MAPK, PIM or ERK kinases are useful in combination with the compounds of the present invention. Specifically, (R)-3-(2,3-Dihydroxypropyl)-6-fluoro-5-(2-fluoro-4-iodophenylamino)-8-methylpyrido[2,3-d]pyrimidine-4,7(3H,8H)-dione useful in combination with the compounds of the present invention. Inhibitors of Hedgehog kinase are useful in combination with the compounds of the present invention. Proteasome inhibitors, in particular bortezomib is useful in combination with the compounds of the present invention.

NAE inhibitors, VPS34 inhibitors, Aurora kinase, including Aurora A inhibitors, and EGFR inhibitors (both antibodies and kinase inhibitors) are useful in combination with the compounds of the present invention.

Alkylating agents useful in combination with the compunds disclosed herein include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin). Combination therapy including a polymerase I inhibitor and an alkylating agent is expected to have therapeutic synergistic effects in the treatment of cancer and reduce sides affects associated with these chemotherapeutic agents.

Examples of antibiotic agents useful in combination with the compounds disclosed herein include, but are not limited to, anthracyclines (e.g. doxorubicin, daunorubicin, epirubicin, idarubicin and anthracenedione), mitomycin C, bleomycin, dactinomycin, plicatomycin. These antibiotic agents interfere with cell growth by targeting different cellular components.

Antimetabolic agents useful in combination with the compounds disclosed herein include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Combination therapy including a compound disclosed herein and an antimetabolic agent is expected to have therapeutic synergistic effects on cancer and reduce sides affects associated with these chemotherapeutic agents.

Hormonal agents useful in combination with the compounds disclosed herein include synthetic estrogens (e.g. diethylstibestrol), antiestrogens (e.g. tamoxifen, toremifene, fluoxymesterol and raloxifene), antiandrogens (bicalutamide, nilutamide, and flutamide), aromatase inhibitors (e.g., aminoglutethimide, anastrozole and tetrazole), ketoconazole, goserelin acetate, leuprolide, megestrol acetate and mifepristone. Combination therapy including a compound disclosed herein and a hormonal agent is expected to have therapeutic synergistic effects on cancer and reduce sides affects associated with these chemotherapeutic agents. Plant-derived agents useful in combination with the compounds disclosed herein include, but are not limited to, vinca alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. Combination therapy including a compound disclosed herein and a plant-derived agent is expected to have therapeutic synergistic effects on cancer and reduce sides affects associated with these chemotherapeutic agents In any case, regardless of the disease, disorder or condition being treated, the overall benefit experienced by the patient is simply be additive of the two therapeutic agents or the patient experiences a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt thereof, is initiated prior to, during, or after treatment with a second agent described herein, and continues until any time during treatment with the second agent or after termination of treatment with the second agent. It also includes treatments in which a compound described herein, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, a compound described herein, or a pharmaceutically acceptable salt thereof, is administered in combination with chemotherapy, hormone blocking therapy, radiation therapy, monoclonal antibodies, or combinations thereof.

Chemotherapy includes the use of one or more anti-cancer agents.

EXAMPLES

The following examples are provided for illustrative purposes only and not to limit the scope of the claims provided herein.

Having now generally described the invention, the same will be more readily understood through reference to the following examples which are provided by way of illustration, and are not intended to be limiting of the present invention, unless specified.

Example 1: Synthesis of 2-(4-methyl-[1,4]diazepan-1-yl)-1,7,11b-triaza-benzo[c]fluorene-6-carboxylate sodium salt (Compound 1A)

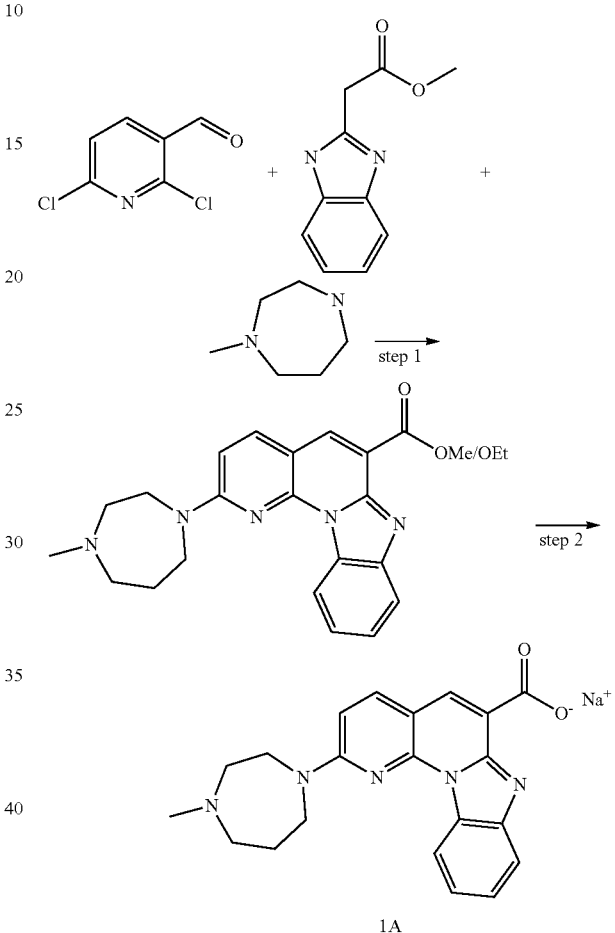

1A

Step 1: Synthesis of methyl 2-(4-methyl-[1,4]diazepan-1-yl)-1,7,11b-triazabenzo[c]fluorene-6-carboxylic acid and Ethyl 2-(4-methyl-[1,4]diazepan-1-yl)-1,7,11b-triazabenzo[c]fluorene-6-carboxylic acid.

To a suspension of 2,6-dichloronicotinaldehyde (3.55 g, 20.2 mmol) and methyl benzimidazole-2-acetate (3.82 g, 20.1 mmol, 1 eq.) in ethanol (50 mL) was added N-methylhomopiperazine (4.66 ml, 37.46 mmol) and the mixture was stirred at room temperature for 20 min. The reaction mixture was heated to reflux for 6 h. The mixture was then cooled to −20° C. and the precipitate collected by filtration to give a first crop of product (2.61 g). The filtrate was concentrated and the residue triturated with ethyl acetate (50 mL) to give a second crop (1.58 g). The filtrate was concentrated and the residue triturated with a mixture of methanol:water (20 mL, 1:1 v/v) to give a third (748 mg). The combined crops contained a mixture of the title compounds (4.94 g, 12.4 mmol, 61%) and were used without further purification. LCMS: 98% (8.8:1 OMe:OEt), Rt 1.434 min, ESMS m/z 390.1 (M+H)$^+$ (Me ester), Rt 1.575 min, ESMS m/z 404.1 (M+H)$^+$(Et ester).

Step 2: Synthesis of 2-(4-methyl-[1,4]diazepan-1-yl)-1,7,11b-triazabenzo[c]fluorene-6-carboxylic acid sodium salt (1A)

A suspension of methyl and ethyl 2-(4-methyl-[1,4]diazepan-1-yl)-1,7,11b-triaza-benzo[c]fluorene-6-carboxylic acid (combined products from the previous step, 2.77 g, 7.1 mmol) and sodium hydroxide (284 mg, 14.2 mmol, 2 eq.) in a mixture of water and 1,4-dioxane (30 mL, 1:1 v/v) was heated to 60° C. for 15 min. The mixture was cooled to room temperature and the precipitate collected. The solid was washed with acetonitrile (2×10 mL) and ether (2×10 mL) and air dried to yield the title compound (2.61 g, 6.6 mmol, 92%) as yellow solid. LCMS: 91%, Rt: 1.386 min, ESMS m/z 376.0 (M+H)+.

Example 2: Synthesis of 2-(4-methyl-[1,4]diazepan-1-yl)-1,7,11b-triazabenzo[c]fluorene-6-carboxylic acid isopropylamide (Compound 2A)

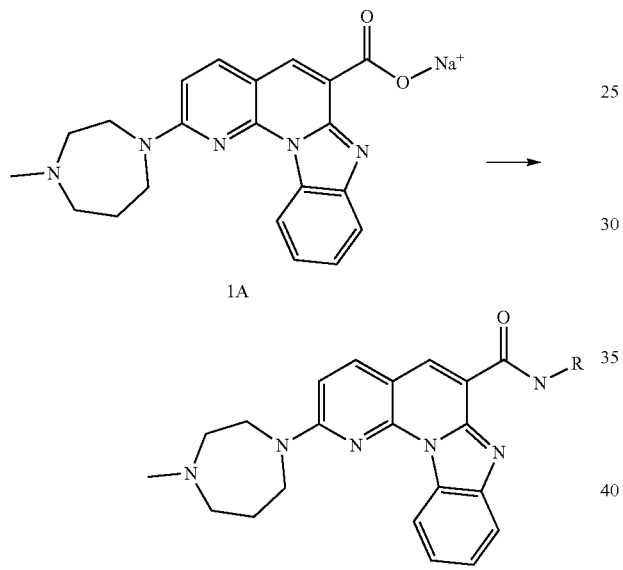

A mixture of 2-(4-methyl-[1,4]diazepan-1-yl)-1,7,11b-triazabenzo[c]fluorene-6-carboxylic acid sodium salt (1A, 127 mg, 0.32 mmol), isopropylamine (28 mg, 0.48 mmol, 1.5 eq.), 1-[bis(dimethylamino)methylene]-1H-1,2,3-triazolo[4,5-b]pyridinium 3-oxide hexafluorophosphate (HATU, 182 mg, 0.48 mmol, 1.5 eq.) and diisopropylethylamine (62 mg, 0.48 mmol, 1.5 eq.) in N,N-dimethylformamide (6.4 mL) was stirred at room temperature for 1 h.

The reaction mixture was poured into water (20 mL) and extracted with chloroform (3×10 mL). The combined organic layers were washed with saturated aqueous ammonium chloride (2×2 mL), water (10 mL) and brine (10 mL), dried over magnesium sulfate and evaporated. The residue was triturated with hexane (2 mL) to give the title compound (45 mg, 0.108 mmol, 34%) as a yellow crystalline solid.

LCMS: 92%, Rt: 1.886 min, ESMS m/z 417.2 (M+H)+. $^1$H NMR (300 MHz, CDCl$_3$) δ 10.51 (d, J=7.4 Hz, 1H), 8.99 (d, J=8.0 Hz, 1H), 8.63 (s, 1H), 7.98 (d, J=9.0 Hz, 1H), 7.95 (d, J=7.8 Hz, 1H), 7.57 (t, J=7.2 Hz, 1H), 7.46 (t, J=7.2 Hz, 1H), 6.72 (d, J=8.9 Hz, 1H), 4.43 (sex, J=6.7 Hz, 1H), 4.25-4.00 (m, 2H), 4.00-3.75 (m, 2H), 3.05-2.83 (m, 2H), 2.74-5.59 (m, 2H), 2.45 (s, 3H), 2.30-2.10 (m, 2H), 1.44 (d, J=6.6 Hz, 6H).

Example 3: Synthesis of 2-(4-Methyl-[1,4]diazepan-1-yl)-1,7,11b-triazabenzo[c]fluorene-6-carboxylic acid (1-cyclopropylethyl)-amide (Compound 2B)

A mixture of 2-(4-methyl-[1,4]diazepan-1-yl)-1,7,11b-triazabenzo[c]fluorene-6-carboxylic acid sodium salt (1A, 127 mg, 0.32 mmol), 1-cyclopropylethylamine (41 mg, 0.48 mmol, 1.5 eq.), 1-[bis(dimethylamino)methylene]-1H-1,2,3-triazolo[4,5-b]pyridinium 3-oxide hexafluorophosphate (HATU, 182 mg, 0.48 mmol, 1.5 eq.) and diisopropylethylamine (62 mg, 0.48 mmol, 1.5 eq.) in N,N-dimethylformamide (6.4 mL) was stirred at room temperature for 1 h.

The reaction mixture was poured into water (20 mL) and extracted with chloroform (3×10 mL). The combined organic layers were washed with saturated aqueous ammonium chloride (2×2 mL), water (10 mL) and brine (10 mL), dried over magnesium sulfate and evaporated. The residue was purified by silica gel column chromatography eluting with chloroform:methanol (100:0→90:10) to give the title compound (10 mg, 0.023 mmol, 7%) as a pale yellow crystalline solid.

LCMS: 97%, Rt: 1.926 min, ESMS m/z 443.1 (M+H)+. $^1$H NMR (300 MHz, CDCl$_3$) δ 10.59 (d, J=8.0 Hz, 1H), 8.87 (d, J=8.2 Hz, 1H), 8.61 (s, 1H), 7.96 (d, J=8.6 Hz, 1H), 7.94 (d, J=8.6 Hz, 1H), 7.58 (t, J=7.5 Hz, 1H), 7.44 (t, J=7.5 Hz, 1H), 6.71 (d, J=8.8 Hz, 1H), 4.40-4.09 (m, 2H), 3.99-3.72 (m, 3H), 3.31-3.04 (m, 2H), 3.04-2.78 (m, 2H), 2.61 (s, 3H), 2.52-2.28 (m, 2H), 1.46 (d, J=6.6 Hz, 3H), 1.23-1.06 (m, 1H), 0.65-0.44 (m, 3H), 0.41-0.28 (m, 1H).

Example 4: Synthesis of 2-(4-methyl-[1,4]diazepan-1-yl)-1,7,11b-triazabenzo[c]fluorene-6-carboxylic acid cyclopropylamide (Compound 2C)

A mixture of 2-(4-methyl-[1,4]diazepan-1-yl)-1,7,11b-triazabenzo[c]fluorene-6-carboxylic acid sodium salt (1A, 127 mg, 0.32 mmol), cyclopropylamine (27 mg, 0.48 mmol, 1.5 eq.), 1-[bis(dimethylamino)methylene]-1H-1,2,3-triazolo[4,5-b]pyridinium 3-oxide hexafluorophosphate (HATU, 182 mg, 0.48 mmol, 1.5 eq.) and diisopropylethylamine (62 mg, 0.48 mmol, 1.5 eq.) in N,N-dimethylformamide (6.4 mL) was stirred at room temperature for 1 h.

The reaction mixture was poured into water (20 mL) and extracted with chloroform (3×10 mL). The combined organic layers were washed with saturated aqueous ammonium chloride (4×2 mL), water (10 mL) and brine (10 mL), dried over magnesium sulfate and evaporated to give the title compound (25 mg, 0.060 mmol, 19%) as a yellow crystalline solid. LCMS: 95%, Rt: 1.747 min, ESMS m/z 415.3 (M+H)+. $^1$H NMR (300 MHz, CDCl$_3$) δ 10.58 (d, J=3.8 Hz, 1H), 8.88 (d, J=8.1 Hz, 1H), 8.60 (s, 1H), 7.96 (d, J=9.3 Hz, 1H), 7.93 (d, J=9.3 Hz, 1H), 7.55 (t, J=7.6 Hz, 1H), 7.44 (t, J=7.7 Hz, 1H), 6.69 (d, J=8.9 Hz, 1H), 4.32-4.02 (m, 2H), 3.99-3.75 (m, 2H), 3.18-2.94 (m, 3H), 2.91-2.72 (m, 2H), 2.54 (s, 3H), 2.42-2.23 (m, 2H), 1.04-0.91 (m, 2H), 0.88-0.74 (m, 2H).

Example 5: Synthesis of 2-(4-methyl-[1,4]diazepan-1-yl)-1,7,11b-triazabenzo[c]fluorene-6-carboxylic acid (tetrahydropyran-4-yl)-amide (Compound 2D)

A mixture of 2-(4-methyl-[1,4]diazepan-1-yl)-1,7,11b-triazabenzo[c]fluorene-6-carboxylic acid sodium salt (1A, 127 mg, 0.32 mmol), 4-aminotetrahydropyran (48 mg, 0.48 mmol, 1.5 eq.), 1-[bis(dimethylamino)methylene]-1H-1,2,3-triazolo[4,5-b]pyridinium 3-oxide hexafluorophosphate (HATU, 182 mg, 0.48 mmol, 1.5 eq.) and diisopropylethylamine (62 mg, 0.48 mmol, 1.5 eq.) in N,N-dimethylformamide (6.4 mL) was stirred at room temperature for 1 h.

The reaction mixture was poured into water (20 mL) and extracted with chloroform (3×10 mL). The combined organic layers were washed with saturated aqueous ammonium chloride (2×2 mL), water (10 mL) and brine (10 mL), dried over magnesium sulfate and evaporated. The residue was triturated with 1:1 hexane:ether (2 mL) to give the title compound (17 mg, 0.037 mmol, 12%) as a yellow crystalline solid. LCMS: 95%, Rt: 1.780 min, ESMS m/z 459.1 (M+H)$^+$. $^1$H NMR (300 MHz, CDCl$_3$-d) δ 10.76 (d, J=7.6 Hz, 1H), 8.94 (d, J=8.2 Hz, 1H), 8.61 (s, 1H), 7.97 (d, J=9.6 Hz, 1H), 7.93 (d, J=9.3 Hz, 1H), 7.56 (t, J=7.6 Hz, 1H), 7.45 (t, J=7.7 Hz, 1H), 6.71 (d, J=8.9 Hz, 1H), 4.48-4.28 (m, 1H), 4.21-3.99 (m, 4H), 3.99-3.81 (m, 2H), 3.75-3.57 (m, 2H), 3.10-2.88 (m, 2H), 2.82-2.63 (m, 2H), 2.48 (s, 3H), 2.35-2.20 (m, 2H), 2.17-2.07 (m, 2H), 1.96-1.74 (m, 2H).

Example 6: Synthesis of 2-(4-methyl-[1,4]diazepan-1-yl)-1,7,11b-triazabenzo[c]fluorene-6-carboxylic acid (5-methylpyrazin-2-ylmethyl)-amide (Compound 2E)

A mixture of 2-(4-methyl-[1,4]diazepan-1-yl)-1,7,11b-triazabenzo[c]fluorene-6-carboxylic acid sodium salt (1A, 127 mg, 0.32 mmol), 2-(aminomethyl)-5-methylpyrazine (59 mg, 0.48 mmol, 1.5 eq.), 1-[bis(dimethylamino)methylene]-1H-1,2,3-triazolo[4,5-b]pyridinium 3-oxide hexafluorophosphate (HATU, 182 mg, 0.48 mmol, 1.5 eq.) and diisopropylethylamine (62 mg, 0.48 mmol, 1.5 eq.) in N,N-dimethylformamide (6.4 mL) was stirred at room temperature for 16 h.

The reaction mixture was poured into water (20 mL) and the precipitate collected by filtration to give the title compound (23 mg, 0.048 mmol, 15%) as a yellow crystalline solid. LCMS: 96%, Rt: 1.712 min, ESMS m/z 481.3 (M+H)$^+$. $^1$H NMR (300 MHz, CDCl$_3$) δ 11.34-11.16 (m, 1H), 8.97 (d, J=8.1 Hz, 1H), 8.68 (s, 1H), 8.63 (s, 1H), 8.47 (s, 1H), 7.96 (d, J=8.6 Hz, 1H), 7.93 (d, J=8.6 Hz, 1H), 7.55 (t, J=7.6 Hz, 1H), 7.44 (t, J=7.7 Hz, 1H), 6.72 (d, J=9.0 Hz, 1H), 4.98 (d, J=5.6 Hz, 2H), 4.23-3.73 (m, 4H), 3.00-2.80 (m, 2H), 2.72-2.61 (m, 2H), 2.59 (s, 3H), 2.43 (s, 3H), 2.25-2.06 (m, 2H).

Example 7: Synthesis of 2-(4-Methyl-[1,4]diazepan-1-yl)-1,7,11b-triazabenzo[c]fluorene-6-carboxylic acid (3-methyloxetan-3-ylmethyl)-amide (Compound 2F)

A mixture of 2-(4-methyl-[1,4]diazepan-1-yl)-1,7,11b-triazabenzo[c]fluorene-6-carboxylic acid sodium salt (1A, 127 mg, 0.32 mmol), (3-methyloxetan-3-yl)methanamine (48 mg, 0.48 mmol, 1.5 eq.), 1-[bis(dimethylamino)methylene]-1H-1,2,3-triazolo[4,5-b]pyridinium 3-oxide hexafluorophosphate (HATU, 182 mg, 0.48 mmol, 1.5 eq.) and diisopropylethylamine (62 mg, 0.48 mmol, 1.5 eq.) in N,N-dimethylformamide (6.4 mL) was stirred at room temperature for 16 h.

The reaction mixture was poured into water (20 mL) and extracted with chloroform (3×10 mL). The combined organic layers were washed with saturated aqueous ammonium chloride (2×2 mL), water (10 mL) and brine (10 mL), dried over magnesium sulfate and evaporated to give the title compound (6 mg, 0.013 mmol, 4%) as a yellow crystalline solid. LCMS 99%, Rt: 1.836 min, ESMS m/z 459.1 (M+H)$^+$. $^1$H NMR (300 MHz, CDCl$_3$-d) δ 11.08-10.85 (m, 1H), 8.99 (d, J=8.1 Hz, 1H), 8.63 (s, 1H), 7.98 (d, J=8.9 Hz, 1H), 7.90 (d, J=8.1 Hz, 1H), 7.55 (t, J=7.6 Hz, 1H), 7.45 (t, J=7.7 Hz, 1H), 6.74 (d, J=8.9 Hz, 1H), 4.74 (d, J=6.0 Hz, 2H), 4.47 (d, J=5.9 Hz, 2H), 4.33-3.65 (m, 4H), 3.86 (d, J=6.0 Hz, 2H), 3.00-2.83 (m, 2H), 2.74-2.56 (m, 2H), 2.43 (s, 3H), 2.28-2.11 (m, 2H), 1.52 (s, 3H).

Example 8: Synthesis of 2-(4-methyl-[1,4]diazepan-1-yl)-1,7,11b-triazabenzo[c]fluorene-6-carboxylic acid methylamide (Compound 2G)

A mixture of 2-(4-methyl-[1,4]diazepan-1-yl)-1,7,11b-triazabenzo[c]fluorene-6-carboxylic acid sodium salt (1A, 99 mg, 0.25 mmol), methylamine hydrochloride (25 mg, 0.38 mmol, 1.5 eq.), 1-[bis(dimethylamino)methylene]-1H-1,2,3-triazolo[4,5-b]pyridinium 3-oxide hexafluorophosphate (HATU, 144 mg, 0.38 mmol, 1.5 eq.) and diisopropylethylamine (49 mg, 0.38 mmol, 1.5 eq.) in N,N-dimethylformamide (5.0 mL) was stirred at room temperature for 1 h.

The reaction mixture was poured into water (8 mL) and cooled to 4° C. for 16 h. The precipitate was collected and washed with 4:1 water: N,N-dimethylformamide (1 mL) and water (1 mL). The solid was suspended in water (200 μL) and 20% aqueous sodium carbonate (200 μL) was added. The mixture was stirred at room temperature for 1 h, the solid was collected and washed with water (3×1 mL) to give the title compound (16 mg, 0.041 mmol, 16%) as a yellow crystalline solid. LCMS: 100%, Rt: 1.678 min, ESMS m/z 389.1 (M+H)$^+$. $^1$H NMR (300 MHz, CDCl$_3$-d) δ 10.56-10.34 (m, 1H), 8.99 (d, J=8.1 Hz, 1H), 8.64 (s, 1H), 7.96 (d, J=9.0 Hz, 2H), 7.95 (d, J=7.8 Hz, 1H), 7.57 (t, J=7.8 Hz, 1H), 7.47 (t, J=7.8 Hz, 1H), 6.71 (d, J=9.0 Hz, 1H), 4.41-3.69 (m, 4H), 3.21 (d, J=4.8 Hz, 3H), 3.00-2.81 (m, 2H), 2.74-2.58 (m, 2H), 2.44 (s, 3H), 2.27-2.07 (m, 2H).

Example 9: Synthesis of 2-((3S,5R)-3,5-dimethylpiperazin-1-yl)-1,7,11b-triaza-benzo[c]fluorene-6-carbonitrile (Compound 3A)

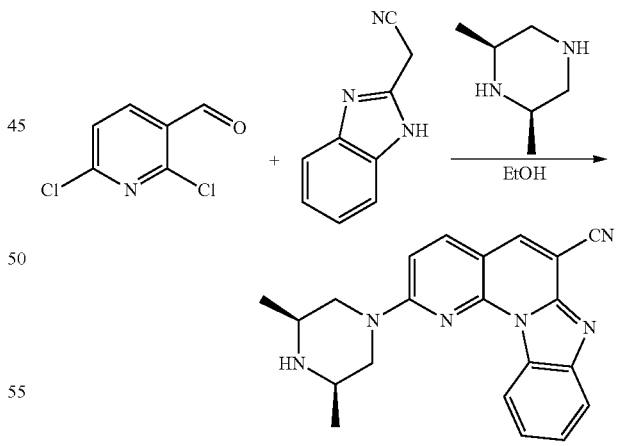

To a suspension of 2,6-dichloronicotinaldehyde (100 mg, 0.568 mmol) and methyl benzimidazole-2-acetate (89.5 mg, 0.568 mmol, 1 eq.) in ethanol (1.5 mL) was added cis-2,6-dimethylpiperazine (120.8 mg, 1.058 mmol) and the mixture was heated to 75° C. for 24 hours.

The mixture was then cooled to room temperature and the precipitate collected by filtration, washed with ethyl acetate and small amount of methanol, and dried under vacuum to give orange solid (42 mg).

Example 10: Synthesis of 2-(4-ethylpiperazin-1-yl)-1,7,11b-triaza-benzo[c]fluorene-6-carbonitrile (Compound 3B)

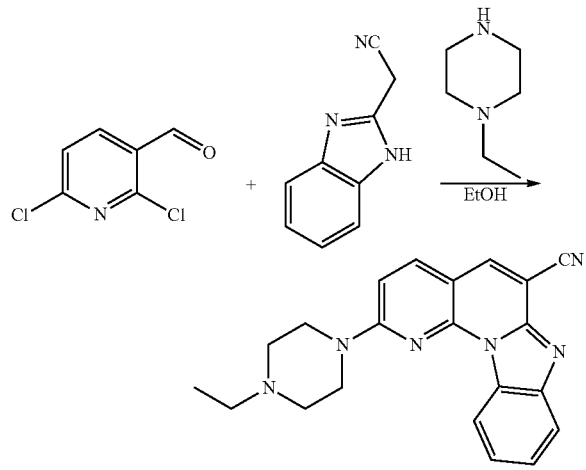

To a suspension of 2,6-dichloronicotinaldehyde (100 mg, 0.568 mmol) and methyl benzimidazole-2-acetate (89.5 mg, 0.568 mmol, 1 eq.) in ethanol (1.5 mL) was added 1-ethylpiperazine (120.8 mg, 1.058 mmol) and the mixture was heated to 75° C. for 24 hours.

The mixture was then cooled to room temperature and the precipitate collected by filtration, washed with ethyl acetate and small amount of methanol and dried under vacuum to give orange solid (45 mg).

Example 11: Synthesis of Ethyl 1H-benzimidazol-2-yacetate

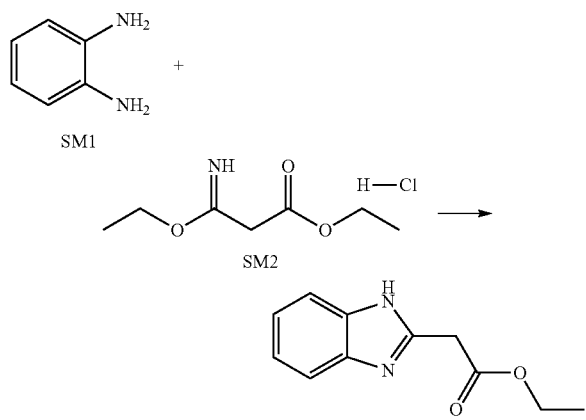

A mixture of SM1 (40 g, 370 mmol) and SM2 (73 g, 373 mmol) in ethanol (200 ml) was stirred at 90° C. overnight. The reaction was cooled to room temperature and the solvent was removed in vacuo. Water (300 ml) and DCM (500 ml) were added to the residue. The organic layer was separated, dried over $Na_2SO_4$ and the solvent removed to give Ethyl 1H-benzimidazol-2-yacetate (40 g, 53% yield) as a pale yellow solid.

Example 12: Synthesis of Ethyl 2-(4-methyl-[1,4]diazepan-1-yl)-1,7,11b-triazabenzo[c]fluorene-6-carboxylic acid

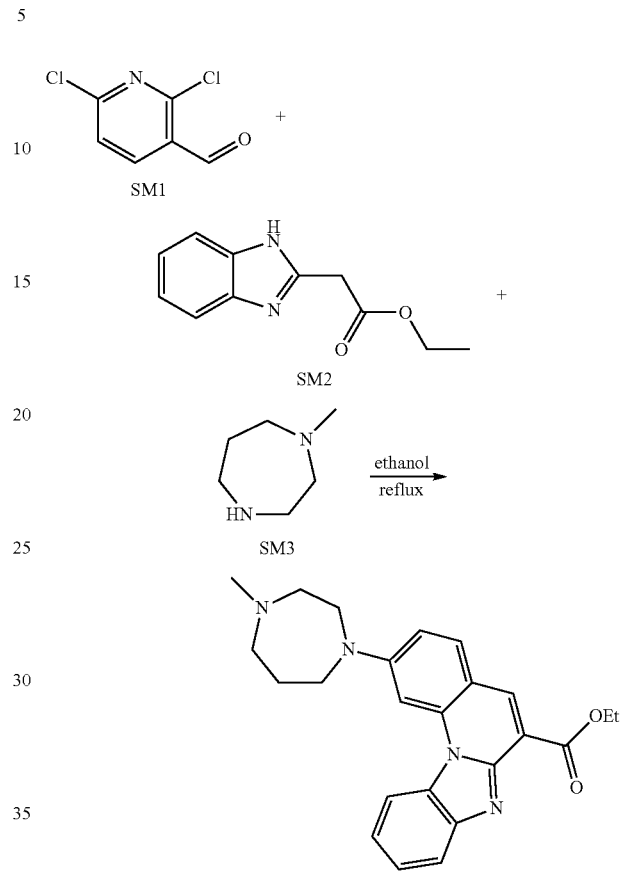

To a suspension of SM1 (25.9 g, 148 mmol) and SM2 (30 g, 147 mmol) in ethanol (400 mL) was added SM3 (33.5 g, 394 mmol) and the mixture was stirred at room temperature for 20 min. The reaction mixture was heated to reflux for 6 h. The mixture was then cooled to 20° C. and the precipitate collected by filtration to give Ethyl 2-(4-methyl-[1,4]diazepan-1-yl)-1,7,11b-triazabenzo[c]fluorene-6-carboxylic acid (40 g, 68% yield) as a pale yellow solid. LCMS

Example 13: Synthesis of 2-(4-methyl-[1,4]diazepan-1-yl)-1,7,11b-triazabenzo[c]fluorene-6-carboxylic acid

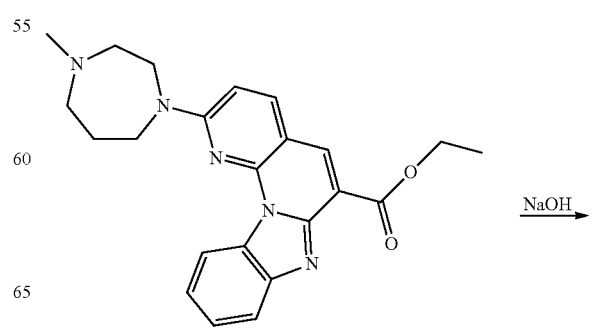

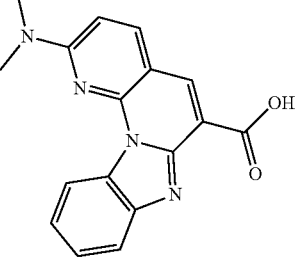

A suspension of Ethyl 2-(4-methyl-[1,4]diazepan-1-yl)-1,7,11b-triazabenzo[c]fluorene-6-carboxylic acid (1.2 g, 3.0 mmol) and sodium hydroxide (238 mg, 6.0 mmol) in a mixture of water and 1,4-dioxane (10 mL, 1:1 v/v) was heated to 60° C. for 30 min. The mixture was concentrated under reduced pressure. The mixture was acidified to pH 6 by addition of 1 M hydrochloric acid and evaporated to give the product (1.0 g, yield=89%), as a yellow crystalline solid.

Example 14: Synthesis of Compound 4A

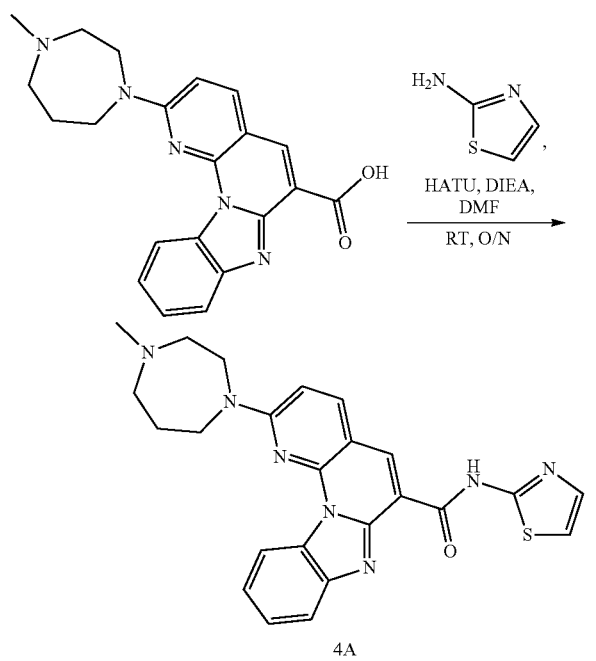

4A

A mixture of 2-(4-methyl-[1,4]diazepan-1-yl)-1,7,11b-triazabenzo[c]fluorene-6-carboxylic acid (150 mg, 0.4 mmol), thiazol-2-amine (60 mg, 0.6 mmol), HATU (228 mg, 0.6 mmol) and diisopropylethylamine (158 mg, 1.2 mmol) in N,N-dimethylformamide (5 mL) was stirred at room temperature over night. The yellow precipitate was collected and washed with ethyl alcohol and diethyl ether to give the crude product.

This material was dissolved in 2 M aqueous sodium hydroxide (20 mL) and extracted with dichloromethane (100 mL, then 20 mL). The combined organic layers were dried over magnesium sulfate and evaporated. The residue was triturated with diethyl ether (30 mL) and washed with diethyl ether to give the title compound (30 mg) as a yellow crystalline solid.

Example 15: Synthesis of Compound 4B

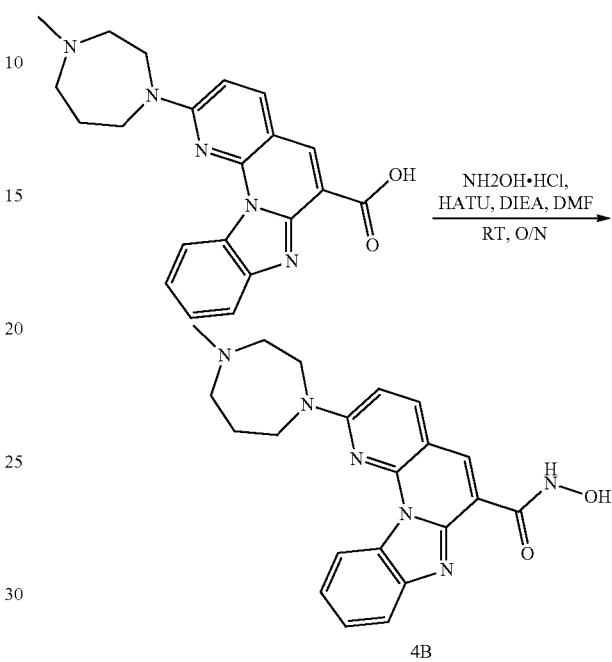

4B

Compound 4B was synthesized according to the procedure of 4A.

Example 16: Synthesis of Compound 4C

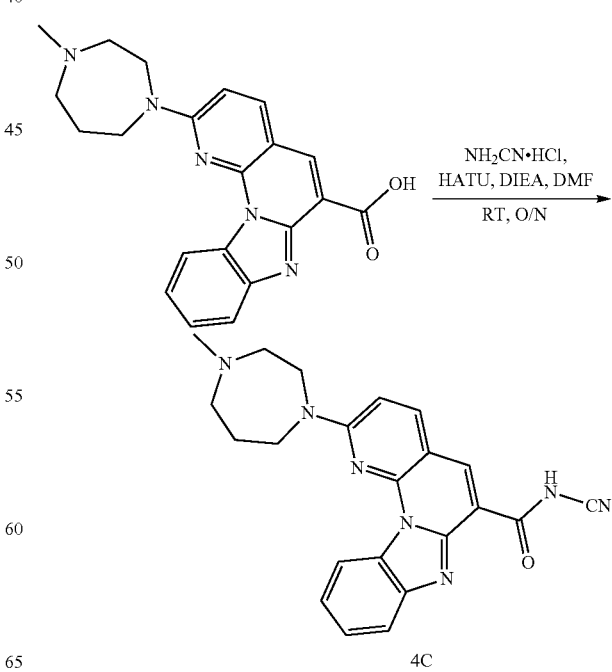

4C

Compound 4C was synthesized according to the procedure of 4A.

Example 17: Synthesis of Compound 5A

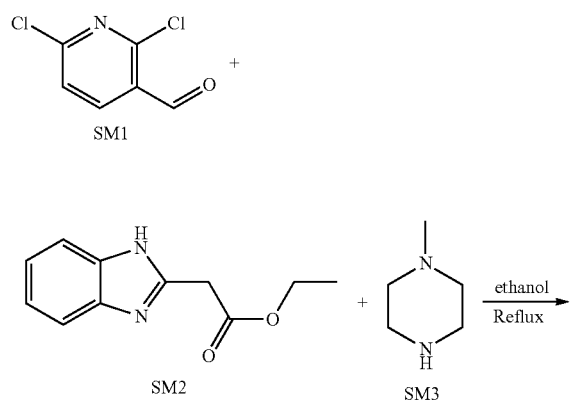

To a suspension of SM1 (4.32 g, 25.0 mmol) and SM2 (5.0 g, 25.0 mmol) in ethanol (100 mL) was added SM3 (4.9 g, 50.0 mmol) and the mixture was stirred at room temperature for 20 min. The reaction mixture was heated to reflux for 6 h. The mixture was then cooled to 20° C. and the precipitate collected by filtration, washed with EtOH, Et₂O and dried to give compound 5A (5.0 g, yield=50%, Lot #: MC13021-014-03) as a pale yellow solid. LCMS: m/z 390 (M+H)⁺.

Example 18: Synthesis of Compound 5B

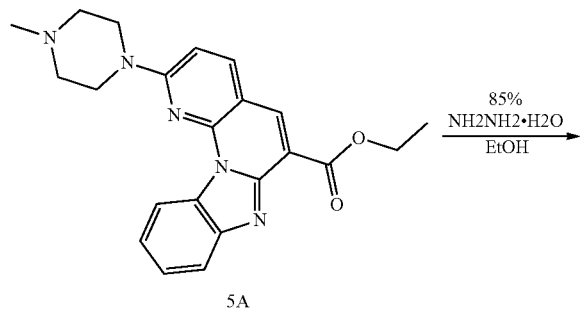

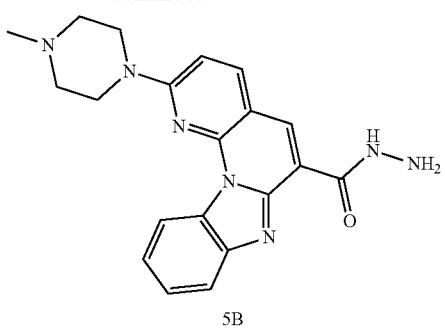

A suspension of compound 5A (100 mg, 0.257 mmol) and 85% NH₂NH₂·H₂O (300 mg, 5.0 mmol) in EtOH (20 ml) was heated to reflux for 6 h. The mixture was then cooled to 20° C. and the precipitate collected by filtration, washed with EtOH and dried to give compound 5B (40 mg, yield=41%) as a pale yellow solid. LCMS: m/z 376 (M+H)⁺.

Example 19: Synthesis of Compound 5C

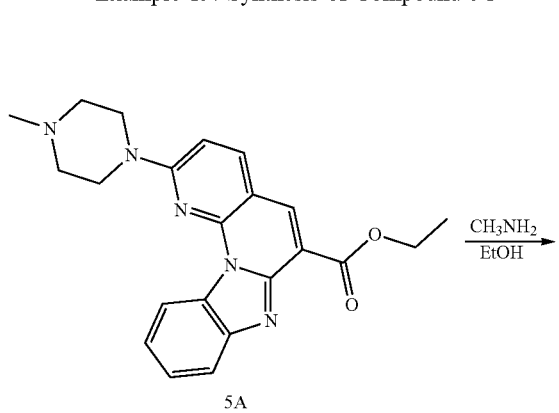

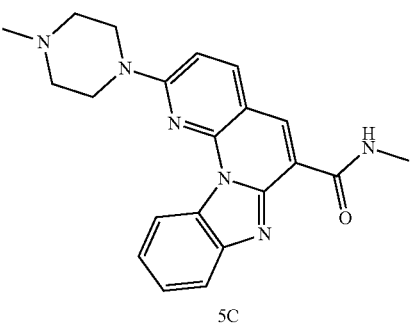

A suspension of compound 5A (100 mg, 0.257 mmol) in CH₃NH₂/EtOH (2M, 20 ml, 40 mmol) was heated to reflux for 6 h. The mixture was then cooled to 20° C. and the precipitate collected by filtration, washed with EtOH and dried. The yellow solid was dissolved in DCM (100 ml) and it was washed with water (3 times), brine, dried and concentrated to give compound 5C (20 mg, yield=21%) as a pale yellow solid.

Example 20: Synthesis of Compound 5D

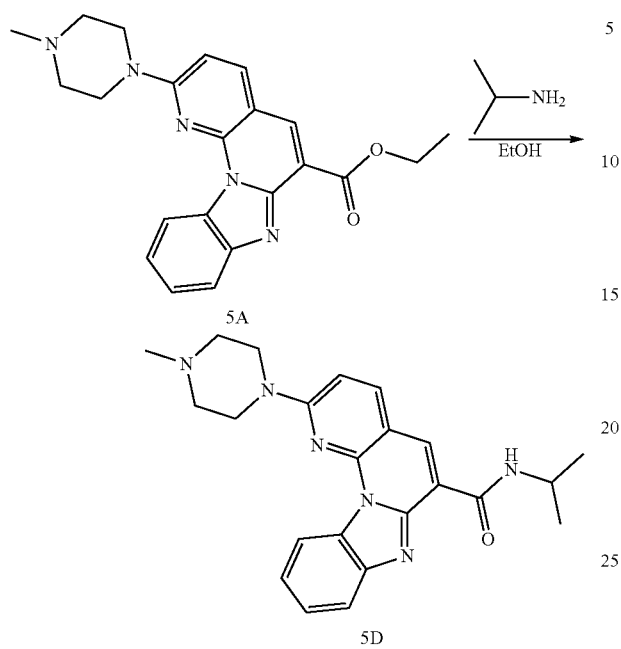

A suspension of compound 5A (100 mg, 0.257 mmol) and propan-2-amine (295 mg, 5.0 mmol) in EtOH (20 ml) was heated to reflux for 6 h. The mixture was then cooled to 20° C. and the precipitate collected by filtration, washed with EtOH and dried to give compound 5D (20 mg, yield=19%) as a pale yellow solid. LCMS: m/z 403.3 (M+H)+.

Example 21: Synthesis of Compound 2G

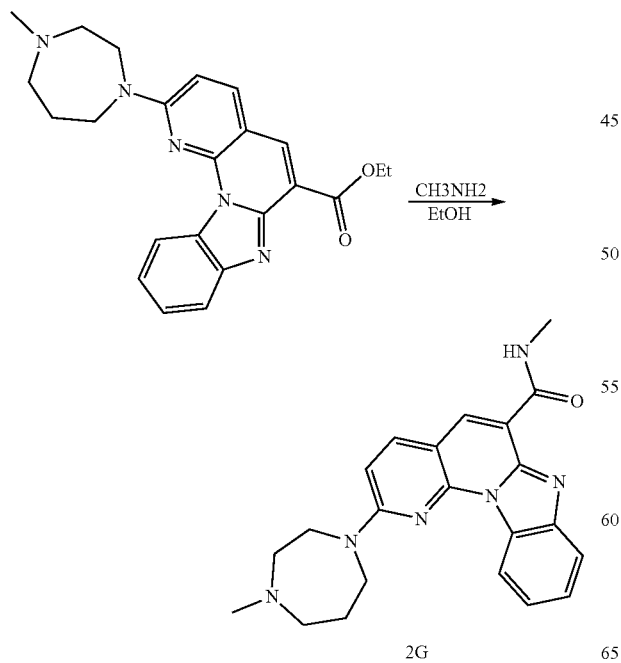

A suspension of Ethyl 2-(4-methyl-[1,4]diazepan-1-yl)-1,7,11b-triazabenzo[c]fluorene-6-carboxylic acid (40 g, 99 mmol) in $CH_3NH_2$/EtOH (2M, 400 ml, 800 mmol) was heated to reflux for 6 h. The mixture was then cooled to 20° C. and the precipitate was collected by filtration to give crude 2G as a pale yellow solid (35 g, 86% yield). The crude product was dissolved in DCM (500 ml) and washed with water (3 times), brine, dried and concentrated to give 2G (30.2 g, yield=78%) as a pale yellow solid.

1H NMR (400 MHz, DMSO-d6) δ 10.18 (1H, d, J=4.8 Hz), 8.91 (1H, d, J=6.0 Hz), 8.58 (1H, s), 8.25 (1H, d, J=8.8 Hz), 7.91 (1H,d, J=8.0 Hz), 7.55 (1H, t, J=7.6 Hz), 7.47 (1H, t, J=7.6 Hz), 6.99 (1H, d, J=88 Hz), 4.06~3.95 (4H, m), 3.03 (3H, d, J=4.8 Hz), 2.79~2.76 (2H, m), 2.50 (2H, m), 2.28 (3H, s), 2.02 (2H, br s). LC-MS: Rt=9.160 min, 389.5[M+H]+.

Example 22: Synthesis of 2-(4-Methyl-[1,4]diazepan-1-yl)-1,7,11b-triaza-benzo[c]fluorene-6-carbonitrile (Compound 3C)

To a solution of compound SM1 (100 mg, 0.568 mmol) and compound SM2 (90 mg, 0.568 mmol) in 2-Methoxyethanol (10 mL) was added N-Methylhomopiperazine (130 mg, 1.136 mmol) and the mixture was stirred at room temperature for 20 min. The reaction mixture was heated to reflux for 16 h. The mixture was then cooled to 20° C. and the precipitate collected by filtration, washed with EtOH, Et2O, dried and purified by Pre-HPLC to give 3C (15 mg) as a pale yellow solid. LCMS: m/z 357 (M+H)+.

Example 23: Synthesis of 2-[1,4]Diazepan-1-yl-1,7,11b-triaza-benzo[c]fluorene-6-carbonitrile (Compound 3D)

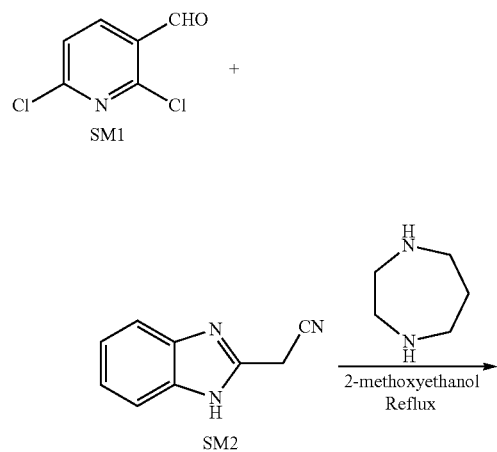

Compound 3D was synthesized as pale yellow solid (20 mg) according to the procedure of compound 3C. LCMS: m/z 342.9 (M+H)+.

Example 24: Synthesis of 2-(2-Morpholin-4-yl-ethylamino)-1,7,11b-triaza-benzo[c]fluorene-6-carbonitrile (Compound 3E)

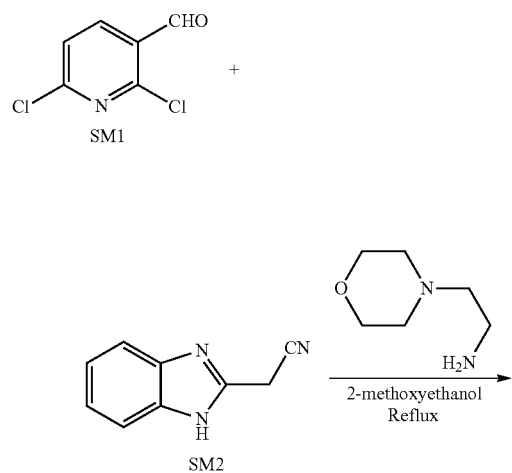

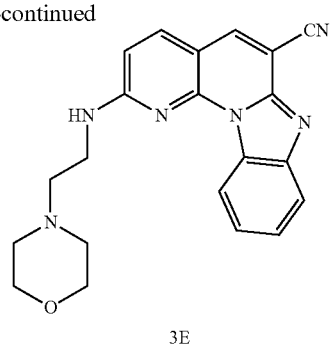

Compound 3E was synthesized as pale yellow solid (16 mg) according to the procedure of compound 3C. LCMS: m/z 373 (M+H)+.

Example 25: Synthesis of 2-(3-Dimethylamino-pyrrolidin-1-yl)-1,7,11b-triaza-benzo[c]fluorene-6-carbonitrile (Compound 3F)

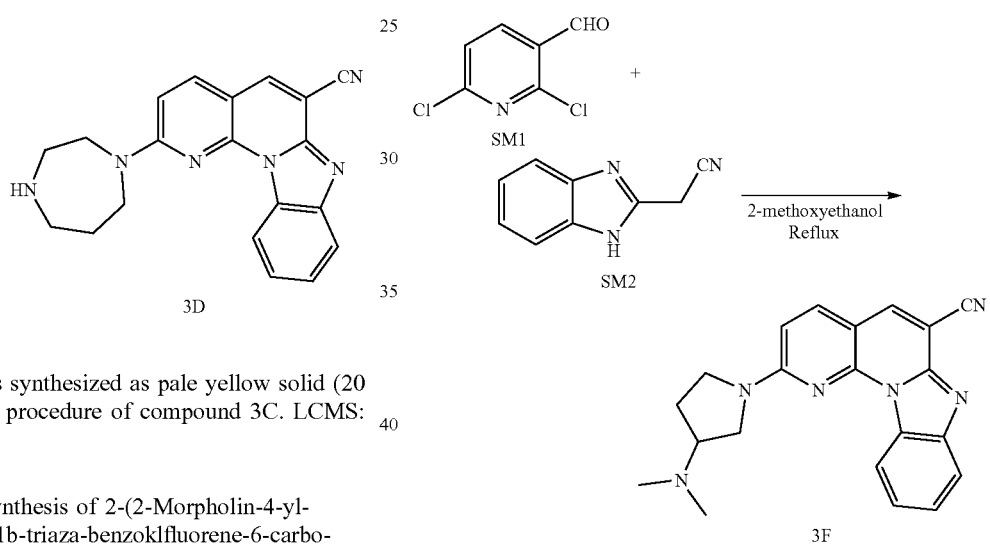

Compound 3F was synthesized as pale yellow solid (15 mg) according to the procedure of compound 3C. LCMS: m/z 357 (M+H)+.

Example 26: Synthesis of 2-(2-Imidazol-1-yl-ethylamino)-1,7,11b-triaza-benzo[c]fluorene-6-carbonitrile (Compound 3G)

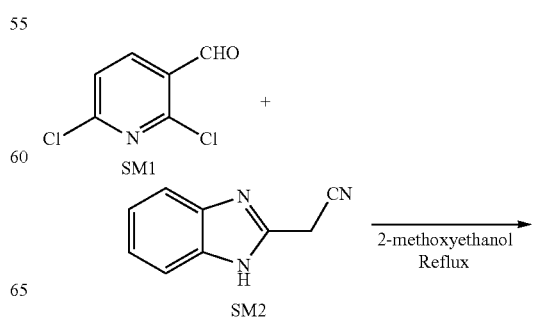

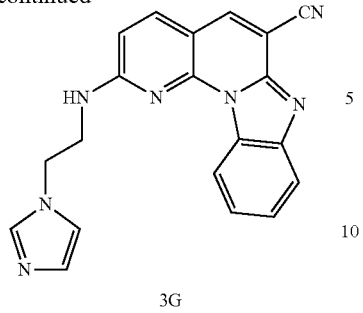

3G

Compound 3G was synthesized as pale yellow solid (12 mg) according to the procedure of compound 3C. LCMS: m/z 354 (M+H)+.

Example 27: Synthesis of 2-(4-Methyl-piperazin-1-yl)-1,7,11b-triaza-benzo[c]fluorene-6-carbonitrile (3H)

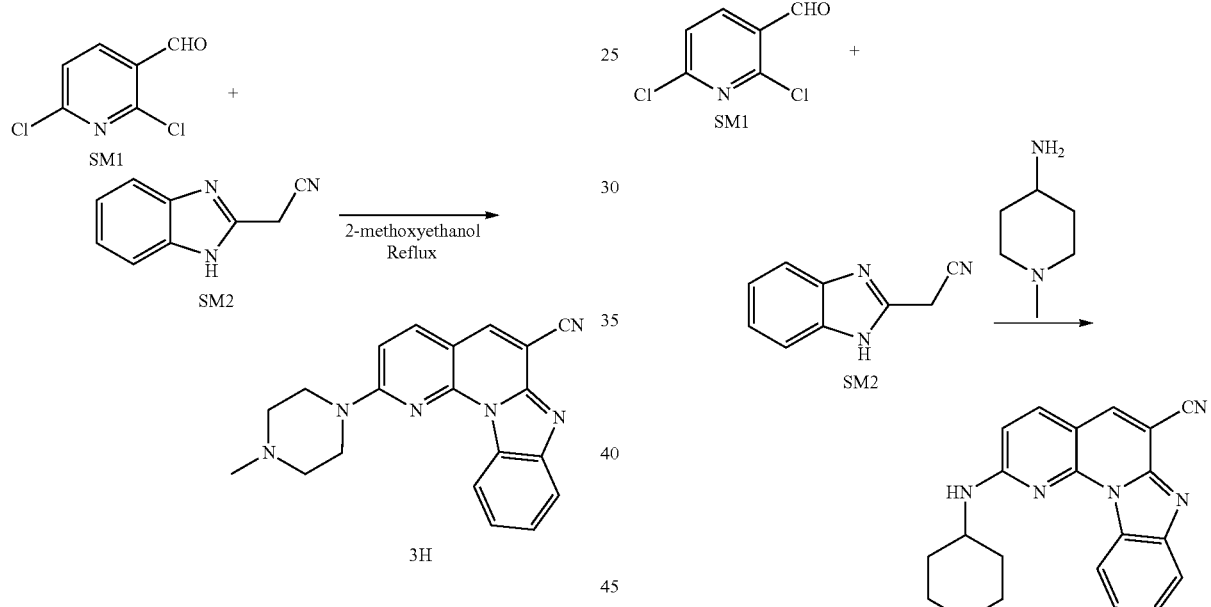

3H

Compound 3H was synthesized as pale yellow solid (30 mg) according to the procedure of compound 3C. LCMS: m/z 342.9 (M+H)+.

Example 28: Synthesis of 2-(2-Methoxy-ethyl-amino)-1,7,11b-triaza-benzo[c]fluorene-6-carbonitrile (Compound 3I)

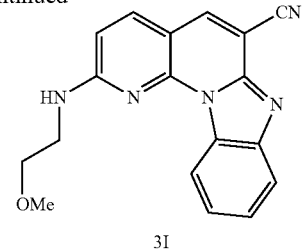

3I

Compound 3I was synthesized as pale yellow solid (15 mg) according to the procedure of compound 3C. LCMS: m/z 318 (M+H)+.

Example 29: Synthesis of 2-(1-Methyl-piperidin-4-ylamino)-1,7,11b-triaza-benzo[c]fluroene-6-carbonitrile (Compound 3J)

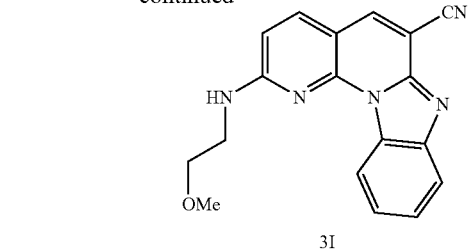

3J

Compound 3J was synthesized as pale yellow solid (7 mg) according to the procedure of compound 3C. LCMS: m/z 357 (M+H)+.

Example 30: Synthesis of 2-(2-Dimethylamino-ethylamino)-1,7,11b-triaza-benzo[c]fluorene-6-carbonitrile (Compound 3K)

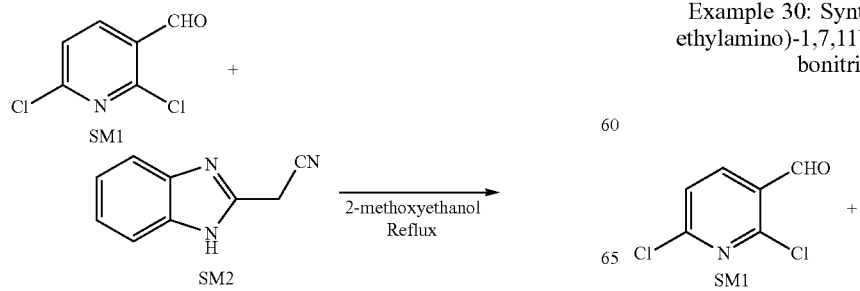

-continued

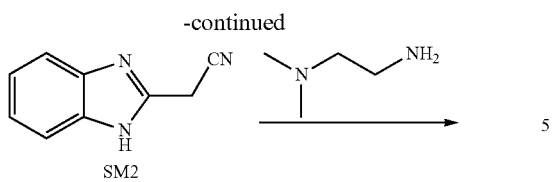

Compound 3K was synthesized as pale yellow solid (7 mg) according to the procedure of compound 3C. LCMS: m/z 331 (M+H)+.

Example 31: Synthesis of 2-(4-Methyl-[1,4]diaz-epan-1-yl)-1,7,11b-triaza-benzo[c]fluorene-6-carboxylic acid N'-methyl-hydrazide (Compound 4D)

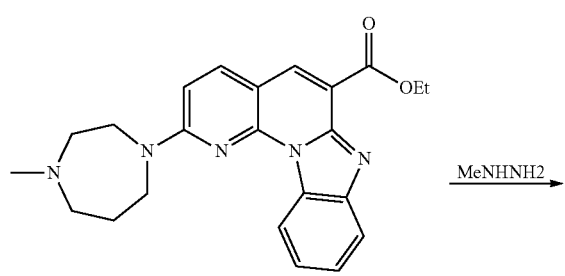

To a solution of 2-(4-Methyl-[1,4]diazepan-1-yl)-1,7,11b-triaza-benzo[c]fluorene-6-carboxylic acid ethyl ester (100 mg, 0.25 mmol) in ethanol (10 mL) was added methylhydrazine (288 mg, 40% aquous solution, 2.5 mmol) and the mixture was stirred at room temperature for 20 min. The reaction mixture was heated to reflux for 12 hrs. The mixture was then cooled to 20° C., concentrated and washed with water and methanol, dried to give compound 4D (20 mg, yield=20%) as yellow solid. LCMS: m/z 404 (M+H)+.

Example 32: Synthesis of 2-(4-Methyl-[1,4]diaz-epan-1-yl)-1,7,11b-triaza-benzo[c]fluorene-6-carboxylic acid (Compound 1A)

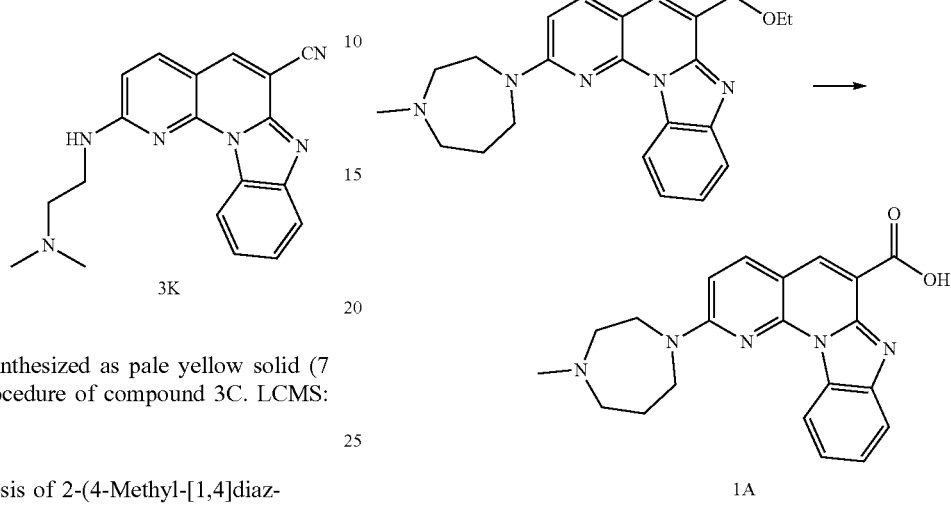

A suspension of 2-(4-Methyl-[1,4]diazepan-1-yl)-1,7,11b-triaza-benzo[c]fluorene-6-carboxylic acid ethyl ester (1.2 g, 3.0 mmol) and 2N NaOH (aq., 3 mL, 6.0 mmol) in a mixture of water and EtOH (10 mL, 1:1 v/v) was heated to 60° C. for 30 min. The mixture was concentrated under reduced pressure. The mixture was acidified to pH 6 by addition of 2 N HCl and stirred at r.t. for 30 min, the mixture was filtered and washed with water and ethanol, dried to give the desired product as a yellow solid (1.0 g, 89% yield). LCMS: m/z 376 (M+H)+.

Example 33: Synthesis of 2-(4-Methyl-[1,4]diaz-epan-1-yl)-1,7,11b-triaza-benzo[c]fluorene-6-carboxylic acid methyl-d3-amide (Compound 4E)

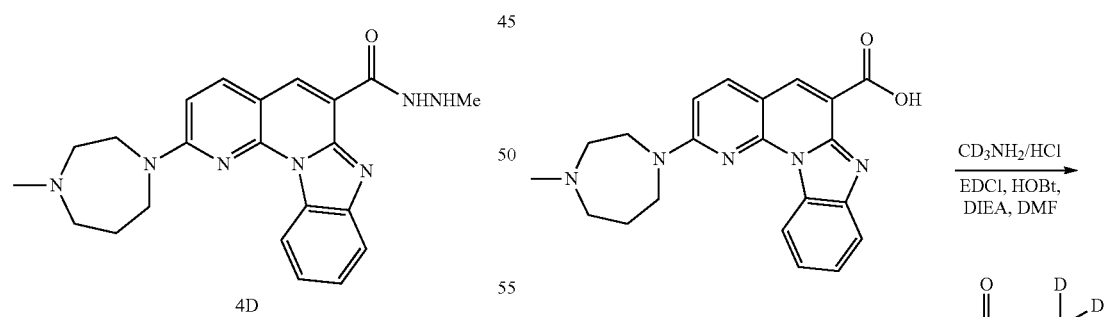

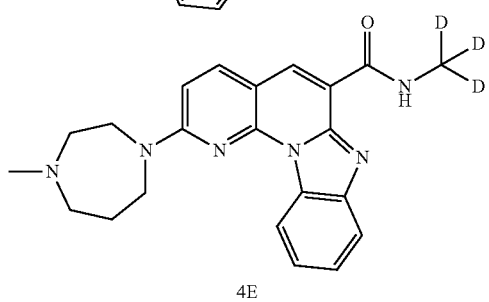

Example 34: Synthesis of 2-(4-Methyl-[1,4]diazepan-1-yl)-1,7,11b-triaza-benzo[c]fluorene-6-carboxylic acid methoxy-amide (Compound 4F)

Compound 4E was synthesized as yellow solid (40 mg) according to the procedure of compound 4A. LCMS: m/z 392.6 (M+H)+.

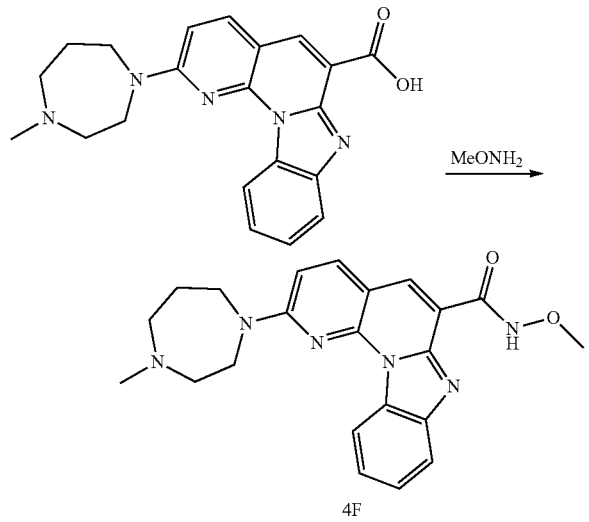

Compound 4F was synthesized as yellow solid (14 mg) according to the procedure of compound 4A. LCMS: m/z 305 (M+H)+.

Example 35: Synthesis of 1,1-Dimethyl-4-(6-methylcarbamoyl-1,7,11b-triaza-benzo[c]fluoren-2-yl)-[1,4]diazepan-1-ium; iodide (Compound 6A)

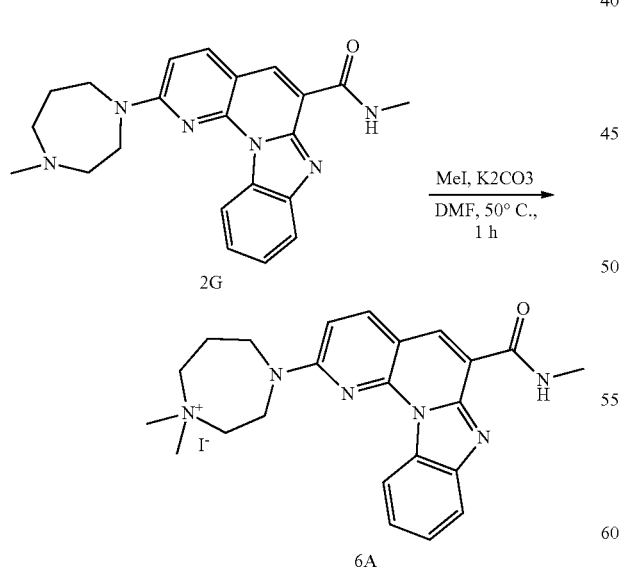

To a mixture of compound 2G (25 mg, 0.064 mmol), and K₂CO₃ (18 mg, 0.128 mmol) in N,N-dimethylformamide (2 mL) was added MeI (11 mg, 0.076 mmol) and stirred at 50° C. for 1 h. After cooling, the mixture was filtered and the filtrate was purified by Pre-HPLC to give the title compound 6A (16 mg, 47% yield) as yellow solid. LCMS: m/z 403.7 (M+H)+.

Example 36: Synthesis of 2-(4-Methyl-piperazin-1-yl)-1,7,11b-triaza-benzo[c]fluorene-6-carboxylic acid cyclopropylamide (Compound 5A)

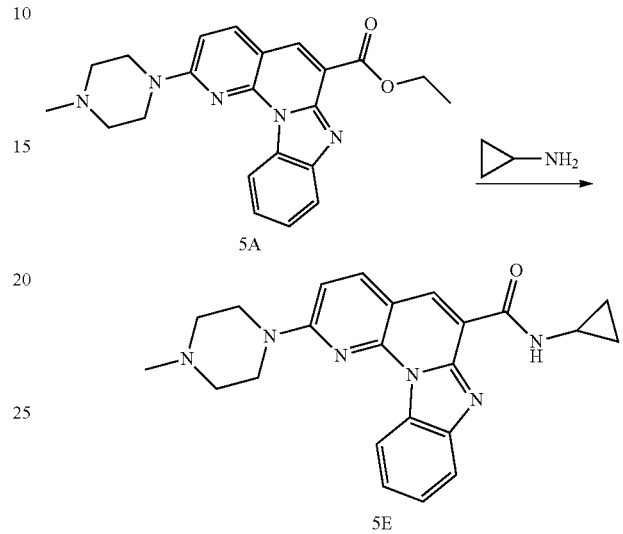

Compound 5E was synthesized as yellow solid (25 mg) according to the procedure of compound 4D. LCMS: m/z 401 (M+H)+.

Example 37: Synthesis of 3-Fluoro-1,7,11b-triaza-benzo[c]fluorene-6-carboxylic acid ethyl ester (Compound 7A)

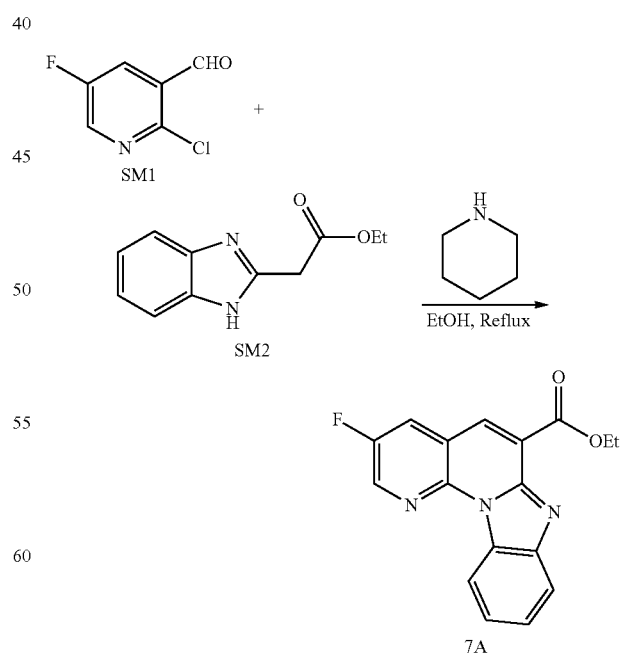

To a solution of compound SM1 (0.8 g, 5 mmol) and compound SM2 (1.02 g, 5 mmol) in ethanol (50 mL) was added piperidine (1.28 g, 15 mmol) and the mixture was stirred at room temperature for 20 min. The reaction mixture was heated to reflux for 16 h. After cooling, the mixture was filtered and washed with ethanol, dried to get compound 7A as yellow solid (0.82 g, 79% yield). LCMS: m/z 309.9 (M+H)+.

Example 38: Synthesis of 3-Fluoro-1,7,11b-triaza-benzo[c]fluorene-6-carboxylic acid (Compound 7B)

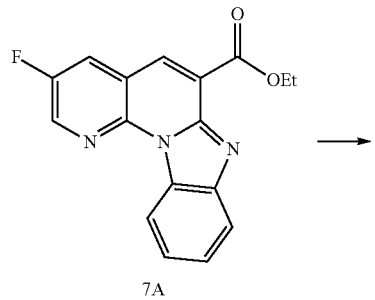

7A

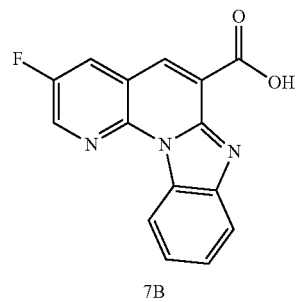

7B

Compound 7B was synthesized as yellow solid (320 mg) according to the procedure of compound 1A. LCMS: m/z 281.9 (M+H)+.

Example 39: Synthesis of (3-Fluoro-1,7,11b-triaza-benzo[c]fluoren-6-yl)-(4-methyl-[1,4]diazepan-1-yl)-methanone (Compound 7C)

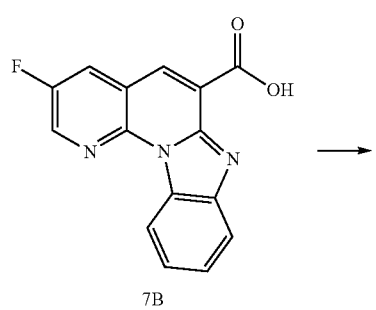

7B

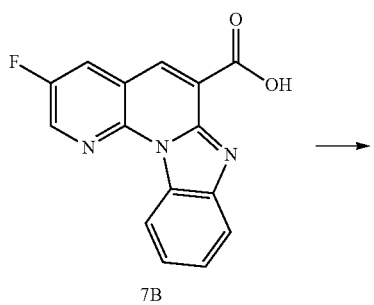

7C

Compound 7C was synthesized as yellow solid (20 mg) according to the procedure of compound 4A. LCMS: m/z 378.5 (M+H)+.

Example 40: Synthesis of [1,4]Diazepan-1-yl-(3-fluoro-1,7,11b-triaza-benzo[c]fluoren-6-yl)-methanone (Compound 7D)

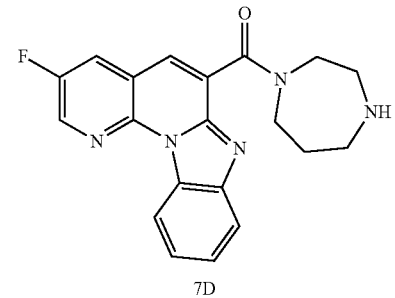

7B

7D

A mixture of 7B (45 mg, 0.16 mmol), N-Boc-homopiperazine (64 mg, 0.32 mmol), HOBt (43.2 mg, 0.32 mmol), DIEA (103.8 mg, 0.81 mmol) and EDCI.HCl (62 mg, 0.32 mmol) in N,N-dimethylformamide (5 mL) was stirred at room temperature overnight. This material was dissolved in water (20 ml) and extracted with 10% MeOH in DCM (20 mL). The organic layers were dried over magnesium sulfate and evaporated. The residue was dissolved in MeOH (5 mL) and 4N HCl (0.5 mL) was added and the mixture was stirred at r.t. for 4 h. The mixture was adjusted to pH~8 by sat. NaHCO$_3$, filtered, washed with ether to give compound 7D as pale yellow solid (40 mg, 68% yield). LCMS: m/z 364.5 (M+H)+.

Example 41: Synthesis of 3-Fluoro-1,7,11b-triaza-benzo[c]fluorene-6-carboxylic acid (1-methyl-piperidin-4-yl)-amide (Compound 7E)

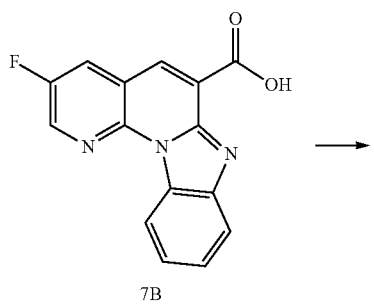

7B

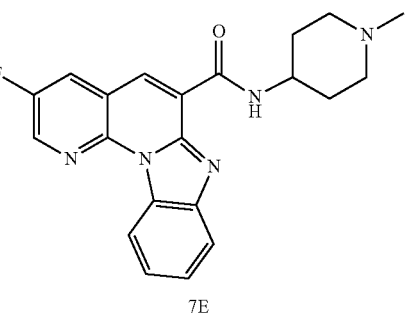

7E

Compound 7E was synthesized as yellow solid (32 mg) according to the procedure of compound 4A. LCMS: m/z 378.5 (M+H)+.

Example 42: Synthesis of 3-Fluoro-1,7,11b-triaza-benzo[c]fluorene-6-carboxylic acid (2-dimethyl-amino-ethyl)-amide (Compound 7F)

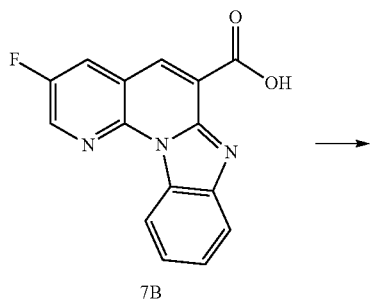

7B

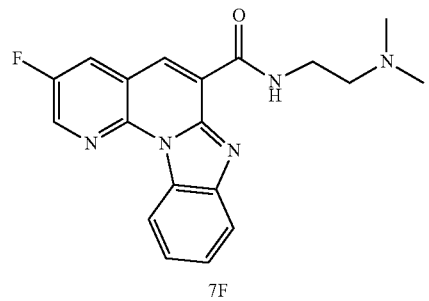

7F

A solution of 7B (50 mg, 0.16 mmol) and N1,N1-dimethylethane-1,2-diamine (295 mg, 5.0 mmol) in EtOH (10 ml) was heated to reflux for 16 h. The mixture was then cooled to r.t., filtered and washed by ether, dried to give compound 7F (20 mg, 35% yield) as a pale yellow solid. LCMS: m/z 352.4 (M+H)+.

Example 43: Synthesis of 3-Fluoro-1,7,11b-triaza-benzo[c]fluorene-6-carboxylic acid (2-morpholin-4-yl-ethyl)-amide (Compound 7G)

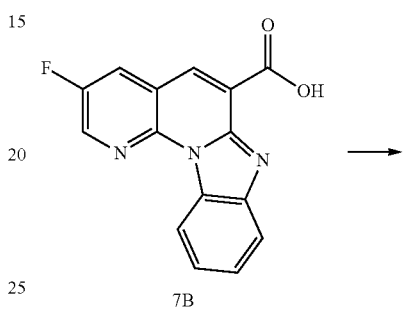

7B

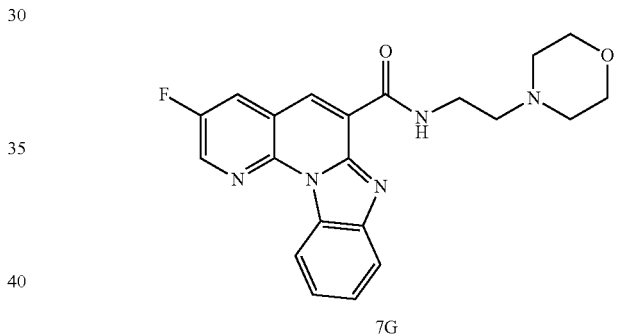

7G

Compound 7G was synthesized as yellow solid (24 mg) according to the procedure of compound 7F. LCMS: m/z 394 (M+H)+.

Example 44: Synthesis of 3-Fluoro-1,7,11b-triaza-benzo[c]fluorene-6-carboxylic acid (2-pyrrolidin-1-yl-ethyl)-amide (Compound 7I)

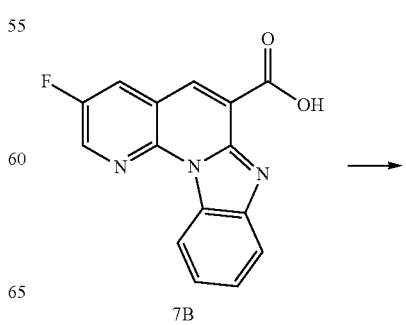

7B

-continued

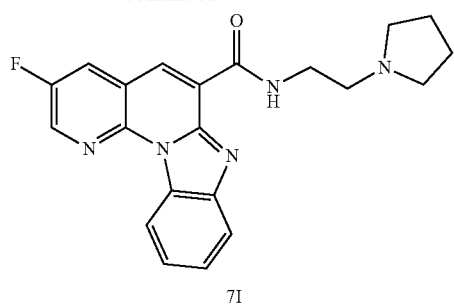

7I

Compound 7I was synthesized as yellow solid (21 mg) according to the procedure of compound 7F. LCMS: m/z 378 (M+H)+.

Example 45: Synthesis of 4-(4-Methyl-[1,4]diazepan-1-yl)-1,7,11b-triaza-benzo[c]fluorene-6-carboxylic acid ethyl ester (Compound 8A)

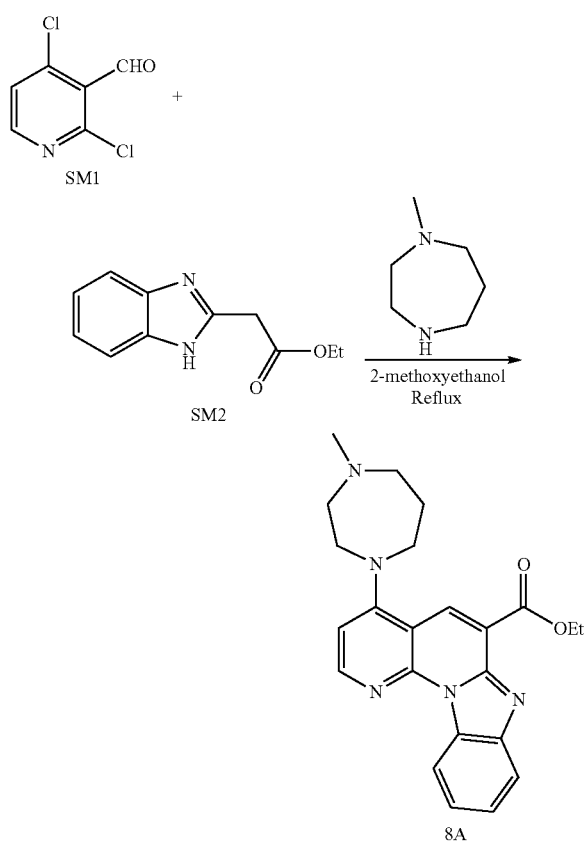

8A

To a solution of SM1 (176 mg, 1 mmol) and SM2 (204 mg, 1 mmol) in 2-Methoxyethanol (10 mL) was added N-Methylhomopiperazine (342 mg, 3 mmol) and the mixture was stirred at room temperature for 20 min. The reaction mixture was heated to reflux for 16 h. The crude product was purification by gel silica column (DCM/MeOH=50:1) to get compound 8A as brown oil (320 mg, 79% yield). LCMS: m/z 404 (M+H)+.

Example 46: Synthesis of 4-(4-Methyl-[1,4]diazepan-1-yl)-1,7,11b-triaza-benzo[c]fluorene-6-carboxylic acid methylamide (Compound 8M

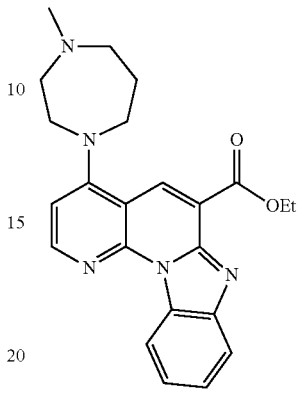

8A

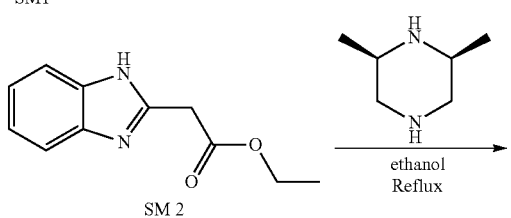

8B

A suspension of compound 8A (80 mg, 0.198 mmol) in CH₃NH₂/EtOH (2M, 4 ml, 800 mmol) was heated to reflux for 16 h. After cooling, the mixture was filtered and washed with ethanol, dried to give compound 8B as a pale yellow solid (40 mg, 52% yield). LCMS: m/z 389 (M+H)+.

Example 47: Synthesis of Compound 8C

-continued

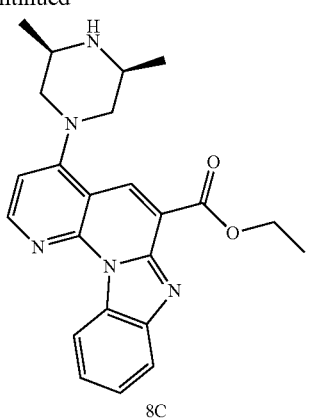

8C

Compound 8C was synthesized as yellow solid (360 mg) according to the procedure of compound 8A. LCMS: m/z 404 (M+H)+.

Example 48: Synthesis of Compound 8D

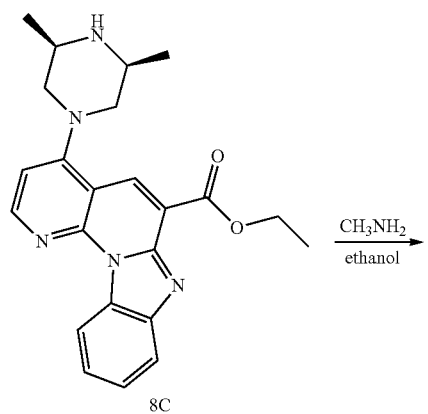

8C

CH₃NH₂ / ethanol

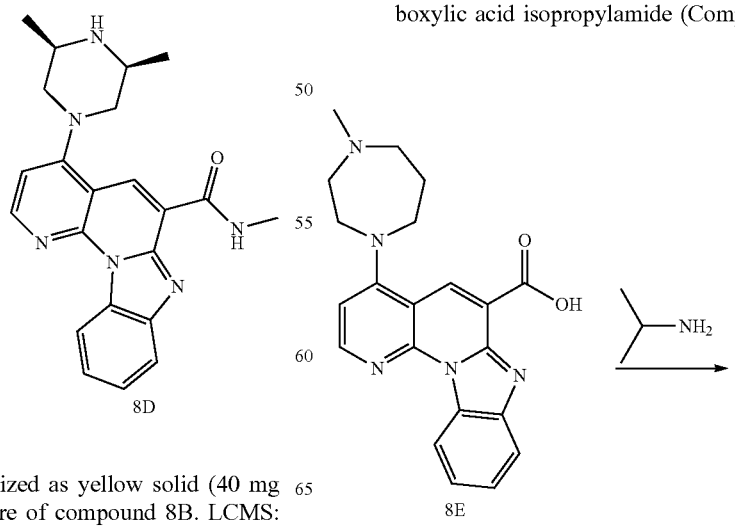

8D

Compound 8C was synthesized as yellow solid (40 mg) according to the procedure of compound 8B. LCMS: m/z 389 (M+H)+.

Example 49: Synthesis of 4-(4-Methyl-[1,4]diazepan-1-yl)-1,7,11b-triaza-benzo[c]fluorene-6-carboxylic acid (Compound 8F)

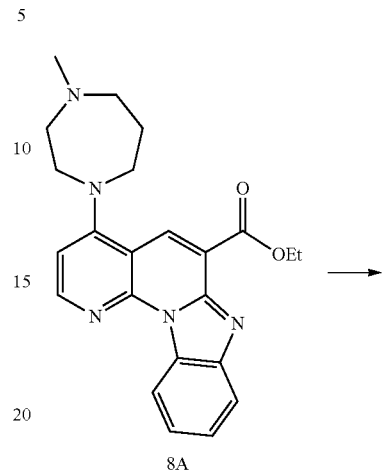

8A

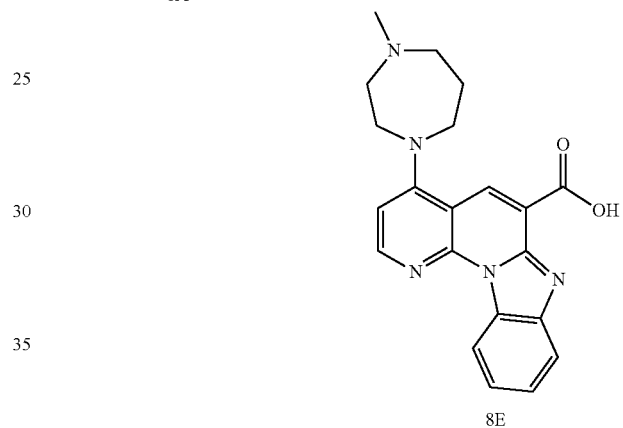

8E

Compound 8E was synthesized as pale yellow solid (140 mg) according to the procedure of compound 1A. LCMS: m/z 376 (M+H)+.

Example 50: Synthesis of 4-(4-Methyl-[1,4]diazepan-1-yl)-1,7,11b-triaza-benzo[c]fluorene-6-carboxylic acid isopropylamide (Compound 8F)

8E

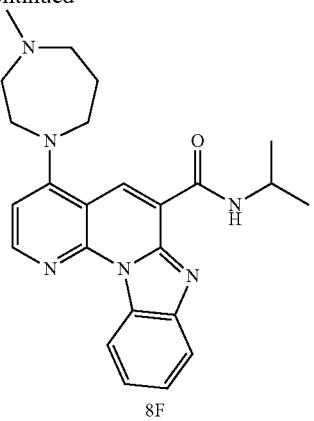

8F

Compound 8F was synthesized as yellow solid (10 mg) according to the procedure of compound 4A. LCMS: m/z 417 (M+H)+.

Example 51: Synthesis of 4-(4-Methyl-[1,4]diaz-epan-1-yl)-1,7,11b-triaza-benzo[c]fluorene-6-car-boxylic acid methoxy-amide (Compound 8G)

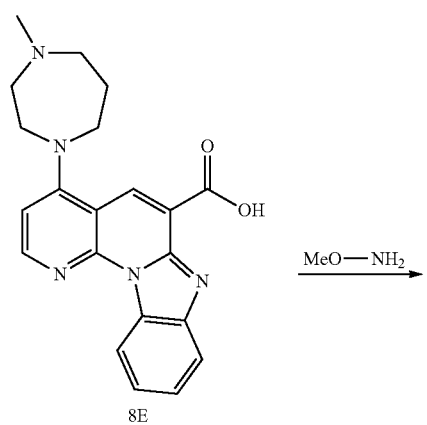

8E

MeO—NH$_2$ →

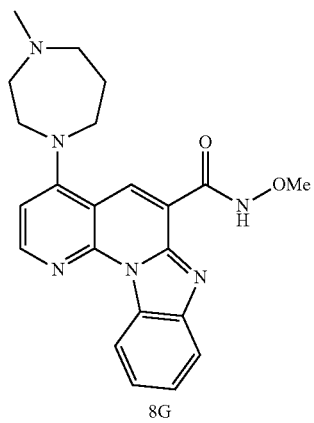

8G

Compound 8G was synthesized as yellow solid (16 mg) according to the procedure of compound 4A. LCMS: m/z 405 (M+H)+.

Example 52: Synthesis of Compound 8H

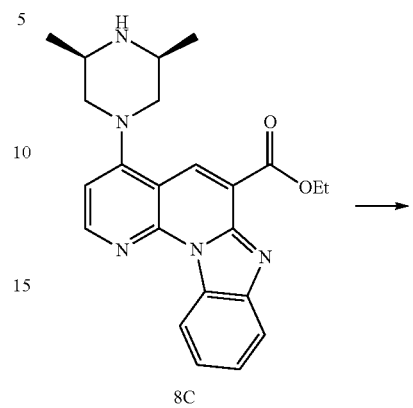

8C

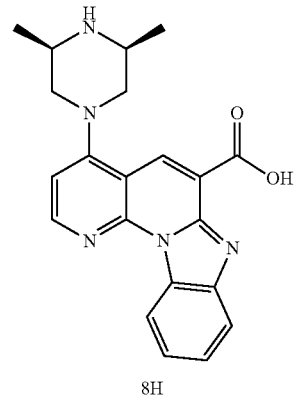

8H

Compound 8H was synthesized as pale yellow solid (180 mg) according to the procedure of compound 1A. LCMS: m/z 376 (M+H)+.

Example 53: Synthesis of Compound 8I

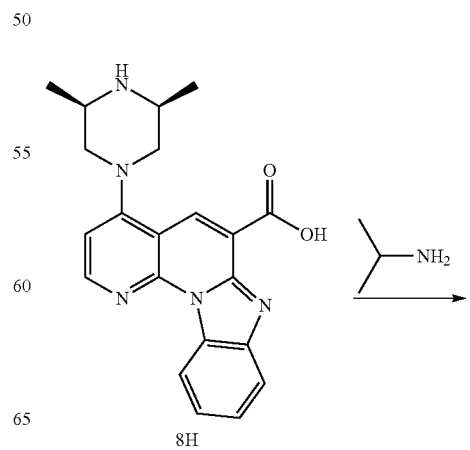

8H

-continued

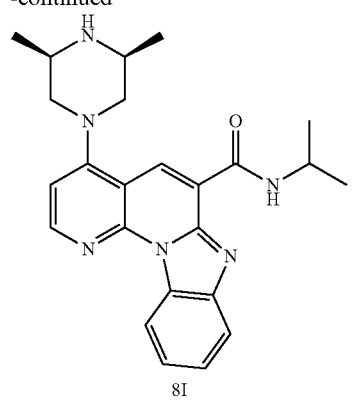

8I

Compound 8I was synthesized as yellow solid (10 mg) according to the procedure of compound 4A. LCMS: m/z 417 (M+H)+.

Example 54: Synthesis of Compound 8J

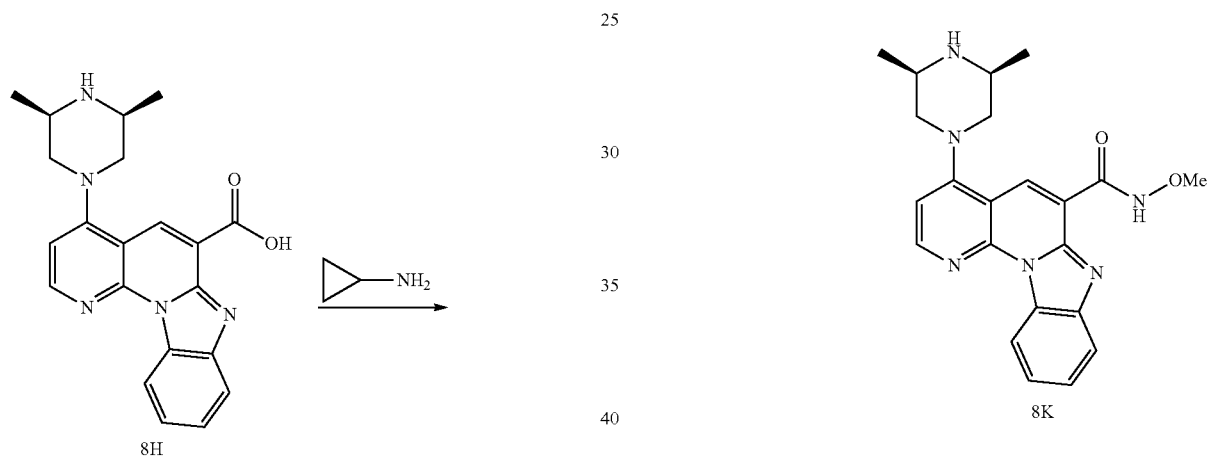

8H

8J

Compound 8J was synthesized as yellow solid (8 mg) according to the procedure of compound 4A. LCMS: m/z 415 (M+H)+.

Example 55: Synthesis of Compound 8K

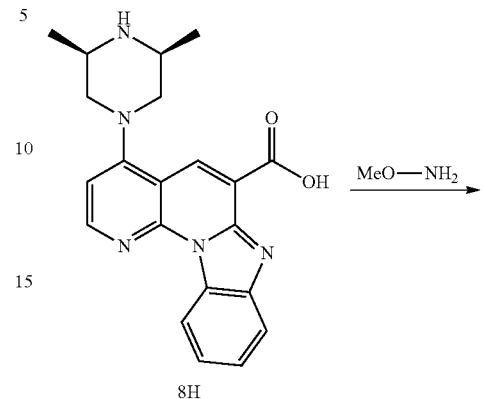

8H

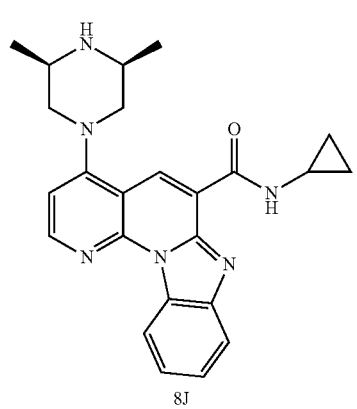

8K

Compound 8K was synthesized as yellow solid (11 mg) according to the procedure of compound 4A. LCMS: m/z 405 (M+H)+.

Example 56: Synthesis of 2-(4-tert-Butoxycarbonyl-[1,4]diazepan-1-yl)-1,7,11b-triaza-benzo[c]fluorene-6-carboxylic acid ethyl ester (Compound 9A)

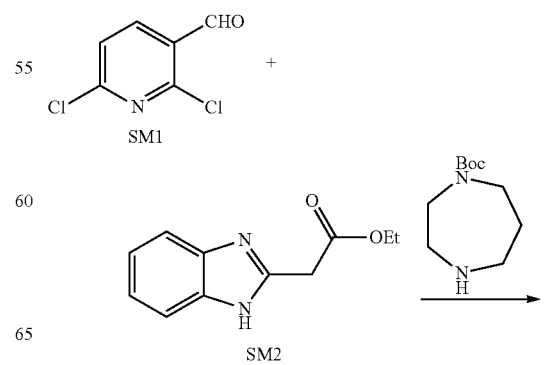

SM1

SM2

-continued

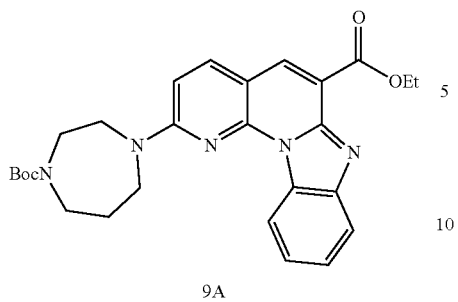

9A

To a solution of SM1 (176 mg, 1 mmol) and SM2 (204 mg, 1 mmol) in 2-Methoxyethanol (10 mL) was added N-Bochomopiperazine (600 mg, 3 mmol) and the mixture was stirred at room temperature for 20 min. The reaction mixture was heated to reflux for 16 h. The crude product was purification by gel silica column (DCM/MeOH=50:1) to get compound 9A as brown oil (490 mg, 50% yield). LCMS: m/z 490 (M+H)+.

Example 57: Synthesis of 2-[1,4]Diazepan-1-yl-1,7,11b-triaza-benzo[c]fluorene-6-carboxylic acid isopropylamide (Compound 9B)

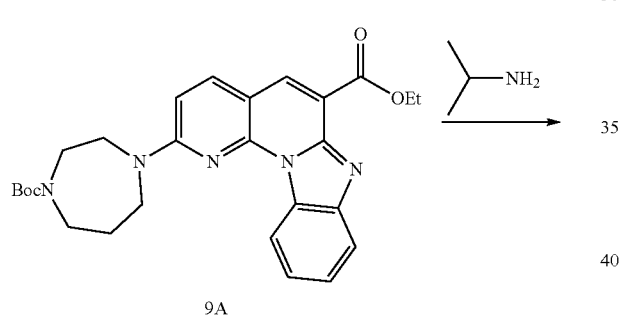

9A

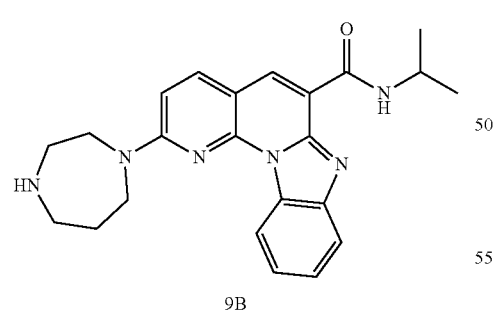

9B

A solution of compound 9A (100 mg, 0.20 mmol) and propan-2-amine (295 mg, 5.0 mmol) in EtOH (10 ml) was heated to reflux for 6 h. The mixture was then cooled to 20° C. and concentrated. To the residue was added 2N HCl (1 ml, 2.0 mmol) in MeOH (5 mL) and the mixture is stirred at r.t, overnight. The mixture was concentrated and purified by Pre-HPLC to give compound 9B (12 mg, yield=12%) as a pale yellow solid. LCMS: m/z 403 (M+H)+.

Example 58: Synthesis of 2-[1,4]Diazepan-1-yl-1,7,11b-triaza-benzo[c]fluorene-6-carboxylic acid methylamide (Compound 9C)

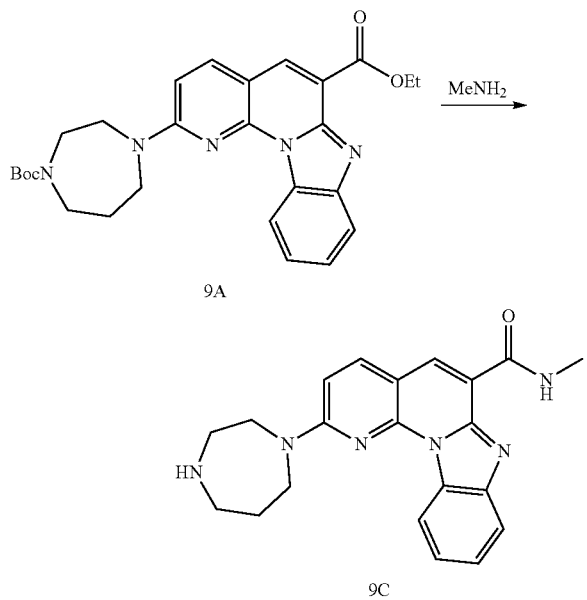

9A

9C

Compound 9C was synthesized as yellow solid (20 mg) according to the procedure of compound 4A. LCMS: m/z 375 (M+H)+.

Example 59: Synthesis of N-Hydroxy-2-(4-methyl-[1,4]diazepan-1-yl)-1,7,11b-triaza-benzo[c]fluorene-6-carboxamidine (Compound 10A)

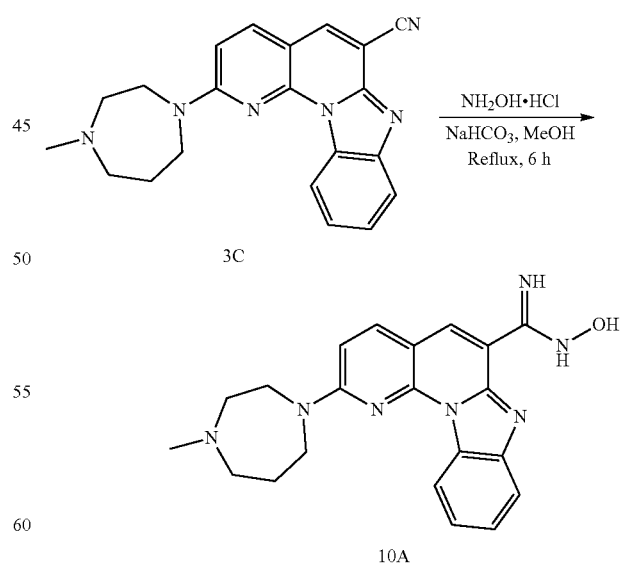

3C

10A

To a solution of compound 3C (356 mg, 1 mmol) and NH₂OH.HCl (83 mg, 1.2 mmol) in methanol (10 mL) was added 1N NaHCO₃ (1.2 mL, 1.2 mmol) and the mixture was stirred at refluxing for 6 h. After cooling, the mixture was filtered and washed with methanol to give compound 10A (210 mg, 53% yield) as yellow solid. LCMS: m/z 390 (M+H)+.

Example 60: Synthesis of 3-[2-(4-Methyl-[1,4]diazepan-1-yl)-1,7,11b-triaza-benzo[c]fluoren-6-yl]-4H-[1,2,4]oxadiazol-5-one (Compound 10B)

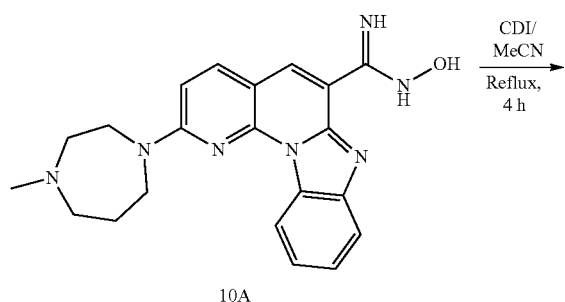

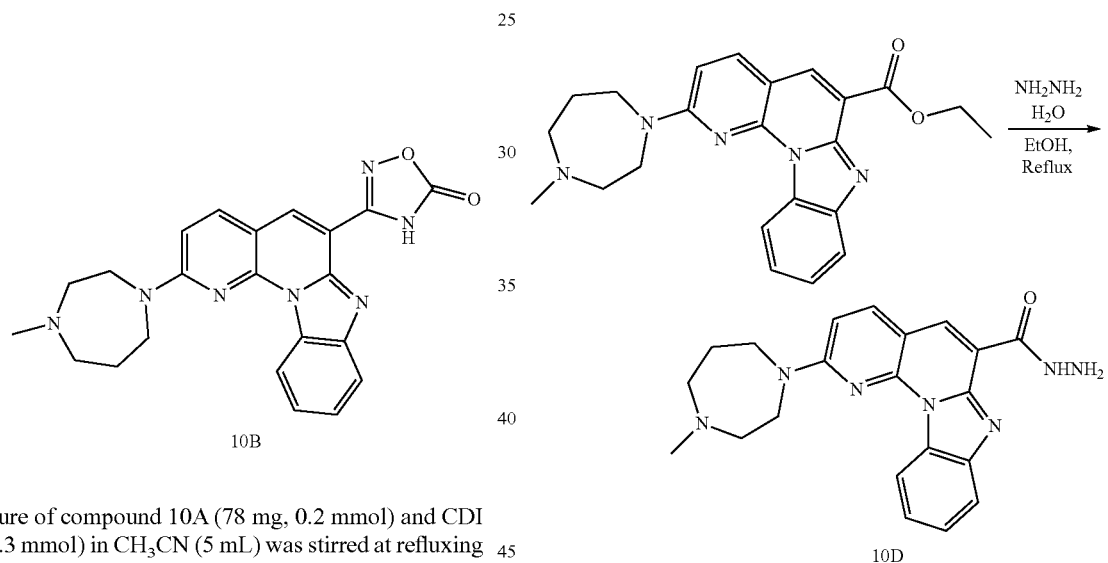

A mixture of compound 10A (78 mg, 0.2 mmol) and CDI (83 mg, 0.3 mmol) in CH₃CN (5 mL) was stirred at refluxing for 6 h. The mixture was concentrated and purified by pre-HPLC to give compound 10B (16 mg, 19% yield) as yellow solid. LCMS: m/z 416 (M+H)+.

Example 61: Synthesis of 2-(4-Methyl-[1,4]diazepan-1-yl)-6-(1H-tetrazol-5-yl)-1,7,11b-triaza-benzo[c]fluorine (Compound 10C)

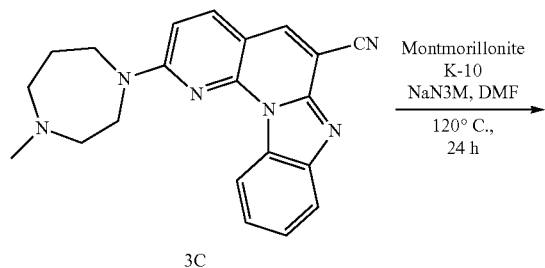

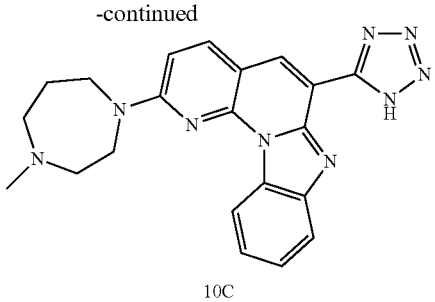

A mixture of compound 3C (105 mg, 0.29 mmol) and NaN3 (57 mg, 0.88 mmol) in DMF (5 mL) with Montmorillonite K-10 (50 mg) was stirred at 120° C. for 24 h. After cooling, the mixture was filtered and purified by pre-HPLC to give 10C (12 mg, 19% yield) as yellow solid. LCMS: m/z 400 (M+H)+.

Example 62: Synthesis of 2-(4-Methyl-[1,4]diazepan-1-yl)-1,7,11b-triaza-benzo[c]fluorene-6-carboxylic acid hydrazide (Compound 10D)

Compound 10D was synthesized as yellow solid (460 mg) according to the procedure of compound 4D. LCMS: m/z 389.9 (M+H)+.

Example 63: Synthesis of 2-(4-Methyl-[1,4]diazepan-1-yl)-6-(5-methyl-[1,3,4]oxadiazol-2-yl)-1,7,11b-triaza-benzo[c]fluorine (Compound 10E)

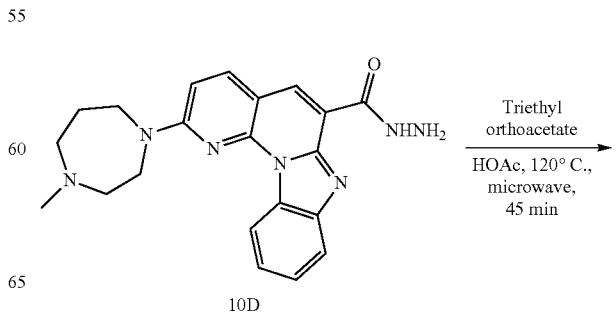

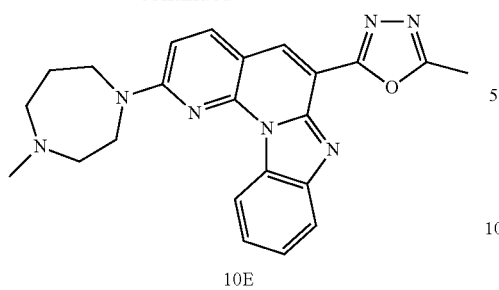

10E

A mixture of compound 10D (45 mg, 0.11 mmol) and Triethyl orthoacetate (53 mg, 0.33 mmol) in HOAc (3 mL) was stirred at 120° C. by microwave for 45 min. After cooling, the mixture was concentrated and purified by pre-HPLC to give compound 10E (20 mg, 41% yield) as yellow solid. LCMS: m/z 414.6 (M+H)+.

Example 64: Synthesis of 2-(2-Morpholin-4-yl-ethylamino)-1,7,11b-triaza-benzoklfluorene-6-carboxylic acid ethyl ester (Compound 11A)

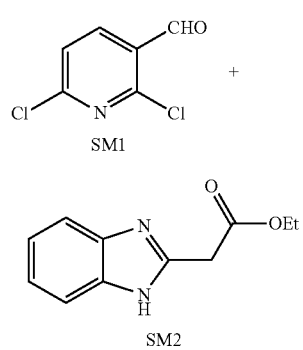

SM1

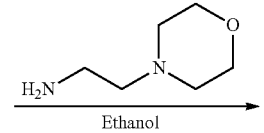

SM2

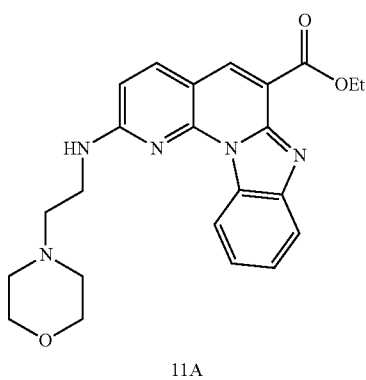

11A

To a solution of compound SM1 (147 mg) and compound SM2 (204 mg) in ethanol (10 mL) was added 2-Morpholin-4-yl-ethylamine (1 mmol) and the mixture was stirred at room temperature for 20 min. The reaction mixture was heated to reflux for 16 h. After cooling, the mixture was filtered and washed with ethanol, dried to get compound 11A as yellow solid (340 mg).

Example 65: Synthesis of 2-(2-Morpholin-4-yl-ethylamino)-1,7,11b-triaza-benzo[c]fluorene-6-carboxylic acid (Compound 11B)

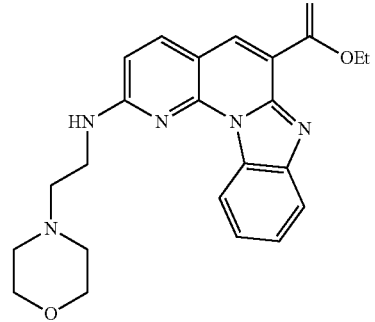

11A

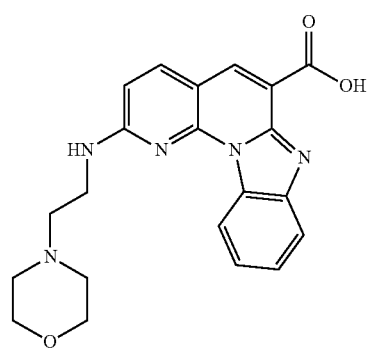

11B

Compound 11B was synthesized according to the procedure of compound 1A.

Example 66: Synthesis of 2-(2-Morpholin-4-yl-ethylamino)-1,7,11b-triaza-benzo[c]fluorene-6-carboxylic acid hydrazide (Compound 11C)

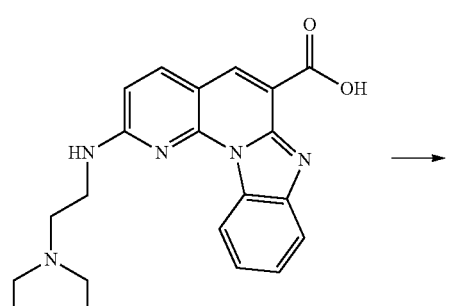

11B

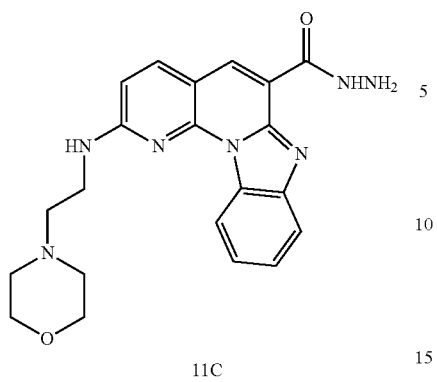

11C

Compound 11C was synthesized as yellow solid (40 mg) according to the procedure of compound 4A. LCMS: m/z 406 (M+H)+.

Example 67: Synthesis of 2-(2-Morpholin-4-yl-ethylamino)-1,7,11b-triaza-benzo[c]fluorene-6-carboxylic acid methylamide (Comnound 11D)

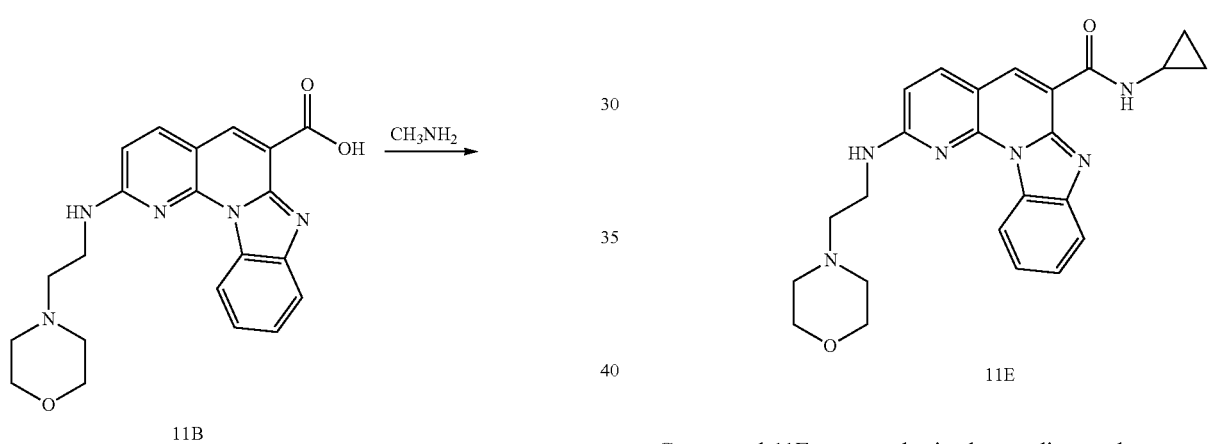

Compound 11D was synthesized as yellow solid (40 mg) according to the procedure of compound 4A. LCMS: m/z 405 (M+H)+.

Example 68: Synthesis of 2-(2-Morpholin-4-yl-ethylamino)-1,7,11b-triaza-benzo[c]fluorene-6-carboxylic acid cyclopropylamide (Compound 11E)

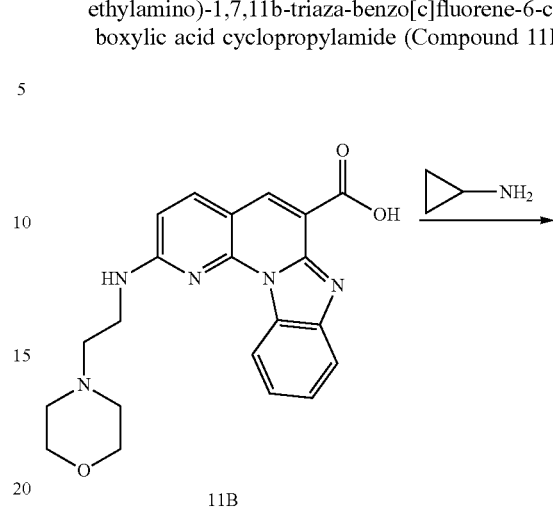

Compound 11E was synthesized according to the procedure of compound 4A.

Example 69: Synthesis of 2-(2-Morpholin-4-yl-ethylamino)-1,7,11b-triaza-benzo[c]fluorene-6-carboxylic acid methoxy-amide (Compound 11F)

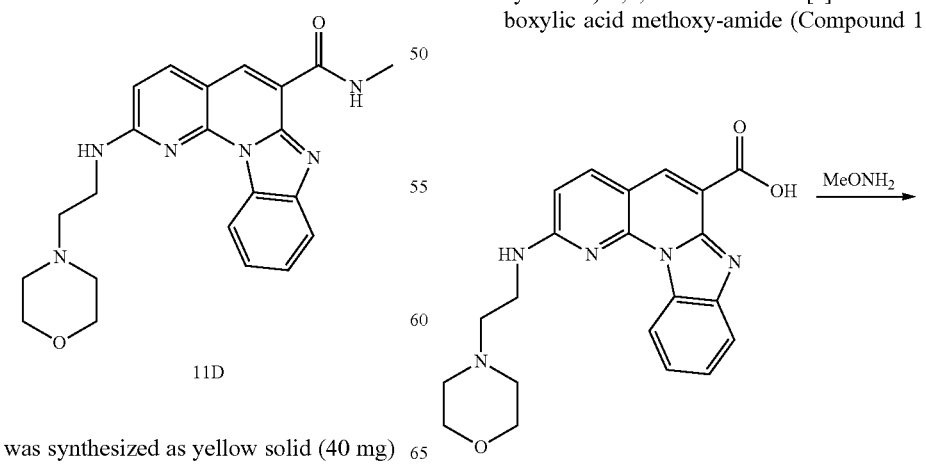

-continued

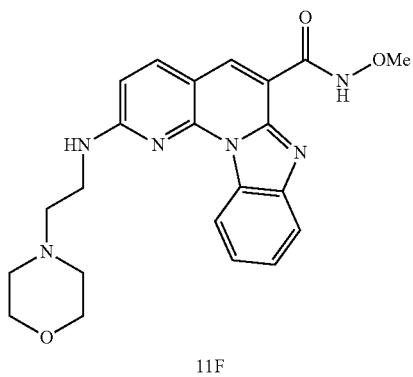

11F

Compound 11F was synthesized according to the procedure of compound 4A.

Example 70: Synthesis of 2-(2-Dimethylamino-ethylamino)-1,7,11b-triaza-benzo[c]fluorene-6-carboxylic acid ethyl ester (Compound 12A)

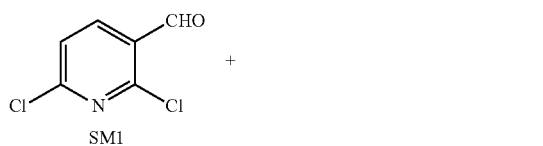

SM1

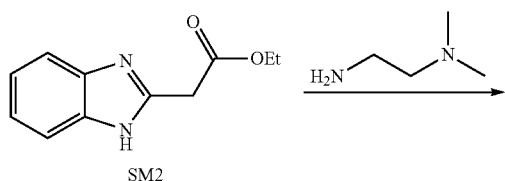

SM2

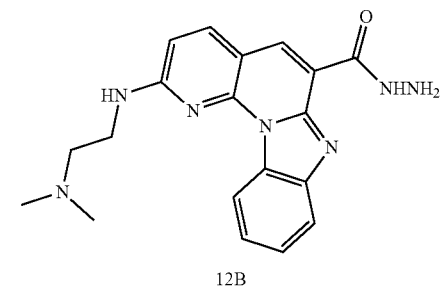

12A

To a solution of SM1 (1.76 g, 10 mmol) and SM2 (2.04 g, 10 mmol) in 2-Methoxyethanol (100 mL) was added N1,N1-dimethylethane-1,2-diamine (2.64 g, 30 mmol) and the mixture was stirred at refluxing for 16h. The crude product was purified by gel silica column (DCM/MeOH=50:1) to get 1.4 g crude product. The crude product was purified by pre-HPLC to get compound 12A as yellow solid (760 mg, 20% yield). LCMS: m/z 378 (M+H)+.

Example 71: Synthesis of 2-(2-Dimethylamino-ethylamino)-1,7,11b-triaza-benzo[c]fluorene-6-carboxylic acid hydrazide (Compound 12B)

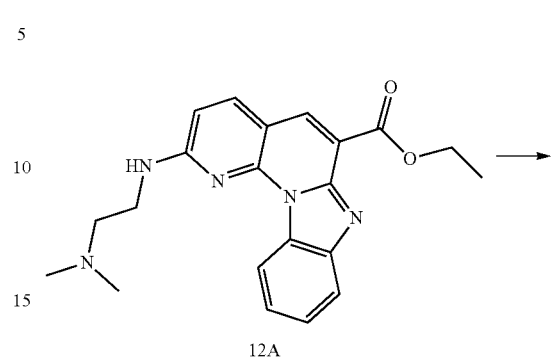

Compound 12B was synthesized as yellow solid (11 mg) according to the procedure of compound 4D. LCMS: m/z 364.5 (M+H)+.

Example 72: Synthesis of 2-(2-Dimethylamino-ethylamino)-1,7,11b-triaza-benzo[c]fluorene-6-carboxylic acid methylamide (Compound 12C)

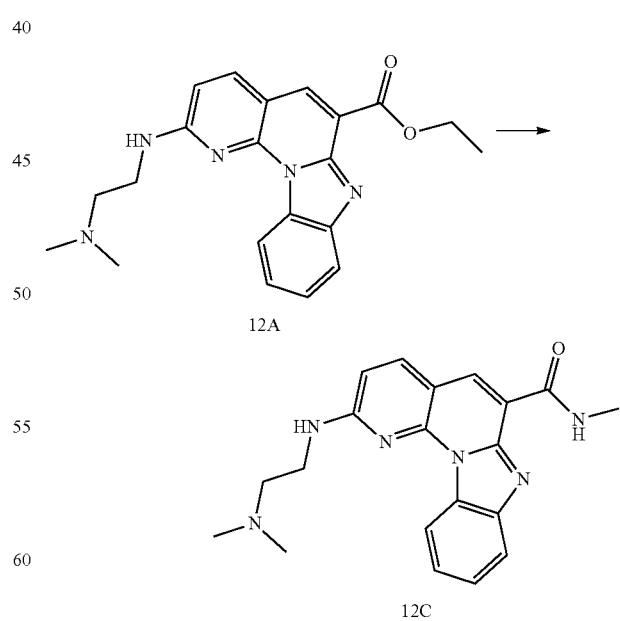

Compound 12C was synthesized as yellow solid (20 mg) according to the procedure of compound 4D. LCMS: m/z 363 (M+H)+.

Example 73: Synthesis of 3,7,11b-Triaza-benzo[c]fluorene-6-carboxylic acid ethyl ester (Compound 13A)

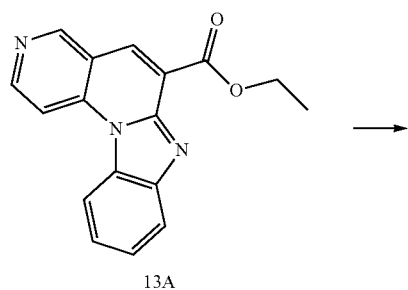

SM 3   SM 2

→ ethanol Reflux

13A

To a solution of compound SM3 (0.7 g) and compound SM2 (1.02 g) in ethanol (50 mL) was added piperidine (15 mmol) and the mixture was stirred at room temperature for 20 min. The reaction mixture was heated to reflux for 16 h. After cooling, the mixture was filtered and washed with ethanol, dried to get compound 13A as yellow solid (1.2 g).

Example 74: Synthesis of 3,7,11b-Triaza-benzo[c]fluorene-6-carboxylic acid (Compound 13B)

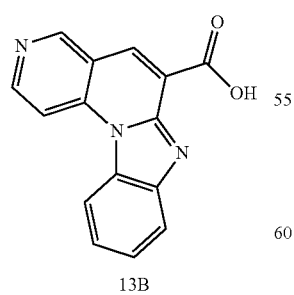

13A

13B

Compound 13B was synthesized as yellow solid (420 mg) according to the procedure of compound 1A. LCMS: m/z 264.4 (M+H)+.

Example 75: Synthesis of 3,7,11b-Triaza-benzo[c]fluorene-6-carboxylic acid isopropylamide (Compound 13C)

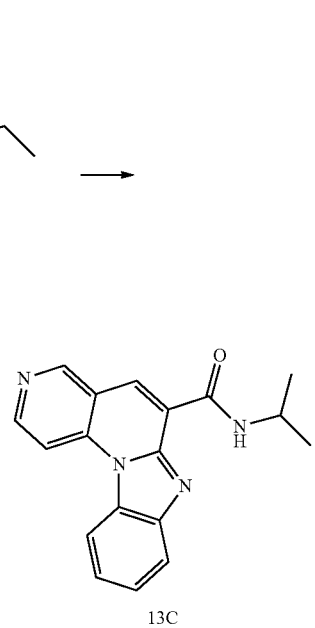

13A

13C

Compound 13C was synthesized as pale yellow solid (25 mg) according to the procedure of compound 4D. LCMS: m/z 305.5 (M+H)+.

Example 76: Synthesis of 3,7,11b-Triaza-benzo[c]fluorene-6-carboxylic acid (2-dimethylamino-ethyl)-amide (Compound 13D)

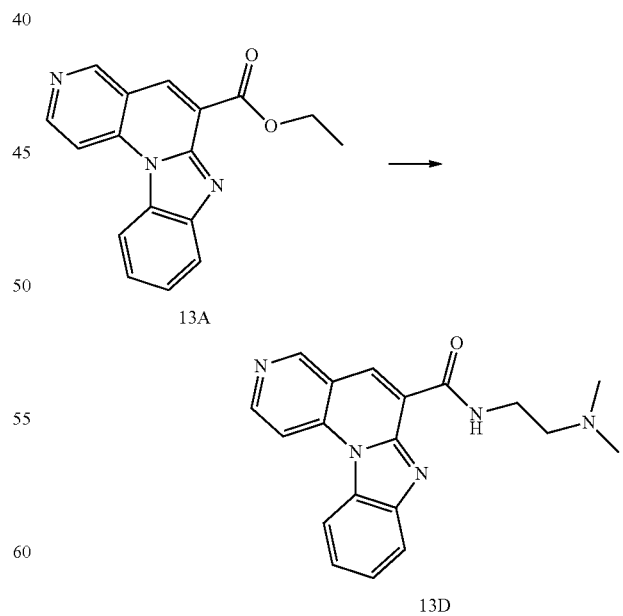

13A

13D

Compound 13D was synthesized as pale yellow solid (38 mg) according to the procedure of compound 4D. LCMS: m/z 334.5 (M+H)+.

Example 77: Synthesis of 3,7,11b-Triaza-benzo[c]
fluorene-6-carboxylic acid (3-methoxy-propyl)-
amide (Compound 13E)

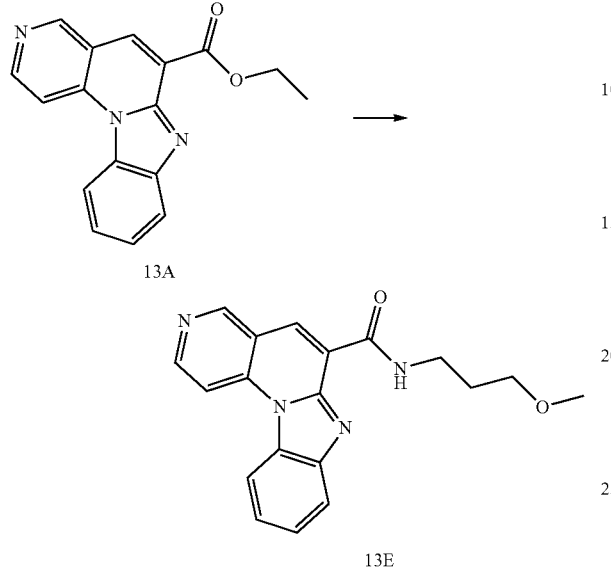

Compound 13E was synthesized as pale yellow solid (22 mg) according to the procedure of compound 4D. LCMS: m/z 336.5 (M+H)+.

Example 78: Synthesis of 3,7,11b-Triaza-benzo[c]
fluorene-6-carboxylic acid (2-morpholin-4-yl-ethyl)-
amide (Compound 13F)

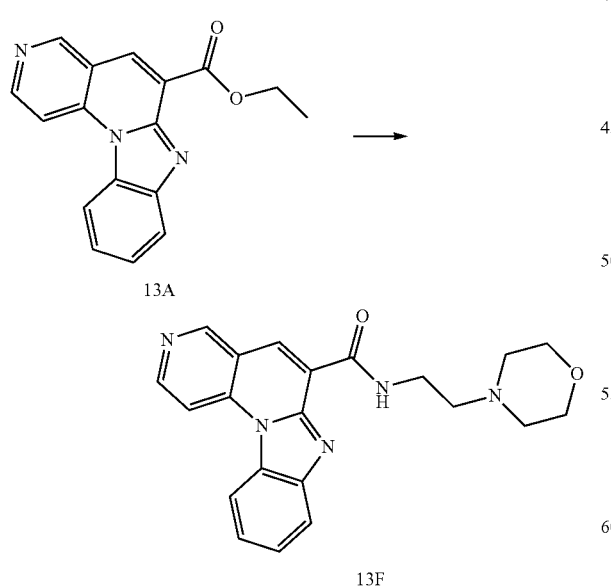

Compound 13F was synthesized as pale yellow solid (41 mg) according to the procedure of compound 4D. LCMS: m/z 376.5 (M+H)+.

Example 79: Synthesis of 3,7,11b-Triaza-benzo[c]
fluorene-6-carboxylic acid (2-pyrrolidin-1-yl-ethyl)-
amide (Compound 13G)

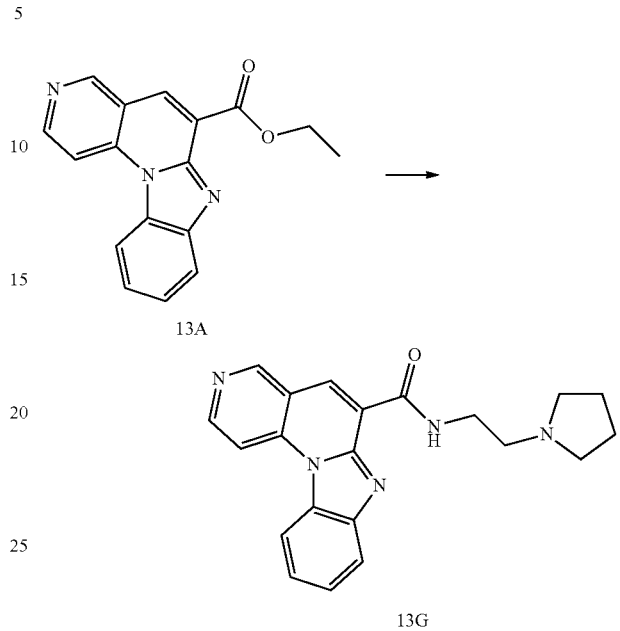

Compound 13G was synthesized as pale yellow solid (31 mg) according to the procedure of compound 4D. LCMS: m/z 360.4 (M+H)+.

Example 80: Synthesis of [1,4]Diazepan-1-yl-(3,7,
11b-triaza-benzo[c]fluoren-6-yl)-methanone (Compound 13H)

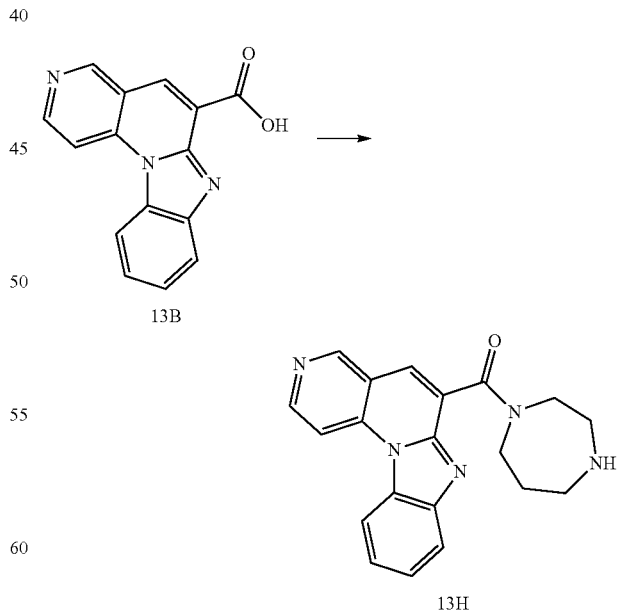

Compound 13H was synthesized as yellow solid (10 mg) according to the procedure of compound 7D. LCMS: m/z 346 (M+H)+.

Example 81: Synthesis of (4-Methyl-[1,4]diazepan-1-yl)-(3,7,11b-triaza-benzo[c]fluoren-6-yl)-methanone (Compound 13I)

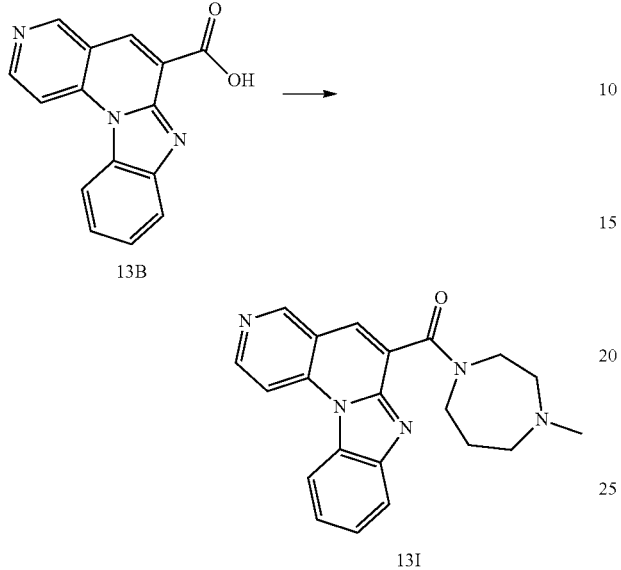

Compound 13I was synthesized as yellow solid (10 mg) according to the procedure of compound 4A. LCMS: m/z 360 (M+H)+.

Example 82: Synthesis of 3,7,11b-Triaza-benzo[c]fluorene-6-carboxylic acid (1-methyl-piperidin-4-yl)-amide (Compound 13J)

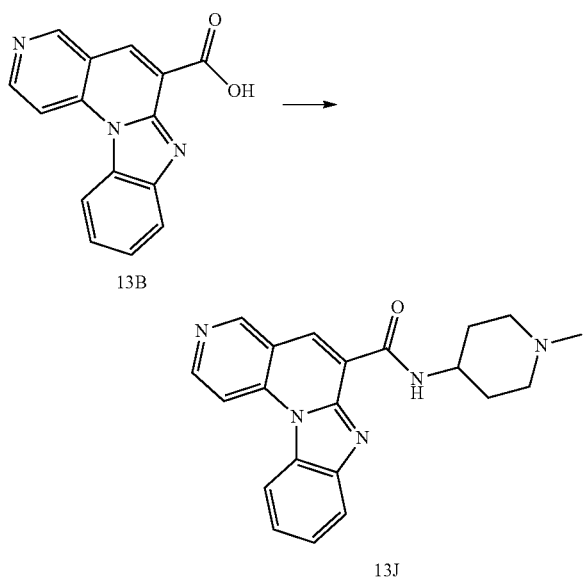

Compound 13J was synthesized as yellow solid (16 mg) according to the procedure of compound 4A. LCMS: m/z 360 (M+H)+.

Example 83: Synthesis of (3,5-Dimethyl-piperazin-1-yl)-(3,7,11b-triaza-benzo[c]fluoren-6-yl)-methanone (Compound 13K)

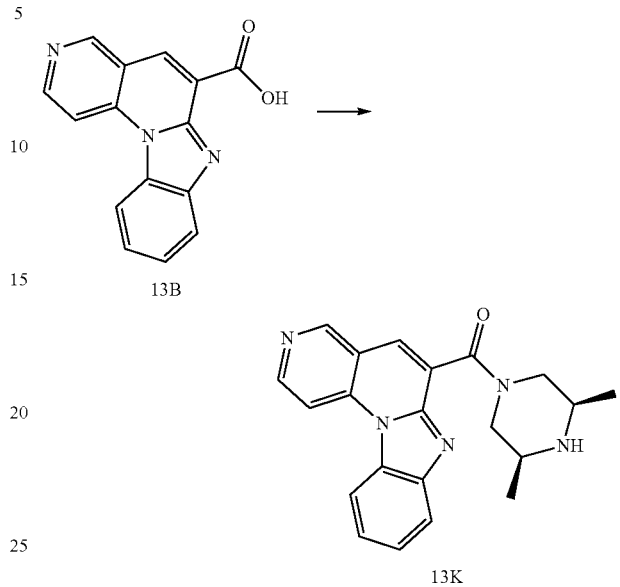

Compound 13K was synthesized as yellow solid (16 mg) according to the procedure of compound 4A. LCMS: m/z 360 (M+H)+.

Example 84: Representative Cell-Based IC$_{50}$ Data

Inhibitory activity on cell proliferation of representative compounds of the invention was determined using an Alamar Blue cell viability assay as described hereafter.

3000 cancer cells in 100 uL of cell culture media were plated in each well of a 96-well clear bottom, black wall cell culture-pretreated plate.

The next day compounds are serially diluted (3-fold in cell culture media) across a 96-well polypropylene mother plate from row A to row F, to yield 6 concentrations (10 uM, 3.3 uM, 1.1 uM, 370 nM, 124 nM and 41 nM) for each test compound. Rows G and H contain only DMSO.

Once titrations are made, the media in plates with cells were disposed and 100 μL of drug dilutions are transferred to plates with cells. After a ninety six-hour incubation at 37° C., 10 uL of resazurin solution from Alamar Blue Cell Viability kit (Invitrogen, Carlsbad, Calif.) was added to the media and cells were incubated at 37° C. for three more hours. At the end of this incubation the production of resofurin was measured using Spectrmax M2 microplate reader (Molecular Devices, Sunnyvale, Calif.)

Example 85: qRT-PCR Assay for Selective Inhibition of RNA Polymerase I Transcription 3000 cancer cells in 100 uL of cell culture media were plated in each well of a 96-well clear bottom, black wall cell culture-pretreated plate.

The next day compounds are serially diluted (3-fold in cell culture media) across a 96-well polypropylene mother plate from row A to row F, to yield 6 concentrations (10 uM, 3.3 uM, 1.1 uM, 370 nM, 124 nM and 41 nM) for each test compound. Rows G and H contain only DMSO.

Once titrations are made, the media in plates with cells were disposed and 100 μL of drug dilutions are transferred to plates with cells. After a ninety six-hour incubation at 37° C., 10 uL of resazurin solution from Alamar Blue Cell Viability kit (Invitrogen, Carlsbad, Calif.) was added to the media and cells were incubated at 37° C. for three more hours.

At the end of this incubation the production of resofurin was measured using Spectrmax M2 microplate reader (Molecular Devices, Sunnyvale, Calif.)

The Pol I transcription assay was used to measure the compound-dependent inhibition of the synthesis of rRNA versus mRNA. Briefly, this procedure utilizes a quantitative real time polymerase chain reaction assay (qRT-PCR) to quantify the amount of newly synthesized rRNA and mRNA in cancer cells treated with the drugs. The format of this assay is the same for all cell lines tested. Assay protocol is described hereafter.

$2*10^5$ cancer cells in 2 mL of cell culture media were plated in each well of a 6-well clear bottom, black wall cell culture-pretreated plate. The next day compounds are serially diluted (5-fold in cell culture media) in 15 mL conical tubes to yield 6 concentrations (25 uM, 5 uM, 1 uM, 200 nM, 40 nM and 8 nM) for each test compound.

Once titrations are made, the media in plates with cells were disposed and 2 mL of drug dilutions are transferred to plates with cells. After two-hour incubation at 37° C., the media with drug dilutions is disposed, the cells in the plate are washed once with 2 mL of ice-cold PBS and the total RNA from cells is isolated using RNAqueous®-Micro Total RNA Isolation Kit (Lechnologies, Carlsbad, Calif.) according to the manufacturer's protocol) and its concentration was determined using Ribogreen reagent (Life Lechnologies, Carlsbad, Calif.).

Relative levels of 45S pre-rRNA and c-myc mRNA were measured using Applied Biosystems' (Foster City, Calif.) proprietary primers-probe set for c-myc mRNA and custom primers probe set (forward primer: CCGCGCTCTACCT-TACCTACCT, reverse primer: GCATGGCTTAATCTTT-GAGACAAG, probe: TTGATCCTGCCAGTAGC) for pre-rRNA. Analysis was run on 7500HT Real Time PCR System (Applied Biosystems, Foster City, Calif.).

Example 86: Cell-Free Pol I Transcription Assay

To measure the direct effect of representative compounds on RNA Polymerase I transcription, a nuclear extract-based assay was used. Assay protocol is described hereafter.

Compounds are serially diluted (5-fold in cell culture media) across a 96-well polypropylene mother plate from row A to row E, to yield 5 concentrations (50 uM, 10 uM, 2 uM, 400 nM and 80 nM) for each test compound. Row G contained only DMSO.

Once titrations were made, the reaction mixture consisting of 30 ng/uL DNA template corresponding to (−160/+379) region on rDNA and 3 mg/mL nuclear extract isolated from HeLa S3 cells in a buffer containing 10 mM Tris HCl pH 8.0, 80 mM KCl, 0.8% polyvinyl alcohol, 10 mg/mL a-amanitin was combined with the test compounds and incubated at ambient for 20 min.

Transcription was initiated by addition of rNTP mix (New England Biolabs, Ipswich, MA) to a final concentration of 1 mM and was incubated for one hour at 30° C. Afterwards DNase I was added and the reaction was further incubated for 2 hr at 37° C. DNase digestion was terminated by the addition of EDTA to final concentration of 10 mM, followed immediately by 10 min incubation at 75° C., and then samples were transferred to 4° C. The levels of resultant transcript were analyzed by qRT-PCR on 7500HT Real Time PCR System (Applied Biosystems, Foster City, Calif.) using the following primer-probe set: Pol I probe ctctggcc-taccggtgacccggcta, Pol I forward primer gctgacacgctgtcctctggcg and Pol I reverse primer ggct-caagcaggagcgcggc.

Example 87: Testing Inhibition of RNA Polymerase I and II—Driven Transcriptions

A375 and U87-MG cells were plated in a 6-well format at $2*10^5$ cells/well overnight. The next day the cells were treated by a dilution series (6 doses total: 25 uM, 5 uM, 1 uM, 200 nM, 40 nM, 8 nM) of test compounds. Two hours after the beginning of treatment cells were washed and lysed for RNA isolation that was performed using RNAqueous-Mini Total RNA Isolation kit (Ambion).

The resulting RNA concentrations were determined using Quant-iT RiboGreen RNA Assay Kit (Molecular Probes). Effect on RNA Polymerase I and RNA Polymerase II—driven transcription was assessed by monitoring resulting levels of 45S pre-rRNA and cMYC mRNA respectively. For this we performed Taqman qRT-PCR assay using TaqMan® RNA-to-Ct™ 1-Step Kit (Life Technologies) with custom primer-probe set for 45S pre-rRNA (Drygin et all 2009 Cancer Res 69:7653) and Hs00153408 ml primer-probe mix (Life Technologies) for cMYC mRNA. The assay was performed on Applied Biosystems 7500 Fast Real-Time PCR System (ABI) using Absolute Quantitation method. The data was analyzed using GraphPad Prism (GraphPad) software.

Example 88: Pharmaceutical Activity of Representative Compounds

Representative cell proliferation inhibition from Alamar Blue assay (e.g. Example 84 herein) and Pol I and II transcription inhibition, in U-87 MG cell line, from quantitative PCR (QPCR) (Example 86 & Example 87) data is provided in Table 1.

TABLE 1

| | Pharmaceutical activity IC50 | | | | | | | | | |
|---|---|---|---|---|---|---|---|---|---|---|
| Compound | A375 | A2058 | Malme-3M | SK-MEL 28 | 2008 | A2780 | ES.2 | U-87 MG | Pol I | Pol II |
| 1A | +++ | | | | | | | | | |
| 2A | + | | | | | | | | | |
| 2B | + | | | | | | | | | |
| 2C | ++ | | | | | | | | | |
| 2D | ++ | | | | | | | | | |
| 2E | +++ | + | | | | | | | ++ | − |
| 2F | ++ | | | | | | | | | |
| 2G | +++ | +++ | +++ | +++ | +++ | +++ | +++ | +++ | +++ | + |
| 3A | +++ | | | | | | | | | |
| 3B | +++ | | | | | | | | | |

+++ indicates an activity of less than 1 μM;
++ indicates an activity of greater than 1 μM and less than 5 μM;
+ indicates an activity of greater than 5 μm and less than 10 μM; and
− indicates an activity of greater than 10 μM.

Example 89: Pharmaceutical Activity of Representative Compounds

Representative cell proliferation inhibition from Alamar Blue assay (e.g. Example 84 herein) is provided in Table 2.

TABLE 2

| Compound | ES.2 | Hs.294T | WM-115 | Hep G2 | SKM-1 |
|---|---|---|---|---|---|
| 2G | +++ | +++ | ++ | +++ | +++ |
| 1A | +++ | +++ | +++ | +++ | +++ |
| 3A | | | | +++ | +++ |
| 3B | | | | +++ | +++ |

+++ indicates an activity of less than 1 μM; and ++ indicates an activity of greater than 1 μM and less than 5 μM.

Example 90: Pharmaceutical Activity of Representative Compounds

Representative cell proliferation inhibition from Alamar Blue assay (e.g. Example 84 herein) is provided in Table 3.

TABLE 3

| | Compound | | | | Compound | | |
|---|---|---|---|---|---|---|---|
| Cell line | 2G | 1A | 3A | Cell line | 2G | 1A | 3A |
| KG-1 | +++ | +++ | +++ | DLD-1 | +++ | ++ | +++ |
| ML-2 | +++ | +++ | +++ | CT26 | ++ | + | + |
| NB4-Av | +++ | +++ | +++ | LnCAP | ++ | + | + |
| NOMO-1 | +++ | +++ | +++ | 4T1 | + | + | + |
| SKM_1_AV | +++ | +++ | +++ | NCI-H1299 | ++ | ++ | + |
| B16-F10 | ++ | + | ++ | HCT-116 | +++ | +++ | +++ |
| AGS | +++ | ++ | +++ | A549 | ++ | + | + |
| MCF7 | ++ | ++ | + | PC-3 | +++ | ++ | ++ |
| MDA-MB-231 | +++ | ++ | +++ | HT-1080 | ++ | ++ | + |

+++ indicates an activity of less than 1 μM;
++ indicates an activity of greater than 1 μM and less than 5 μM;
+ indicates an activity of greater than 5 mm and less than 10 μM.

Example 91: Pharmaceutical Activity of Representative Compounds

Representative cell proliferation inhibition from Alamar Blue assay (e.g. Example 84 herein) is provided in Table 4.

TABLE 4

| Pharmaceutical activity in A375 cell line | | | | | | | | | | | |
|---|---|---|---|---|---|---|---|---|---|---|---|
| Compound | $IC_{50}$ | Compound | $IC_{50}$ | Compound | $IC_{50}$ | Compound | $IC_{50}$ | Compound | $IC_{50}$ | Compound | $IC_{50}$ |
| 4F | *** | 11D | ** | 13D | *** | 3F | *** | 12C | *** | 7C | – |
| 4C | *** | 4E | ** | 13F | * | 3G | ** | 5B | * | 7F | ** |
| 10E | *** | 7D | – | 13G | *** | 3H | *** | 5C | ** | 7G | – |
| 9B | ** | 8B | *** | 3C | *** | 3I | ** | 5E | ** | 7I | ** |
| 12B | ** | 8D | *** | 3D | *** | 4A | * | 5D | * | 13E | * |
| 11C | * | 13C | * | 3E | ** | 4D | *** | 6A | * | 7B | – |

*** indicates an $IC_{50}$ of less than 1 μM;
** indicate an $IC_{50}$ of greater than 1 μM and less than 5 μM;
* indictes an $IC_{50}$ greater than 5 μM and less than 10 μM;
– indicates an $IC_{50}$ of greater than 10 μM

Example 92: Pharmaceutical Activity of Representative Compounds

Representative cell proliferation inhibition from Alamar Blue assay (e.g. Example 84 herein) is provided in Table 5.

TABLE 5

| $IC_{50}$ of compound 2G in ovarian cell lines | | | | | |
|---|---|---|---|---|---|
| kuramochi | JHOC7 | JHOC9 | JHOM1 | EF-21 | TOV112D |
| *** | *** | *** | *** | *** | *** |

*** indicates an $IC_{50}$ of less than 1 μM

Example 93: Pharmaceutical Activity of Representative Compounds

Representative Pol I and II transcription inhibition, in A375 Malignant Melanoma cell line, from quantitative PCR (QPCR) (Example 85 and Example 87) data is provided in Table 6.

TABLE 6

| | Pol I and Pol II $IC_{50}$ | |
|---|---|---|
| Compound | Pol I | Pol II |
| 3A | **** | ND |
| 3D | **** | ** |
| 12C | *** | ** |
| 13D | **** | **** |
| 8B | ** | * |
| 10E | ** | **** |

**** indicates an $IC_{50}$ of less than 0.5 μM;
*** indicates an $IC_{50}$ between 0.5 μM and 1 μM;
** indicates an $IC_{50}$ of greater than 1 μM;
ND means not determined The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A method for treating cancer in a subject comprising administering to the subject a therapeutically effective amount of a benzo[4,5]imidazo[1,2-a][1,8]naphthyridine compound, or a pharmaceutically acceptable salt or solvate thereof, wherein the cancer is breast cancer, lung cancer, colorectal cancer, liver cancer, pancreatic cancer, lymph node cancer, colon cancer, prostate cancer, brain cancer, head and neck cancer, skin cancer, kidney cancer, blood cancer, or heart cancer.

2. The method of claim 1, wherein the benzo[4,5]imidazo[1,2-a][1,8]naphthyridine compound has the structure of Formula II(A), or a pharmaceutically acceptable salt or solvate thereof:

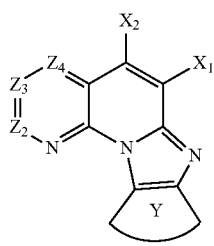

Formula II(A)

wherein,

Y is an optionally substituted 6-membered carbocyclic ring;

$X_1$ is an optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, optionally substituted with one or more halogens, =O, $CF_3$, CN, $OR_7$, $NR_8R_9$, $SR_7$, $SO_2NR_8R_9$, $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group; wherein each $R_7$, $R_8$ and $R_9$ is independently selected from H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, =O, =N—CN, =N—OR', =NR', OR', N(R')$_2$, SR', $SO_2R'$, $SO_2NR'_2$, NR'$SO_2R'$, NR'CONR'$_2$, NR'COOR', NR'COR', CN, COOR', CON(R')$_2$, OOCR', COR', and $NO_2$; wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S; or $X_1$ is H, $NR_2R_3$, $SOR_2$, $SO_2R_2$, $SO_2NR_2R_3$, $NR_2SO_2R_3$, $NR_2CONR_2R_3$, $NR_2COOR_3$, $NR_2COR_3$, CN, $COOR_2$, ester bioisostere, COOH, carboxy bioisostere, $CONR_2R_3$, amide bioisostere, $OOCR_2$, $COR_2$, or $NO_2$, wherein each $R_2$ and $R_3$ is independently selected from H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein $R_2$ and $R_3$ groups on the same atom or on adjacent atoms can be linked to form a 3-8 membered ring, optionally containing one or more N, O or S atoms; and each $R_2$ and $R_3$ groups, and each ring formed by linking $R_2$ and $R_3$ groups together, is optionally substituted with one or more substituents selected from halo, =O, =N—CN, =N—OR', =NR', OR', N(R')$_2$, SR', $SO_2R'$, $SO_2NR'_2$, NR'$SO_2R'$, NR'CONR'$_2$, NR'COOR', NR'COR', CN, COOR', CON(R')$_2$, OOCR', COR', and $NO_2$; wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S;

$X_2$ is, H, halogen, $CF_3$, CN, $C_1$-$C_{10}$ alkyl, $C_1$-$C_{10}$ heteroalkyl, $C_2$-$C_{10}$ alkenyl, or $C_2$-$C_{10}$ heteroalkenyl, each of which is optionally substituted with one or more halogens, =O, an optionally substituted 3-7 membered carbocyclic or heterocyclic ring, $OR_7$, $NR_8R_9$, $SR_7$, or $SO_2NR_8R_9$; wherein each $R_7$, $R_8$ and $R_9$ is independently selected from H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, =O, =N—CN, =N—OR', =NR', OR', N(R')$_2$, SR', $SO_2R'$, $SO_2NR'_2$, NR'$SO_2R'$, NR'CONR'$_2$, NR'COOR', NR'COR', CN, COOR', CON(R')$_2$, OOCR', COR', and $NO_2$; wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S, and wherein $R_7$ is not hydrogen when $X_2$ is $OR_7$;

each $Z_1$, $Z_2$, $Z_3$, and $Z_4$ is independently N, CH, or $CR_1$, provided that any three N atoms are non-adjacent; and further provided that one or more of $Z_1$, $Z_2$, $Z_3$, and $Z_4$ is $CR_1$;

wherein each $R_1$ is independently an optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group; or each $R_1$ is independently H, halo, $CF_3$, $OR_2$, $NR_2R_3$, $NR_2OR_3$, $NR_2NR_2R_3$, $SR_2$, $SOR_2$, $SO_2R_2$, $SO_2NR_2R_3$, $NR_2SO_2R_3$, $NR_2CONR_2R_3$, $NR_2COOR_3$, $NR_2COR_3$, CN, $COOR_2$, COOH, $CONR_2R_3$, $OOCR_2$, $COR_2$, or $NO_2$; wherein each $R_2$ and $R_3$ is independently selected from H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein $R_2$ and $R_3$ groups on the same atom or on adjacent atoms can be linked to form a 3-8 membered ring, optionally containing one or more N, O or S atoms; and each $R_2$ and $R_3$ groups, and each ring formed by linking $R_2$ and $R_3$ groups together, is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$; wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S; or each $R_1$ is independently —W, -L-W, —X-L-A;
 wherein X is $NR_6$, O, or S;
  wherein $R_6$ is H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group;
   wherein $R_6$ can be linked to $R_4$ or $R_5$ to form a 3-8 membered ring optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$; wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S;
  each W is independently an optionally substituted 4-7 membered azacyclic ring, optionally containing an additional heteroatom selected from N, O and S as a ring member;
 L is a bond, $C_1$-$C_{10}$ alkylene, $C_1$-$C_{10}$ heteroalkylene, $C_2$-$C_{10}$ alkenylene or $C_2$-$C_{10}$ heteroalkenylene linker, each of which is optionally substituted with one or more substituents selected from the group consisting of halogen, oxo (=O), or $C_1$-$C_6$ alkyl; and
 A is heterocycloalkyl, heteroaryl or $NR_4R_5$, wherein $R_4$ and $R_5$ are each independently H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group; wherein $R_4$ and $R_5$ are optionally linked to form a 3-8 membered ring, optionally containing one or more N, O or S; and each $R_4$ and $R_5$ groups, and each ring formed by linking $R_4$ and $R_5$ groups together, is optionally substituted with one or more substituents selected from halo, =O, =N—CN, =N—OR', =NR', OR', N(R')$_2$, SR', SO$_2$R', SO$_2$NR'$_2$, NR' SO$_2$R', NR'CONR'$_2$, NR'COOR', NR'COR', CN, COOR', CON(R')$_2$, OOCR', COR', and NO$_2$; wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

3. A method for treating cancer in a subject comprising administering to the subject a therapeutically effective amount of a benzo[4,5]imidazo[1,2-a][1,6]naphthyridine compound, or a pharmaceutically acceptable salt or solvate thereof, wherein the cancer is breast cancer, lung cancer, colorectal cancer, liver cancer, pancreatic cancer, lymph node cancer, colon cancer, prostate cancer, brain cancer, head and neck cancer, skin cancer, kidney cancer, blood cancer, or heart cancer.

4. The method of claim 3, wherein the benzo[4,5]imidazo[1,2-a][1,6]naphthyridine compound has the structure of Formula II(E), or a pharmaceutically acceptable salt or solvate thereof:
 wherein,

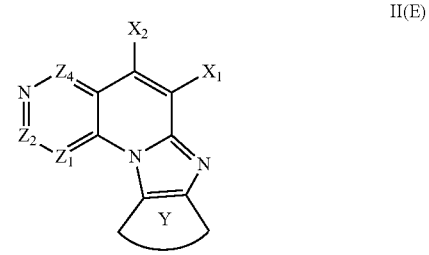

II(E)

Y is an optionally substituted 6 membered carbocyclic ring;
$X_1$ is an optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group, optionally substituted with one or more halogens, =O, $CF_3$, CN, $OR_7$, $NR_8R_9$, $SR_7$, $SO_2NR_8R_9$, $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group; wherein each $R_7$, $R_8$ and $R_9$ is independently selected from H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$; wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S; or $X_1$ is H, $NR_2R_3$, $SOR_2$, $SO_2R_2$, $SO_2NR_2R_3$, $NR_2SO_2R_3$, $NR_2CONR_2R_3$, $NR_2COOR_3$, $NR_2COR_3$, CN, $COOR_2$, ester bioisostere, COOH, carboxy bioisostere, $CONR_2R_3$, amide bioisostere, $OOCR_2$, $COR_2$, or $NO_2$, wherein each $R_2$ and $R_3$ is independently selected from H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein $R_2$ and $R_3$ groups on the same atom or on adjacent atoms can be linked to form a 3-8 membered ring, optionally containing one or more N, O or S atoms; and each $R_2$ and $R_3$ groups, and each ring formed by linking $R_2$ and $R_3$ groups together, is optionally substituted with one or more substituents selected from halo, =O, =N—CN, =N—OR', =NR', OR', N(R')$_2$, SR', $SO_2$R', $SO_2$NR'$_2$, NR'$SO_2$R', NR'CONR'$_2$, NR'COOR', NR'COR', CN, COOR', CON(R')$_2$, OOCR', COR', and $NO_2$; wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S;

$X_2$ is, H, halogen, $CF_3$, CN, $C_1$-$C_{10}$ alkyl, $C_1$-$C_{10}$ heteroalkyl, $C_2$-$C_{10}$ alkenyl, or $C_2$-$C_{10}$ heteroalkenyl, each of which is optionally substituted with one or more halogens, =O, an optionally substituted 3-7 membered carbocyclic or heterocyclic ring, $OR_7$, $NR_8R_9$, $SR_7$, or $SO_2NR_8R_9$; wherein each $R_7$, $R_8$ and $R_9$ is independently selected from H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, =O, =N—CN, =N—OR', =NR', OR', N(R')$_2$, SR', $SO_2$R', $SO_2$NR'$_2$, NR'$SO_2$R', NR'CONR'$_2$, NR'COOR', NR'COR', CN, COOR', CON(R')$_2$, OOCR', COR', and $NO_2$; wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S, and wherein $R_7$ is not hydrogen when $X_2$ is $OR_7$;

each $Z_1$, $Z_2$, $Z_3$, and $Z_4$ is independently N, CH, or $CR_1$, provided that any three N atoms are non-adjacent; and further provided that one or more of $Z_1$, $Z_2$, $Z_3$, and $Z_4$ is $CR_1$;

wherein each $R_1$ is independently an optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group; or each $R_1$ is independently H, halo, $CF_3$, $OR_2$, $NR_2R_3$, $NR_2OR_3$, $NR_2NR_2R_3$, $SR_2$, $SOR_2$, $SO_2R_2$, $SO_2NR_2R_3$, $NR_2SO_2R_3$, $NR_2CONR_2R_3$, $NR_2COOR_3$, $NR_2COR_3$, CN, $COOR_2$, COOH, $CONR_2R_3$, $OOCR_2$, $COR_2$, or $NO_2$; wherein each $R_2$ and $R_3$ is independently selected from H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein $R_2$ and $R_3$ groups on the same atom or on adjacent atoms can be linked to form a 3-8 membered ring, optionally containing one or more N, O or S atoms; and each $R_2$ and $R_3$ groups, and each ring formed by linking $R_2$ and $R_3$ groups together, is optionally substituted with one or more substituents selected from halo, =O, =N—CN, =N—OR', =NR', OR', N(R')$_2$, SR', $SO_2$R', $SO_2$NR'$_2$, NR'$SO_2$R', NR'CONR'$_2$, NR'COOR', NR'COR', CN, COOR', CON(R')$_2$, OOCR', COR', and $NO_2$; wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S; or each $R_1$ is independently —W, -L-W, —X-L-A;

wherein X is $NR_6$, O, or S;

wherein $R_6$ is H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group;

wherein $R_6$ can be linked to $R_4$ or $R_5$ to form a 3-8 membered ring optionally substituted with one or more substituents selected from halo, =O, =N—CN, =N—OR', =NR', OR', N(R')$_2$, SR', $SO_2$R', $SO_2$NR'$_2$, NR'$SO_2$R', NR'CONR'$_2$, NR'COOR', NR'COR', CN, COOR', CON(R')$_2$, OOCR', COR', and $NO_2$; wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S;

each W is independently an optionally substituted 4-7 membered azacyclic ring, optionally containing an additional heteroatom selected from N, O and S as a ring member;

L is a bond, $C_1$-$C_{10}$ alkylene, $C_1$-$C_{10}$ heteroalkylene, $C_2$-$C_{10}$ alkenylene or $C_2$-$C_{10}$ heteroalkenylene linker, each of which is optionally substituted with one or more substituents selected from the group consisting of halogen, oxo (=O), or $C_1$-$C_6$ alkyl; and A is heterocycloalkyl, heteroaryl or $NR_4R_5$, wherein $R_4$ and $R_5$ are each independently H, optionally substituted $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_1$-$C_8$ acyl, $C_2$-$C_8$ heteroacyl, $C_6$-$C_{10}$ aryl, $C_5$-$C_{12}$ heteroaryl, $C_7$-$C_{12}$ arylalkyl, or $C_6$-$C_{12}$ heteroarylalkyl group; wherein $R_4$ and $R_5$ are optionally linked to form a 3-8 membered ring, optionally containing one or more N, O or S; and each $R_4$ and $R_5$ groups, and each ring formed by linking $R_4$ and $R_5$ groups together, is optionally substituted with one or more substituents selected from halo, =O, =N—CN, =N—OR', =NR', OR', N(R')$_2$, SR', SO$_2$R', SO$_2$NR'$_2$, NR' SO$_2$R', NR'CONR'$_2$, NR'COOR', NR'COR', CN, COOR', CON(R')$_2$, OOCR', COR', and NO$_2$; wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

5. A method of ameliorating one or more symptoms of a RNA Polymerase I (Pol I) mediated disease or condition in a subject in need thereof, comprising administering to the subject a therapeutically effective amount of a benzo[4,5]imidazo[1,2-a][1,8]naphthyridine compound, or a pharmaceutically acceptable salt, ester, prodrug, hydrate or tautomer thereof, wherein the Pol I associated disease is selected from the group consisting of cancer, diseases and conditions of the immune system, inflammation, diseases and conditions of the central nervous system (CNS), cardiovascular disease, viral infections, dermatological disease, and diseases and conditions related to uncontrolled angiogenesis.

6. A method of treating a proliferative disorder in a mammal in need thereof, the method comprising administering to the mammal a therapeutically effective amount of a benzo[4,5]imidazo[1,2-a][1,8]naphthyridine compound, or a acceptable salt, ester, prodrug, hydrate or tautomer thereof.

* * * * *